United States Patent [19]

Benecke et al.

[11] Patent Number: 5,319,107

[45] Date of Patent: * Jun. 7, 1994

[54] METHOD TO PRODUCE CYCLIC ESTERS

[75] Inventors: Herman P. Benecke, Columbus, Ohio; Alex Cheung, Ft. Collins, Colo.; George E. Cremeans, Groveport, Ohio; Melville E. D. Hillman, Hilliard, Ohio; Edward S. Lipinsky, Worthington, Ohio; Richard A. Markle; Richard G. Sinclair, both of Columbus, Ohio

[73] Assignee: BioPak Technology, Ltd., Golden, Colo.

[*] Notice: The portion of the term of this patent subsequent to Dec. 28, 2010 has been disclaimed.

[21] Appl. No.: 854,559

[22] Filed: Mar. 19, 1992

Related U.S. Application Data

[63] Continuation-in-part of Ser. No. 584,126, Sep. 18, 1990, and a continuation-in-part of Ser. No. 584,466, Sep. 18, 1990.

[51] Int. Cl.$^5$ .................. C07D 319/00; C07D 319/12
[52] U.S. Cl. ...................................... 549/274; 549/379
[58] Field of Search .............................. 549/274, 379

[56] References Cited

U.S. PATENT DOCUMENTS

| | | | |
|---|---|---|---|
| 1,095,205 | 5/1914 | Gruter et al. | 549/274 |
| 1,594,843 | 8/1926 | Lawrie | 549/274 |
| 1,995,970 | 3/1935 | Dorough | 260/2 |
| 2,163,268 | 6/1939 | Carothers et al. | 260/338 |
| 2,174,491 | 9/1939 | Watson | 260/67 |
| 2,189,572 | 2/1940 | Watson | 260/78 |
| 2,668,162 | 2/1954 | Lowe | 260/78.3 |
| 2,703,316 | 3/1955 | Schneider | 260/78.3 |
| 2,758,987 | 8/1956 | Salzberg | 260/78.3 |

(List continued on next page.)

FOREIGN PATENT DOCUMENTS

| | | |
|---|---|---|
| 863673 | 2/1971 | Canada . |
| 0261572A1 | 3/1988 | European Pat. Off. . |
| 0264926A2 | 4/1988 | European Pat. Off. . |
| 221786 | 5/1910 | Fed. Rep. of Germany . |
| 267826 | 12/1913 | Fed. Rep. of Germany . |
| 3632103A1 | 3/1988 | Fed. Rep. of Germany . |
| 53074 | 5/1967 | German Democratic Rep. . |
| WO91/17155 | 11/1991 | PCT Int'l Appl. . |
| WO92/00292 | 1/1992 | PCT Int'l Appl. . |
| 1007347 | 10/1965 | United Kingdom . |
| 1122229 | 7/1968 | United Kingdom . |

OTHER PUBLICATIONS

Bezzi, "The Constitution of Some Polyglycolides", pp. 219-233, 1949, Gazz Chim. Ital., vol. 79.

Bischoff et al., "Ueber das Glycolid und Seine Homologen", pp. 262-265, 1893, Chem. Ber., vol. 26.

Carothers et al., "Studies of Polymerization and Ring Formation. X. The Reversible Polymerization of Six--Membered Cyclic Esters", pp. 761-771, 1932, J. Am. Chem. Soc., vol. 54.

Carothers, "Polymers and Polyfunctionality", pp. 39-53, 1936, Transactions of the Faraday Society, vol. 32.

Deibig et al., "Polytetramethyl Glycolide, I. Synthesis and Properties of Polytetramethyl Glycolide", pp. 123-131, 1971, Die Makromolekulare Chemie, vol. 145.

Deibig et al., "Polytetramethyl Glycolide, II. Thermal Behavior of Polytetramethyl Glycolide", pp. 133-139, 1971, Die Makromolekulare Chemie, vol. 145.

(List continued on next page.)

Primary Examiner—C. Warren Ivy
Assistant Examiner—Raymond Covington
Attorney, Agent, or Firm—Sheridan, Ross & McIntosh

[57] ABSTRACT

Disclosed is a method for producing cyclic esters by the conversion of hydroxy carboxylic acids and their derivatives to their respective cyclic esters. Such cyclic esters, including lactide or glycolide, are particularly useful for producing polymers which can be used to make biodegradable materials, such as biodegradable packaging material. Various methods of cyclic ester production are disclosed, including liquid phase and vapor phase reactions. Also disclosed are various methods for recovering cyclic esters from product-containing streams.

166 Claims, 5 Drawing Sheets

U.S. PATENT DOCUMENTS

| | | | |
|---|---|---|---|
| 2,768,973 | 10/1956 | Castle et al. | 260/602 |
| 3,322,719 | 5/1967 | Peilstöcker | 260/45.8 |
| 3,435,008 | 3/1969 | Schmitt et al. | 260/78.3 |
| 3,457,280 | 7/1969 | Schmitt et al. | 260/340.2 |
| 3,597,450 | 8/1971 | Schmitt et al. | 260/340.2 |
| 3,736,646 | 6/1973 | Schmitt et al. | 29/458 |
| 3,867,190 | 2/1975 | Schmitt et al. | 117/138.8 |
| 3,960,152 | 6/1976 | Augurt et al. | 128/335.5 |
| 4,033,938 | 7/1977 | Augurt et al. | 260/78.3 |
| 4,797,468 | 1/1989 | De Vries | 528/354 |
| 4,835,293 | 5/1989 | Bhatia | 549/274 |
| 4,990,222 | 2/1991 | Aigner et al. | 203/91 |
| 5,023,349 | 6/1991 | Bhatia | 549/274 |
| 5,023,350 | 6/1991 | Bhatia | 549/274 |
| 5,043,458 | 8/1991 | Bhatia | 549/274 |
| 5,053,485 | 10/1991 | Nieuwenhuis et al. | 528/354 |
| 5,053,522 | 10/1991 | Muller | 549/274 |
| 5,068,418 | 11/1991 | Kulprathipanja et al. | 562/580 |
| 5,075,115 | 12/1991 | Brine | 424/486 |
| 5,089,632 | 2/1992 | Paul | 549/274 |
| 5,091,544 | 2/1992 | Bhatia | 549/274 |

OTHER PUBLICATIONS

Dietzel et al., "Über das Chemische Gleichgewicht Zwischen der Milchsäure und Ihren Anhydriden in Wäbriger Lösung", pp. 1307-1314, 1925, Chem. Ber., vol. 58B.

Hill et al., "Cyclic and Polymeric Formals", pp. 925-928, (1935), J. Am. Chem. Soc., vol. 57.

Imasaka et al., "Synthesis of Degradable Terpolymers Responding to External Stimuli Such as pH, Ionic Strength, and Temperature", pp. 715-722, (1991), Makromol. Chem., vol. 192.

Montgomery, "Acidic Constituents of Lactic Acid-Water Systems", pp. 1466-1468, 1952, J. Am. Chem. Soc., vol. 74.

Bezzi, "Transformation of Cyclic Ester into Linear Polyesters", pp. 215-224, (1938), Gazz. Chim. Ital., vol. 68.

Bezzi et al., "Dehydration Products of Lactic Acid Typifying the Transformation of Cyclic Esters into Linear Polyesters", 1936, Meeting of the Italian Academy of Science, Nov.

Filachione et al., "Lactic Acid Condensation Polymers: Preparation by Batch and Continuous Methods", pp. 223-228, 1944, Industrial and Engineering Chemistry, Mar., vol. 36, No. 3.

Holten, "Lactic Acid. Properties and Chemistry of Lactic Acid and Derivatives", pp. 221-231, 1971, Verlag Chemie.

Ikada et al., "Stereocomplex Formation Between Enantiomeric Poly(Lactides)", pp. 904-906, 1987, American Chemical Society, Macromolecules, 20.

Jackanicz et al., "Polylactic Acid as a Biodegradable Carrier for Contraceptive Steroids", pp. 227-234, 1973, The Population Counsel, Sep., vol. 8, No. 3.

Jungfleisch et al., "Organic Chemistry—of Lactyllactyllactic Acid and the Dilactide of Racemic Lactic Acid", pp. 502-505, 1905, Academie des Sciences, Meeting of Feb. 20.

Jungfleisch et al., "Organic Chemistry—on the Dilactide of the Right", pp. 111-113, 1905, Academie des Sciences, Meeting of Jul. 10.

Jungfleisch et al., "Organic Chemistry—on the Dilactide of Left Lactic Acid", pp. 637-639, 1906, Meeting of Mar. 12.

Jungfleisch et al., "Organic Chemistry—on Ethyl Lactyllactate", 1907, Academie des Sciences, Meeting of Feb. 25.

Jungfleisch et al., "Organic Chemistry—on Inactive Dilactylic Acid", p. 979, 1907, Academie des Sciences, Meeting of May 6.

Kleine et al., "High Molecular Weight, Especially Optically Active Polyesters of Lactic Acid: An Investigation of the Stereochemistry of Macromolecular Compounds", pp. 1-21, 1958, Report from the Research Laboratory for Macromolecular Chemistry, Dec.

Kulkarni et al., "Polyactic Acid for Surgical Implants", pp. 839-843, 1966, Arch. Surg., vol. 93, Nov.

Light, "Lactic Acid Resins", pp. 135-136, 1940, Paint Manufacture, Jun.

Watson, "Composition of Lactic Acid. Production of a Highly Concentrated Acid", pp. 399-401, 1940, Industrial and Engineering Chemistry, vol. 32, No. 3.

Wise, "Biopolymeric Controlled Release Systems", pp. 3-28, 1984, CRC Press, vol. 1.

Wise, "Biopolymeric Controlled Release Systems", pp. 187-199, CRC Press, vol. 2.

Wise et al., "Lactic/Glycolic Acid Polymers", pp. 237-270, Dynatech R/D Company, Cambridge, Mass., U.S.A., 1984.

Wislicenus, "On the Optically Active Lactic Acid of Sarcolactic Liquid, the Paralactic Acid", pp. 318-319, 1873, Liebigs Ann. Chem., vol. 167.

METHOD TO PRODUCE CYCLIC ESTERS

CROSS-REFERENCE TO RELATED APPLICATIONS

The present application is a continuation-in-part of U.S. patent application Ser. No. 07/584,126 and U.S. patent application Ser. No. 07/584,466, both filed Sep. 18, 1990, the disclosures of which are incorporated by reference in their entirety.

FIELD OF THE INVENTION

The present invention relates to a method for the manufacture of cyclic esters by the conversion of hydroxy carboxylic acids, referred to herein as hydroxy acids or hydroxy carboxylic acids, and their derivatives to their respective cyclic esters, preferably cyclic compounds with two esters in the same ring. The invention contemplates both a liquid phase conversion and a vapor phase conversion of hydroxy acids to their respective cyclic esters. This invention also includes novel techniques for recovering the cyclic esters.

BACKGROUND OF THE INVENTION

Cyclic esters, including cyclic esters of the general formula

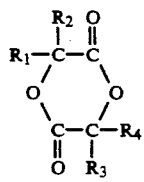

wherein $R_1$, $R_2$, $R_3$, and $R_4$ can be either hydrogen or an aliphatic or substituted or unsubstituted aliphatic or aryl hydrocarbon having from 1 to about 10 carbon atoms, are a useful class of compounds that can be polymerized into polymeric materials. Such polymeric materials are particularly useful in the preparation of biodegradable plastic materials and plastic materials which dissolve when used in medical applications. Polymers made from the polymerization of such cyclic esters as lactide are particularly useful because they can be degraded over time by water hydrolysis under most environmental conditions. The resulting lactic acid units or oligomers of lactic acid are then readily taken up by organisms in the environment and converted to carbon dioxide and water. Cyclic esters are also useful as plasticizers and intermediates for production of surface-active agents and plasticizers.

In accordance with prior practice, the desired cyclic esters were prepared by first condensing hydroxy acids, typically α-hydroxy acids, to an oligomeric prepolymer of relative high molecular weight. The prepolymer was then depolymerized at high temperature and low pressure in a heated, evacuated reactor to a crude cyclic ester. Extensive purification processes were required to obtain cyclic esters of requisite purity sufficient to provide polymers of desired molecular weight.

The production of a cyclic ester from an oligomeric α-hydroxy acid prepolymer is sometimes referred to as a back-biting reaction since it involves the gradual removal of α-hydroxy acid components from the tail ends of the polymer to form the cyclic ester as illustrated below with reference to a lactic acid polymer.

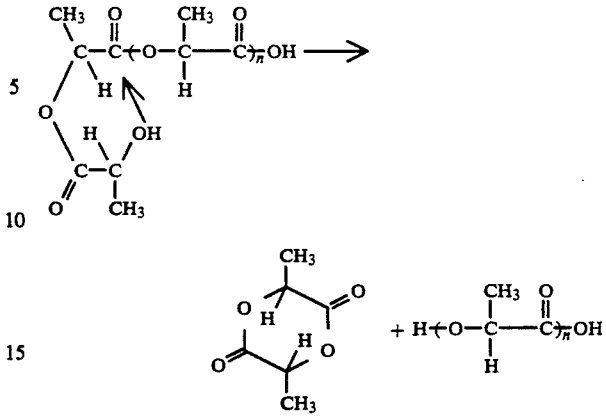

U.S. Pat. No. 4,727,163 to Bellis is directed to a process which includes first making a prepolymer comprising a block polymer which includes a thermally stable polyether core with an α-hydroxy acid or its ester polymerized onto the core. Upon heating under vacuum conditions, the chain ends of the α-hydroxy acids are thermally degraded to form a cyclic ester which can be condensed under vacuum.

U.S. Pat. No. 4,835,293 to Bhatia is directed to a back-biting process which includes the use of an inert gas sweep which permits the process to be operated at or above atmospheric pressure. The inert gas intimately contacts the prepolymer, which is in the liquid phase, so as to create a large interfacial area between the prepolymer and the inert gas to vaporize the cyclic ester and sweep the vapors out of the reactor for subsequent recovery and purification.

As illustrated above, and as discussed in the referenced Bellis and Bhatia patents, back-biting depolymerization of an α-hydroxy acid can result in the production of a cyclic ester. However, the back-biting reaction is typically a slow one, and a batch operation which extends over significant time and which results in an undesirable high molecular weight byproduct heel which must be disposed of and the cyclic ester product must be separated from noxious discolored pyrolysis products.

SUMMARY OF THE INVENTION

The present invention is directed to a process to produce cyclic esters derived from hydroxy carboxylic acids, hydroxy carboxylic acid esters, hydroxy carboxylic acid salts or hydroxy carboxylic acid amides. This process includes providing a feedstream having the above-identified components and treating the feedstream to form a cyclic ester directly from a two member oligomer formed by a single esterification reaction between any two of the above-identified components.

In a further embodiment of the present invention, such a feedstream is treated by removing water from the feedstream which contains the above-identified components and an organic solvent, wherein the concentration of the reactive components in the feedstream is dilute. Preferably, the solvent forms an azeotrope with water and water is removed by heating the feedstream to remove water as an azeotrope.

A further embodiment of the present invention includes treating the reaction feedstream by the removal of water until the degree of polymerization of the mixture, as measured by HPLC, is less than or equal to about 4.

In a further embodiment of the present invention, the feedstream is converted to its vapor phase for treatment at pressure and temperature conditions sufficient to maintain at least a portion of the feedstream in its vapor phase and to form a cyclic ester in a reaction zone. Preferably, this embodiment also includes passing the feedstream vapors through the reaction zone with the aid of a nonreactive hot carrier gas, such as nitrogen.

The present invention further includes recovery of cyclic esters produced by the above-described processes. Such recovery steps include crystallization, solvent extraction, distillation, membrane partitioning, washing with solvent, chromatography, sublimation, and combinations thereof.

The present invention provides multiple advantages including the ability to convert $\alpha$-hydroxy acids directly into cyclic esters of high purity in a continuous process. The process is simple and rapid, particularly as compared to the prior art back-biting process. Another advantage is that any asymmetric carbon atoms which are present in the cyclic ester predominate in the same absolute configuration as in the feedstream source of the $\alpha$-hydroxy acid from which it is made. Alternatively, in a further embodiment of this invention, the chirality may be controlled by selection of catalysts and conditions. Another advantage is a process which is adaptable to recycle any unreacted $\alpha$-hydroxy acid. Yet a further advantage is a process in which little unwanted by-product formation results. These and other advantages will be readily apparent to those skilled in the art, based on the disclosure contained herein.

DETAILED DESCRIPTION OF THE INVENTION

Figure 1:
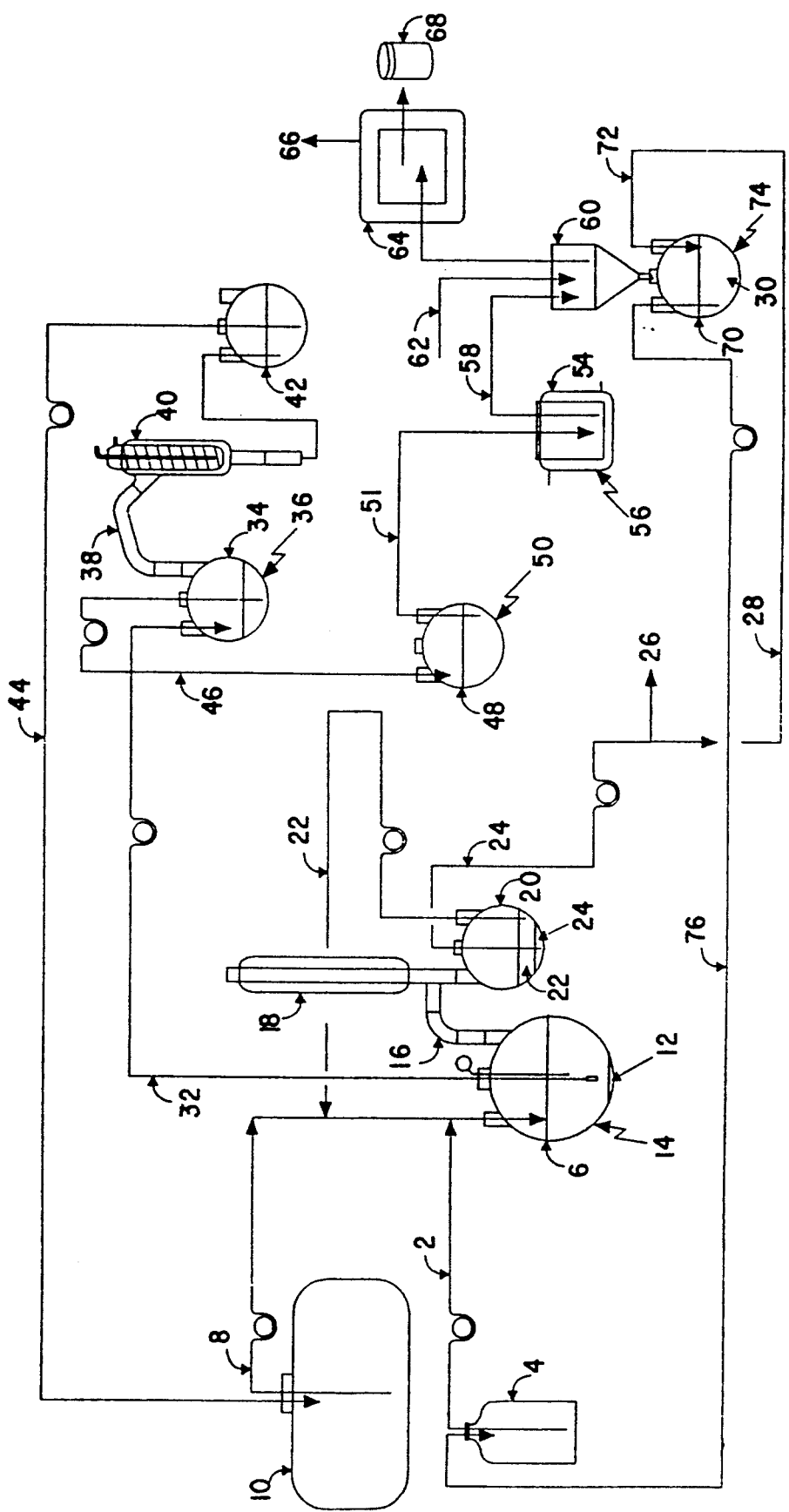
FIG. 1 is a flow diagram representing a process for making a cyclic ester in which water is removed from a feedstream as an azeotrope with an organic solvent.

The present invention provides a process to produce cyclic esters derived from hydroxy carboxylic acids, hydroxy carboxylic acid esters, hydroxy carboxylic acid salts, or hydroxy carboxylic acid amides. As used herein, the term derived from refers to the cyclic ester being produced by reactions in which these components or products of these components were reactants. Preferably, the cyclic esters are formed by converting an ester formed from any two hydroxy acids, esters, salts, or amides thereof, into a cyclic ester. Cyclic esters are also known as lactones. Such preferred cyclic esters are referred to herein as XD. As used herein, $X_1A$ refers to a hydroxy carboxylic acid, hydroxy carboxylic acid ester, hydroxy carboxylic acid salt, or hydroxy carboxylic acid amide. $X_2A$ refers to a molecule formed by a single reaction, e.g. esterification, between any two $X_1A$ molecules to form a straight chain two member molecule of a hydroxy acid or its derivative. $X_3A$ refers to a straight chain three member molecule of a hydroxy acid or its derivative, and $X_nA$ refers to a straight chain n-member molecule of a hydroxy acid or its derivative. As used herein, XA without subscript denotes a single acid species or a mixture of two or more of the acid, $X_1A$, $X_2A$, $X_3A$, and $X_4A$ or a solution containing those species. It will be understood that when X is substituted by L, G or T, the corresponding compounds based on lactic, glycolic and tartaric acid, respectively, are meant. For example, LA refers to $L_1A$, $L_2A$, $L_3A$ and $L_4A$, and LD refers to lactide.

In accordance with an embodiment of the present invention, a cyclic ester derived from $X_1A$ is produced by providing a feedstream containing components including, but not limited to, XA and treating the feedstream to form the cyclic ester. While not wishing to be bound by theory, it is believed that the cyclic ester is formed primarily directly from $X_2A$. Under certain catalytic conditions, it is believed that $X_3A$ and $X_4A$ contribute to cyclic ester formation. As used herein, forming the cyclic ester primarily directly from $X_2A$ refers to a reaction in which $X_2A$ already present in the feedstream or $X_2A$ formed by an esterification reaction between two $X_1A$ molecules is converted to a cyclic ester by esterification. That is, it appears that the cyclic ester is not formed by backbiting of polyester chains, as described in the prior art when a cyclic ester is formed from $X_5A$ or greater.

The role played by water in the present process can be appreciated by reference to the following equilibrium reactions:

$$2X_1A \rightleftharpoons X_2A + H_2O$$

$$X_2A \rightleftharpoons \text{cyclic ester} + H_2O$$

$$X_1A + X_2A \rightleftharpoons X_3A + H_2O$$

Thus, it will be observed that $X_1A$ is in equilibrium with higher oligomers of $X_1A$, cyclic esters and water. By removing water, the reactions are driven to the right and, conversely, by adding water the reactions are driven to the left.

According to the present invention, $X_1A$ is preferably an $\alpha$-hydroxy carboxylic acid, or an ester, salt, or amide thereof. A wide variety of $\alpha$-hydroxy carboxylic acids and their derivatives may be converted to cyclic esters in accordance with the present invention. Such acids include acids of the formula $R_1R_2C(OH)$—COOH wherein $R_1$ and $R_2$ are each independently hydrogen or substituted or unsubstituted aliphatic or aryl hydrocarbons having 1 to 10 carbon atoms and the water soluble salts of such acids. A simple $X_1A$ or mixtures thereof may be used. Suitable $X_1A$ compounds include, but are not limited to, the following acids and corresponding esters, salts, or amides thereof: lactic acid ($L_1A$), glycolic acid ($G_1A$), tartaric acid ($T_1A$), mandelic acid, benzylic acid, 1-hydroxy 1-cyclohexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methylbutanoic acid, 2-hydroxybutanoic acid, 2-hydroxypentanoic acid, and mixtures thereof. The terms $L_1A$, $G_1A$, are $T_1A$ include not only the specific acids but also corresponding esters, salts, or amides. While not wishing to be bound by theory, it is believed that α-hydroxy carboxylic acids or derivatives thereof are particularly suitable for forming XD cyclic esters.

Preferred acids are lactic, glycolic and tartaric acids, with lactic acid being more preferred. Preferred salts are alkyl or aryl amine salts of XA, more preferably ammonium salts of XA, such as organoammonium lactates, and even more preferably ammonium lactate. Additional preferred salts include other lactate, glycolate, and tartrate salts. Suitable esters include short chain alkyl esters, such as those with methyl, ethyl, or butyl chains, as well as those with longer chains, such as octadecyl lactate. Preferred esters include methyl lactate, ethyl lactate and octadecyl lactate. Reference to esters of $X_1A$ does not refer to oligomeric esters or polyesters of $X_1A$. $X_1A$ can be either stereoisomer, namely L- or D-.

Preferred $X_2A$ components are esters between any two hydroxy acids, salts, esters, amides, or mixtures thereof, including $L_1A$-$L_1A$ (or $L_2A$, also known as lactoyllactic acid or lactic acid dimer), $L_1A$-$G_1A$, $L_1A$-$T_1A$, $G_1A$-$G_1A$ (or $G_2A$), $G_1A$-$T_1A$, and $T_1A$-$T_1A$ (or $T_2A$) esters. For example, $L_2A$ can be represented as follows.

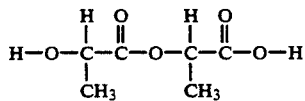

Preferred $X_2A$ components are $L_2A$, $L_1A$-$G_1A$, and $G_2A$ esters. $X_2A$ can contain two L- isomers, two D-isomers or both a D- and an L- isomer. Furthermore, preferred $X_2A$ type esters are methyl lactoyllactate, ethyl lactoyllactate, butyl lactoyllactate, octadecyl lactoyllactate, and ammonium lactoyllactate.

The feedstream of the present process can contain components in addition to XA, including oligomers of $X_1A$, such as $X_5A$ or $X_6A$, and other materials. Preferably, the amount of XA exceeds the amount of $X_nA$, where n is 5 or higher. Preferably, XA components constitute at least about 70 wt %, more preferably 85 wt % and more preferably 90 wt % of total $X_nA$ species. For example, commercial lactic acid is a suitable feedstream and it typically contains from about 60 wt % to about 70 wt % $L_1A$, from about 15 wt % to about 20 wt % $L_2A$, from about 3 wt % to about 6 wt % $L_3A$, from about 0.5 wt % to about 2 wt % $L_4A$, and from about 12 wt % to about 16 wt % water.

The feedstream can alternatively contain a substantial amount of impurities, such as a fermentation broth containing XA which has been partially purified from a fermentation reaction. For example, lactic acid or lactate, such as ammonium lactate, can be partially purified directly from a fermentation broth. Ammonium lactate has the advantage of having the potential of being converted into lactide, water and ammonia gas, which would be easily separated from the product stream.

The feedstream may alternatively contain purified components, such as high purity $L_1A$ or high purity $L_2A$. The concentration of reactive components in the feedstream can be adjusted to achieve high production yields (molar conversion of reactive components to cyclic esters) and high volumetric productivity of cyclic esters for a given cyclic ester production process such as are described below. As used herein, the term reactive components refers to $X_nA$ components and preferably to $X_1A$ and $X_2A$ components.

The feedstream can alternatively include heat stable components, such as heat stable LA. As used herein, the term heat stable LA refers to a lactic acid mixture which can include various LA species, but from which impurities that can cause coloration upon heating have been removed.

In a preferred embodiment of the present invention, the feedstream can contain reactive components which are derived from recycling of polymeric material wherein the polymeric material is made from, e.g., cyclic esters made in accordance with this invention. For example, in the case of a cyclic ester such as lactide, it is suitable for producing polylactic acid. Polylactic acid can be recycled by hydrolyzing it into lactic acid and oligomers of lactic acid. Such a hydrolysis product is suitable for use herein in a feedstream.

The concentration of reactive components in the feedstream can range from about 0.5 wt/vol % to about 99+ wt/vol %. According to a preferred embodiment of the present invention in which liquid phase reactions are employed, the feedstream has lower concentrations of reactive components. It has been found that increased molar conversion of reactive components to cyclic esters can be achieved in this manner. In certain embodiments of the invention, a preferred concentration of reactive components in the feedstream is less than about 75 wt/vol % of the feedstream, more preferably less than about 50 wt/vol %, and even more preferably less than about 25 wt/vol %. While not being bound by theory, it is believed that at lower concentrations, the chance of one $X_2A$ molecule being in close enough proximity to an $X_1A$ or another $X_2A$ molecule for reaction therewith to form $X_nA$ oligomers is relatively small compared with the chance that $X_2A$ will react with itself to form a cyclic ester.

In certain embodiments, the reactive components in the feedstream can be diluted in any solvent to achieve suitable concentrations in the feedstream, preferably such solvents do not contain hydroxyl groups. Preferably an aqueous solvent is not used since water tends to hydrolyze cyclic esters to $X_2A$ and to hydrolyze $X_2A$ to $X_1A$. In general, preferred solvents are organic solvents that are suitable for effective production of cyclic esters according to the method of the present invention. Preferably, the solvent is volatile at a higher temperature than water and/or forms an azeotrope with water.

Dilution of reactive components with the solvent can occur prior to introducing the reactive components into a treatment vessel. Such a mixture of reactive components and solvent is referred to as the feedstream. Alternatively, the feedstream can consist of reactive components and solvent that are added separately to the treatment vessel. In one embodiment, the reactive components are slowly added to the solvent, which preferably is prewarmed in the treatment vessel.

In accordance with the present invention, the feedstream which includes XA, is treated to form cyclic esters. Such treatment can be treatment of a liquid phase feedstream or a vapor phase feedstream. In the case of a liquid phase feedstream, treatment typically includes water removal from the feedstream to promote production of cyclic esters. Without wishing to be bound by any theory, it is believed that the removed water can be derived from at least three sources depending on the specific embodiment under consideration: (1) free water initially in the feedstream; (2) water derived from an esterification reaction to form a linear ester ($X_nA$) between two XA molecules in which n is at least 2; and (3) water derived from an esterification reaction to form a cyclic ester from $X_2A$. Water is believed to result from these three sources sequentially as treatment of a feedstream proceeds. That is, the feedstream typically has free water which is removed first. When the feedstream is thus dehydrated, the esterification of $X_1A$ to $X_2A$ is then favored which produces additional water. As that water is removed, the esterification of $X_2A$ to a cyclic ester is then favored. Since free water is removed during treatment, the initial concentration of water in the feedstream need not be limited. Typically, the amount of free water initially in the feedstream is less than about 50 wt/vol % and more preferably is less than about 30 wt/vol %.

Preferably, when treatment includes water removal, free water in the feedstream is removed rapidly leading to an essentially dehydrated feedstream having a water concentration of less than about 2 wt %. Water formed by the esterification reactions is preferably removed essentially as fast as it is formed. In particular, water is typically removed at a rate such that the concentration of water in the treated feedstream is less than about 2 wt %, more preferably less than about 1 wt %, and even more preferably less than about 0.5 wt %.

Water can be removed from a liquid phase feedstream by a variety of methods, including, but not limited to, removing water as an azeotrope from a feedstream in which the reactive components are diluted in an azeotropic solvent, heating at an elevated temperature below the vaporization temperature of $X_1A$ at an appropriate pressure either in the absence or presence of a nonazeotropic organic solvent, adding a water-getter which preferentially reacts with water, using molecular sieves or partitioning (e.g., osmotic) membranes, using anhydrous salts that form hydrated crystals with water, contacting the feedstream with water absorptive materials, such as polysaccharides (e.g, Ficoll") or silica.

Examples of azeotropic solvents including water immiscible aromatic solvents, water immiscible aliphatic or cyclic hydrocarbon solvents and homogeneous solvents. Particular examples are discussed below. Examples of nonazeotropic solvents include aromatic compounds, such as halogenated aromatics, such as chlorinated aromatics and fluorinated aromatics, naphthalene, and aniline. Examples of water-getters include anhydrides, such as acetic anhydride; ketals, such as dimethyl ketal of acetone; acetals, such as diethyl acetal of acetaldehyde; and carbodiimides. Examples of molecular sieves include zeolites. Examples of anhydrous salts include anhydrous sodium sulfate and anhydrous magnesium sulfate.

Preferred methods for water removal include removing water as an azeotrope with an organic solvent and heating the feedstream under reduced pressure. A more preferred method is removing water as an azeotrope, which will be discussed below.

Treatment of a feedstream containing XA to form cyclic esters can be influenced by several parameters including temperature, pressure, reaction time, presence of a catalyst, and presence of blocking agents.

The temperature of the feedstream treatment controls both the rate of free water removal and the rate of esterification. The temperature of feedstream treatment for esterification and water removal is a temperature, for a given set of other treatment parameters, that is high enough for effective cyclic ester formation and not so high as to convert XA components into aldehydes, carbon monoxide or other degradation products. Preferably, the cyclic ester production temperature ranges from about 55° C. to about 250° C. More preferably the temperature is from about 60° C. to about 225° C. When used, the choice of solvent influences the temperature of the reaction, particularly when the reaction is being conducted at the boiling point of the solvent.

The pressure of the feedstream treatment also influences the formation of cyclic esters. For example, at higher pressures, higher reaction temperatures can be used for a given solvent which results in faster reaction rates, particularly in a vapor phase treatment. The pressure, however, can be either atmospheric, greater than atmospheric or less than atmospheric. A preferred pressure of the present invention is atmospheric pressure.

The feedstream treatment can be conducted for varying times and typically is conducted until cyclic ester formation is substantially maximized as determined by appropriate analytical techniques. The reaction time will of course vary according to other parameters such as temperature and the presence of catalyst. For example, the formation of a cyclic ester such as lactide from commercial lactic acid diluted in toluene by removing water as an azeotrope with toluene by heating from room temperature is substantially maximized within about 2 to about 5 hours. Shorter times may be preferred so as to minimize cyclic ester degradation and racemization.

In all embodiments of the present invention, catalysts can be used to increase the rate of esterification. Although catalysts are not required by the present invention, the use of stable catalysts that do not degrade in the reaction is preferred. For liquid phase production methods, there are many esterification catalysts, which include ring closing esterification catalysts, which can be used including, but not limited to ion exchange acidic catalysts, such as Nafion and Dowex 50; soluble acidic catalysts, such as sulfuric acid, methanesulfonic acid, trifluoromethane sulfonic acid, and toluene sulfonic acid; silica-based catalysts, such as alumina-silicate; other solid heterogeneous acidic catalysts, such as alumina, eta, theta, delta and gamma alumina, silica, aluminum sulfate, lead oxide, antimony trioxide, boron trifluoride, beryllia, yttria; metal ester catalysts, such as stannous octoate and titanium tetra(isopropoxide); enzymes, such as hydrolases; zeolites; so-called template catalysts, such as di-n-butyltin oxide; micellar catalysts, including polar catalysts such as sulfosuccinate salts such as sodium di(2-ethylhexyl) sulfosuccinate sold as Aerosol OT by Pfizer, non-polar catalysts such as polyoxylethylene nonyl phenol, and phosphates. Preferred catalysts include zeolites and acidic catalysts, such as Dowex 50, gamma alumina, and toluene sulfonic acid. For the vapor phase embodiment of this invention, heterogeneous catalysts such as alumina, silica, silica alumina, titania, boric anhydride, aluminotitanates, vanadium oxide, zirconium oxide, alumina-magnesium oxide and alumina-zinc oxide can be used. Homogeneous catalysts such as stannous octoate and titanium tetra(isopropoxide) may also be used. Preferred catalysts for the vapor phase process are gamma alumina, silica and alumina-silica. In the case of liquid phase reactions, the catalyst is typically included in the feedstream and in vapor phase reactions, a catalyst bed can be included in a reaction zone.

The amount of catalyst used will vary depending on treatment parameters, such as temperature and pressure, reactivity of the catalyst and the desired rate of reaction increase. Moreover, it will be recognized that the amount of any particular catalyst for a given system must account for, inter alia, the competition between esterification to produce a cyclic ester from $X_2A$ and esterification to produce higher oligomers from $X_2A$. Thus, depending on reaction kinetics and treatment of a feedstream, optimum amounts of catalyst for production of cyclic ester may exist. At higher or lower amounts of catalyst, conversion rates can decrease.

Use of certain catalysts and other reaction parameters can be controlled to achieve a desired meso-cyclic ester product. For example, with regard to a cyclic ester such as lactide, lactide has two asymmetric carbon atoms so it may be obtained in three stereoisomeric forms: L-lactide in which both asymmetric carbon atoms possess the L (or S) configuration; D-lactide in which both asymmetric carbon atoms possess the D (or R) configuration; and meso-lactide in which one asymmetric carbon atom has the L-configuration and the other has the D-configuration. L-lactide and D-lactide are enantiomers while meso-lactide is a diastereomer of L-lactide and D-lactide in which the methyl groups are trans to each other in the dioxanedione ring. Maintenance of the chirality in L-lactic acid will lead exclusively to the formation of L-lactide which has utility in the production of degradable polymers. However, racemization of the chirality originally in L-lactic acid will lead to the production of meso-lactide which also has a key utility as a comonomer with L-lactide in the production of degradable polymers. By variation of the conditions and catalysts used in each of the embodiments described for this invention, the lactide obtained from L-lactic acid feedstock, or feedstream, may be either nearly exclusive L-lactide or it may contain controlled quantities of meso-lactide in addition to L-lactide. For example, use of an acidic catalyst in the production of lactide has been found to result in increased production of meso-lactide.

In another embodiment of the present invention, blocking or end group agents can be employed to block the formation of hydroxy carboxylic acid oligomers larger in size than $X_2A$. Blocking agents, such as anhydrides, ketones, and aldehydes are useful. In particular, such blocking agents are believed to block alcohol groups on the hydroxy acid, thereby preventing ester formation. Preferably with the use of blocking agents, the feedstream can be enriched for formation of $X_2A$ from $X_1A$ without significant formation of $X_3A$ or higher oligomers. Subsequently, the blocking agents can be removed to permit the formation of cyclic esters from $X_2A$.

The above-described process for the production of cyclic esters is particularly suitable for production of, but not limited to, cyclic esters which are XD. Such XD preferably include, but are not limited to, lactides, glycolide and cyclic esters of tartaric acid, mandelic acid, or 1-hydroxy 1-cyclohexane carboxylic acid. Cyclic esters of the present invention can also be hybrids containing two different $X_1A$ molecules. Cyclic esters can contain two L-$X_1A$'s, two D-$X_1A$'s, or one L-$X_1A$ and one D-$X_1A$. Cyclic esters may be composed of $X_1A$ molecules which can be derivatized to add other functional groups, such as dyes, enzymes, or other proteins. Cyclic esters, such as a cyclic ester between lactic acid and tartaric acid, can form double rings and lead to the formation of branched or crosslinked polymers. Whereas many cyclic esters are composed of six-membered rings, some cyclic esters may also form large rings, such as in the case of caprolactone. The above-described process of the present invention and specific embodiments disclosed below are also suitable for the production of lactones which are dehydration products of monoesters.

Production of cyclic esters in accordance with the general process parameters discussed above and as more particularly described below can result in high conversions of reactive components to cyclic esters. As used herein, unless otherwise noted, the term conversion refers to the molar percent of total theoretical production of cyclic ester per equivalent $X_1A$. Thus, in a feedstream with 100 moles of $X_1A$ and no other reactive components, production of 50 moles of cyclic ester represents 100% conversion of $X_1A$ to the cyclic ester. In a feedstream with 50 moles of $X_2A$ and no other reactive components production of 50 moles of cyclic ester represents 100% conversion of $X_2A$ to the cyclic ester.

Three preferred cyclic ester production processes are generally discussed below. It should be noted that various limitations and parameters discussed in each section may have general applicability.

CYCLIC ESTER FORMATION IN A DILUTE ORGANIC SOLVENT

In a preferred embodiment of the present invention, water is removed from a feedstream containing XA in an organic solvent to form cyclic esters, wherein the concentration of the reactive components is dilute. This embodiment leads to surprisingly high conversions of XA to cyclic esters and in particular, conversion of LA to LD. Any appropriate organic solvent can be used to dilute XA. An appropriate solvent is one in which XA is soluble and which has an appropriate boiling point. Such a solvent is preferably one which does not have reactive hydroxyl groups. Preferably, the solvent forms an azeotrope with water and water is removed by heating the feedstream to remove water as an azeotrope from the feedstream. If the solvent does not form an azeotrope with water, the boiling point of the solvent should be higher than that of water. A preferred feedstream for this embodiment of the process includes LA. Preferably an esterification catalyst is also used to increase the rate of cyclic ester formation. Preferred catalysts include zeolites and acidic catalysts such as Dowex 50 and toluene sulfonic acid.

As noted above, the preferred concentration of reactive components can be less than about 25 wt/vol %. It has been found that high molar conversions to cyclic esters of approximately 50% can be achieved at concentrations as low as 1 wt/vol %. Moreover, it has been found that such conversion can be attained at a concentration range of about 1 wt/vol % to about 20 wt/vol % and more preferably about 1 wt/vol % to about 5 wt/vol %. Thus, by operating at the upper end of these ranges the volumetric production at a high conversion rate can be maximized.

Azeotropic solvents are selected in which reactive components in the feedstream are sufficiently soluble that they remain in solution during the cyclic ester production process. Preferably, azeotropic solvents are also selected which have boiling points that are sufficiently high so that at the boiling point temperature an acceptable rate of esterification is achieved but not so high that the solvent cannot form an effective azeotrope with water or that are converted into aldehydes or other degradation products at the boiling point temperature.

Azeotropic solvents can include water immiscible aromatic solvents, water immiscible aliphatic or cyclic hydrocarbon solvents, water soluble solvents, or mixtures thereof. Preferred solvents are water immiscible aromatic azeotropic solvents. Such solvents include, but are not limited to, benzene, toluene, ethyl benzene, xylenes, cumene, trimethyl benzenes, and alkyl benzene. More preferred water immiscible aromatic azeotropic solvents include benzene, toluene, and xylenes. Toluene is a more preferred water immiscible aromatic azeotropic solvent. Water immiscible azeotropic solvents are preferred because, after distillation, they can be readily separated with the solvent being recycled and the water being taken out of the system.

Hydrocarbons, such as alkanes and alkenes can be used as solvents. Alkanes, such as pentane, hexane, cyclohexane, heptane, and octane can be used as solvents, but $X_1A$ and cyclic esters are often not as soluble in such solvents. Alkenes, such as cyclohexene, may also be suitable for the present invention.

Water soluble azeotropic solvents, such as acetonitrile, can also be used to remove water thereby promoting esterification.

A preferred temperature range for this embodiment of the present process is from about 60° C. to about 140° C. and a more preferred range is from about 80° C. to about 115° C. It should be noted that these temperature ranges include, for any given azeotropic system, the boiling point of the azeotrope and of the organic portion of the azeotrope. That is, as water is initially present in a feedstream and available to form an azeotrope, the reaction temperature will be at the boiling point of the azeotrope. As the water initially present is substantially completely depleted, the reaction temperature will increase to the boiling point of the organic portion of the azeotrope. Because this embodiment of the present process can be conducted at lower temperatures, it is particularly suitable for use with heat labile hydroxy acids and entails reduced energy costs.

Although some variations in temperature affect the rate of cyclic ester formation when water is removed from a dilute solution to form the cyclic ester, such variations in temperature do not appear to affect the total conversion of reactive components to cyclic ester. For example, comparison of the process using the solvents benzene (benzene/water azeotrope boiling point of about 69.25° C., benzene boiling point of 80.2° C.), toluene (toluene/water azeotrope boiling point about of 84.6° C., toluene boiling point of about 110.7° C.), and xylene (xylene/water azeotrope boiling point of 94.5° C., xylene boiling point of 139.1° C.) in a feedstream containing commercial lactic acid indicates that while the water removal rate is greatest with xylene and least with benzene, the overall molar conversion of lactic acid to lactide is approximately equivalent in each solvent.

Removing water as an azeotrope from a feedstream containing XA in order to form a cyclic ester in accordance with the present invention attains molar conversion of at least about 5% of the XA into cyclic esters. In preferred embodiments, the molar conversion is at least about 10%, and more preferably at least about 25%, and even more preferably at least about 50%. It should be recognized that higher conversion rates are attainable and that conversion rates approaching 100% can be achieved, particularly with the recycle of reactive components which are not converted to a cyclic ester.

CYCLIC ESTER FORMATION FROM AN AQUEOUS SOLUTION OF XA

Prior to the discovery of the subject matter of the present application, it was generally thought that cyclic esters such as lactide were unstable in a hot aqueous XA solution. Surprisingly, it has been discovered that during the early stages of the removal of water from aqueous XA until the degree of polymerization of the mixture, as measured by HPLC, is less than or equal to about 4, stable recoverable concentrations of cyclic esters and particularly XD, such as LD, are produced in the aqueous liquid reaction mixture.

As used herein, the degree of polymerization (DP) of a polymer or oligomer having a repeating monomeric moiety is a number-average measure of the number of $X_1A$ moieties per molecule that are in the sample that is being analyzed. The degree of polymerization of lactic acid polymers and oligomers traditionally has been determined by titration as disclosed by Holten, *Lactic Acid, Property and Chemistry of Lactic Acid and Derivatives,* Verlag Chemie, 1971, ISBN 3-52725344-0.

The titration method appears to be valid for analysis of samples that consist primarily of $X_1A$ and $X_2A$. When $X_3A$, $X_4A$ and higher oligomers are present in any significant quantity, the titration method has been found not to be accurate. It has been determined that high performance liquid chromatography (HPLC) provides a direct measure of each oligomer in a sample and therefore, it is only necessary to sum up the individual contributions of each oligomer to obtain the DP. DP measurements by HPLC are generally higher than those by titration when oligomers above $X_2A$ are present. Unless otherwise stated, DP measurements stated herein are by the HPLC method. A suitable HPLC method which will separate L-lactide, meso-lactide and all species of $L_nA$ where n=1–13 is as follows. A reverse phase column is used using an acetonitrile/water gradient while buffering at pH−2.3 with phosphate buffer. A UV detector is used and wavelengths of 195 and 210 nm are monitored. Authentic L-$L_1A$ and L, L-$L_2A$ standards are prepared and are used with pure LD to determine response curves for $L_1A$, $L_2A$ and L-lactide. The response factors for $L_3A$-$L_{13}A$ species are assumed to be identical and are determined by analyzing low DP and high DP $L_nA$ mixtures. The $L_3A$-$L_{13}A$ response factor is found to be similar in magnitude to the response factors of $L_1A$ and $L_2A$.

As noted above, water is removed from the feedstream until the DP of the treated feedstream is less than or equal to about DP 4, more preferably until the DP is less than or equal to about DP 3.5 and even more preferably until the DP is less than or equal to about DP 3.0. Further, water is removed from the feedstream until the DP of the treated feedstream is at least about DP 1.2 and more preferably at least about DP 1.5.

If the dehydration is allowed to continue until the DP exceeds a DP of about DP 4, for example about DP 5 and above, the cyclic ester content rapidly drops to an unacceptably low level. Moreover, if a dehydrated aqueous XA solution having a DP of about DP 4 or below is allowed to equilibrate, the equilibrium reactions disclosed herein will cause a portion of the cyclic ester therein to at least partially react to non-cyclic ester species thereby reducing the amount of recoverable cyclic ester. However, if the partially dehydrated aqueous XA is promptly treated to separate cyclic ester, as for example the prompt separation that occurs in a continuous process, acceptable yields of cyclic ester of about 5% or more by weight of XA may readily be obtained.

A preferred feedstream for this embodiment is commercial lactic acid (about 85% LA and 15% water) which has a DP by HPLC of about DP 1.2. Lactide formation begins substantially immediately upon dehydration of commercial lactic acid. However, until the DP by HPLC reaches about DP 1.4 to about DP 1.5, there is usually insufficient lactide present to warrant recovery. For example, when 85% lactide acid is heated to 122° C. over a period of 86 minutes at a pressure of 100–118 torr, a DP by HPLC of DP 1.29 is obtained and analysis of the dehydrated lactic acid solution showed a lactide content of 1.1 wt %. However, when the dehydration is continued for an additional 64 minutes at 109°–150° C. and 88–83 torr, analysis showed a DP by HPLC of DP 2.02 and a lactide content of 6.9% by weight.

Lactic acid feedstreams suitable for the manufacture of lactide utilizing this embodiment of the present process of the invention through dehydration of lactic acid have the following lactic acid species in the ranges (wt %): about 10% to about 70% $L_1A$, about 10% to about 30% $L_2A$, about 3% to about 20% $L_3A$, about 0.2% to about 15% $L_4A$, about 2% to about 45% lactide, and about 0.2% to about 15% water.

XA feedstreams which have significant quantities of oligomeric $X_nA$ where n is greater than 4 preferably should be hydrolyzed in order to enrich the feedstream in $X_1A$ and $X_2A$. The feedstream can also contain the cyclic ester itself. The presence of cyclic ester in the feedstream appears to have no adverse consequences on conversion of $X_1A$ and $X_2A$ to cyclic ester.

A variety of reactors and reaction schemes can be used for treating the aqueous XA feedstream for removal of water. In a preferred embodiment, an aqueous lactic acid feedstream is heated at a temperature of from about 100° C. to about 220° C., at a pressure of from about 150 torr to about 10 torr to remove water therefrom until a DP by HPLC of about DP 4 or below is obtained. Cyclic esters can either remain in the liquid phase, or if the temperature and pressure are appropriate, at least a portion of the cyclic esters can vaporize and be distilled from the reaction. Significant vaporization of LD cyclic ester can be obtained when LA is dehydrated at higher temperatures, for example, at conditions equivalent to above 180° C., preferably above 195° C. at 85 torr.

In another embodiment, an aqueous XA feedstream is heated to remove water therefrom until a DP by HPLC of about DP 4 or below is obtained to produce cyclic ester in the solution. The cyclic ester-containing solution is then introduced to a codistillation reaction in which a solvent, such as an alkyl benzene, preferably a $C_{10}$–$C_{22}$ alkyl benzene, is vaporized to provide heat transfer for the reaction and for codistillation of cyclic ester. The conditions of the reaction, such as temperature and pressure, are such that as the cyclic ester-containing solution mixes with the vaporized solvent, additional cyclic esters are formed from unreacted components in the cyclic ester-containing solution. The conditions in the reaction are also suitable for distillation of cyclic ester in the codistillation reaction mixture to recover cyclic esters from water, unreacted XA, and oligomers.

CYCLIC ESTER FORMATION IN A VAPOR PHASE PROCESS

In another preferred embodiment of the invention, a portion of an XA feedstream, either all or a smaller portion thereof, is converted to its vapor phase for treatment at pressure and temperature conditions sufficient to maintain said portion of the feedstream in its vapor phase and to form a cyclic ester in a reaction zone. As used herein, the term vapor refers to vaporized material as well as to material which is provided as a fine mist or aerosol. The portion of a liquid XA feedstream to be vaporized may be vaporized in the reaction zone, but preferably is vaporized prior to introduction into the reaction zone. It has been found that high conversion rates can be achieved with this process and unwanted byproducts such as CO and acetaldehyde are at or below acceptable limits. A preferred product from this embodiment of the present process is XD, and more particularly LD.

In general, the concentration of XA in the feedstream that is to be vaporized in the vapor phase process of the present invention comprises from about 50% to about 100% by weight XA containing one or more of the species $X_1A$, $X_2A$, $X_3A$ and $X_4A$ and mixtures thereof and from about 0% to about 50% by weight water. Each of the species $X_1A$–$X_4A$ may be present in an amount of 0% to about 100% by weight so long as the total XA content is 50% or higher.

The vapor phase process preferably is conducted by passing XA feedstream vapors with the aid of a nonreactive hot carrier gas through the reaction zone. The carrier gas can be an inert gas, such as nitrogen or argon, or can be a condensable gas such as $C_{10}$–$C_{20}$ alkyl benzene which is gaseous at the reactor operating conditions. The carrier gas can be present in the reaction zone in an amount of from about 0% to about 99% by weight of the mixture of inert gas and vaporized feedstream. The carrier gas aids in carrying the vaporized feedstream into the reactor and sweeping the crude vaporized cyclic ester-containing product therefrom. An average residence time of a vaporized feedstream in the reaction zone is from about 0.5 to about 12 seconds.

Temperature and pressure conditions are preferably selected at which at least a portion of the feedstream is maintained in vapor phase. Temperature and gas flow conditions are selected at which $X_1A$ and water will preferentially vaporize under conditions of certain temperatures, carrier gas flow rates and pressures. It could be expected that the higher molecular weight $X_2A$ and higher oligomeric species would vaporize to decreasing extents, thereby potentially yielding a nonvolatilized residue when the XA feedstream contains $X_2A$, $X_3A$, and $X_4A$ oligomers. However, these higher oligomeric species may either cyclize directly to lactide or hydrolyze to lower molecular weight species which are then volatilized. It is further believed that cyclic esters formed in the reaction process also preferentially vaporize more readily than $X_2A$, $X_3A$, and $X_4A$ oligomers. It has been found that substantially complete vaporization of LA feedstreams (containing a total of 24% $L_2A$, $L_3A$ and $L_4A$),t hat otherwise might be expected to yield a non-vaporizable residue can readily be obtained. A temperature of from about 150° C. to about 250° C., a pressure of from about 10 torr to about 800 torr, and a wt % organic in inert carrier gas from about 10 wt % to about 50 wt % is preferred.

The yield of cyclic ester can be improved up to approximately three-fold or more through use of esterification and ring closing catalysts which may be the same or different catalyst. Catalysts can be present in the reaction zone either on a fixed support or as a fluidized bed. While not being bound by theory, it is believed that the reactive components of XA adsorb to the catalyst and react to form cyclic esters which then vaporize. Preferred catalysts include eta, theta, delta and gamma alumina, with gamma alumina being preferred, which improve cyclic ester yields while minimizing CO byproduct formation. Other suitable catalysts are silica, mixed alumina-silica, boric anhydride, vanadium oxide, zirconium oxide, strontium oxide and other metal oxides, mixed metal oxides such as alumina/magnesium oxide, alumina/zinc oxide and titanium tetra (isopropoxide), dibutyltin oxide. Catalyst particle sizes ranging from about 2 to 6 mm have been found suitable with smaller sizes being useful when there is incomplete vaporization of the feedstream.

When a catalyst is used in this embodiment, it is preferred that the feedstream be completely vaporized prior to introduction into the reaction zone. The presence of liquid phase XA in a catalyst-containing reaction zone results in lower cyclic ester yields and in greater amounts of impurity byproducts such as carbon monoxide and acetaldehyde, compared to more completely vaporizing the XA feedstream prior to introduction into the reaction zone.

In a preferred embodiment of the vapor phase process, the feedstream contains commercial lactic acid, which is sometimes referred to as 85% lactic acid. In another embodiment, the feedstream contains a source of LA that has been enriched in $L_1A$. It has been determined that a LA-containing feedstream which is highly enriched in $L_1A$, i.e., greater than about 70 wt/vol % L,A and more preferably about 90 wt/vol % $L_1A$, can be prepared by a simple method. In this method, 85% lactic acid is converted to being enriched in $L_1A$ by dilution of the commercial lactic acid with water to prepare an aqueous solution containing about 10-30 wt/vol % lactic acid species with the balance being water. This mixture is equilibrated under reflux until equilibrium is reached, generally 6-8 hours at atmospheric pressure, or for a shorter time under elevated pressure (above 1 atm) and temperature. The equilibrated solution that is obtained has, as lactic acid species, essentially all $L_1A$ with about 0.5% $L_2A$ and essentially zero $L_3A$, $L_4A$ and higher oligomers. Thereafter, water is rapidly distilled from the equilibrated mixture under conditions of temperature and pressure which produce essentially pure anhydrous $L_1A$ containing less than about 2% water and less than about 7 wt/vol % of $L_2A$. The anhydrous $L_1A$ can then be diluted to provide a lactic acid feedstream with various levels of water.

In another preferred embodiment, the feedstream contains nearly anhydrous LA. It has been determined that lactide yields steadily increase as the water content is reduced in predominantly $L_1A$-containing feedstream. In another preferred embodiment, the feedstream consists of nearly anhydrous LA which is enriched in $L_2A$, $L_3A$ and $L_4A$. The higher yield of lactide produced by 85% commercial lactic acid compared to feedstream containing 84.9% predominantly $L_1A$ feedstream may be attributed to the higher percentages of $L_2A$, $L_3A$ and $L_4A$ contained therein (24.0%). A nearly anhydrous lactic acid feedstream containing a total quantity of $L_2A$, and $L_3A$ of approximately 10-50% is believed to be a suitable feedstream.

In one preferred embodiment of the invention, a continuous catalyzed vapor phase process for converting an alpha-hydroxycarboxylic acid or ester to a dimeric cyclic ester is provided, which process comprises:

(i) continuously vaporizing the hydroxycarboxylic material and feeding it to a reaction zone containing a solid catalyst effective to oligomerize and cyclize the carboxylic material to the cyclic ester, (ii) maintaining the reaction zone at a temperature and pressure effective to result in the formation of the cyclic ester and maintain it in the vapor phase, and (iii) recovering the cyclic ester from the vapor phase.

When a portion of the feedstream is vaporized in the present process, the non-vaporized portion typically includes oligomers of $X_1A$. Such a non-vaporized portion can be hydrolyzed to XA components and recycled for use in a feedstream.

RECOVERY OF CYCLIC ESTER

Cyclic esters produced in accordance with the present invention are typically recovered from the feedstream in which they were produced (i.e., the product-containing stream). As discussed above, such recovered cyclic esters are suitable for use, inter alia, as a monomer in production of polymers which are biodegradable. As used herein, the term recovery refers to the separation of cyclic esters from a treated feedstream and, optionally, subsequent purification thereof.

A number of methods can be used to recover cyclic esters produced in accordance with the present invention from the product-containing stream, including, but not limited to, crystallization, solvent extraction, washing with solvent, distillation, membrane partitioning, chromatography, sublimation, and combinations thereof. It should be noted that the various methods of recovery are based on differences between cyclic esters and other species in the product-containing stream in terms of volatility, solubility, and affinity in various chromatography applications.

A preferred recovery method of the present invention is crystallization, which can be used regardless of which method is used to produce the cyclic ester. An advantage of crystallization is that it is possible to crystallize the cyclic ester essentially free of $X_1A$, $X_2A$, $X_3A$, $X_4A$ and hydroxy acid ester oligomers, i.e., the crystallized cyclic ester is typically at least about 90% pure and a purity of at least about 99% and more preferably at least about 99.9% can be achieved.

In order to crystallize the cyclic ester, components of the product-containing stream, which include the cyclic ester, unreacted components, and oligomers, are typically contacted with an appropriate solvent, which can be the solvent already in the product-containing stream, in which the cyclic ester is less soluble than other components in the product stream and cooled slowly until crystals of the cyclic ester form. In a preferred embodiment, the product-containing stream can be initially heated to ensure that all components are in solution and/or subsequently incubated after cooling at a temperature of from about 0° C. to about 10° C. for a time effective to maximize crystal formation. Cyclic ester crystals can be recovered by a variety of techniques, including centrifugation and filtration. The crystals can be washed and subsequently dried, for example by vacuum evaporation, or be kept in an appropriate solvent for polymerization. Cyclic ester crystals can also be submitted to additional steps of dissolution and crystallization to obtain crystals having a higher purity. Typically at least about 50%, preferably at least about 80% and more preferably at least about 95%, of the cyclic esters can be recovered by crystallization.

Crystallization of cyclic esters from a product-containing stream that includes solvent can be conducted using either the same solvent or a second solvent. Crystallization of cyclic esters directly from the same solvent is a preferred process because it does not require removal of the first solvent and addition of a second solvent. In addition, any unreacted components and/or oligomers remaining in solution after crystallization of the cyclic ester can be recycled directly to the feedstream.

Oligomers in any such recycle stream can be hydrolyzed by adding water to the solvent prior to recycling it to the feedstream. Such water can be subsequently removed as part of the cyclic ester production process. Preferred solvents for production of cyclic esters and crystallization of the cyclic esters therefrom include aromatic water immiscible azeotropic solvents. Particularly preferred solvents are toluene, benzene and xylene.

In order to crystallize cyclic esters from a dilute solution in which the cyclic ester is fairly soluble, an evaporation step may be employed to remove most of the solvent. Preferably, sufficient solvent is removed by evaporation to yield a solution containing at least about 30 wt/vol %, more preferably at least about 50 wt/vol % and most preferably at least about 60 wt/vol % cyclic ester. Evaporation is typically conducted under a vacuum with heat.

In another embodiment, the solvent from the product-containing stream is removed, typically by evaporation, to form a residue, and the residue is dissolved in a second solvent from which the cyclic ester is crystallized. This method is particularly advantageous when the cyclic ester is too soluble in the first solvent to be crystallized. Examples of first solvents in which a cyclic ester, such as lactide, may be too soluble are acetone and acetonitrile. The second solvent can be a solvent in which the cyclic ester can be dissolved and from which the cyclic ester can be crystallized. With respect to a cyclic ester, such as lactide, such solvents include, for example, methyl isobutyl ketone and diethyl ether. After crystallization, the unreacted components and oligomers that remain in the second solvent can be recovered, hydrolyzed as necessary, and cycled to the feedstream.

In yet another embodiment, cyclic esters present in the product-containing stream can be crystallized by adding a second solvent to the stream which causes the cyclic esters to crystallize. Such a second solvent, for example, is one which, when mixed with the first solvent, the cyclic ester can be crystallized from the solvent mixture. For example, cyclic esters such as lactide in an aromatic azeotropic solvent, such as toluene, may be precipitated by the addition of certain alkane solvents, such as pentane.

In accordance with another embodiment of the present invention, cyclic esters produced in a vapor phase reaction can be crystallized or condensed directly from the vapor phase product-containing stream by introducing the stream into a collector, such as a cyclone or centrifuge, which is at a low temperature below the vaporization temperature of the cyclic ester and preferably at about 5° C. or less. After condensing the cyclic ester, the cyclic ester can be washed with cold water. Crystals formed thereby are scraped from the collector, washed, filtered, and dried. In addition, cyclic esters produced in the vapor phase process can be recovered by mixing the hot vaporized product stream with a cold water spray and/or cold inert gas stream to cause rapid cooling and product precipitation.

The present invention can also include the use of solvent extraction to recover cyclic esters from a product-containing stream. For example, cyclic esters may be recovered by contacting the product-containing stream with a second solvent in which cyclic esters are more soluble than they are in the first solvent and in which unreacted components and oligomers are less soluble than they are in the first solvent. Such solvents include xylenes, methyl isobutyl ketone, ethyl acetate, butyl acetate, methylene chloride or other halogenated solvents.

In another embodiment, cyclic esters produced in a liquid phase reaction can be recovered from the liquid phase by bubbling an inert gas, such as argon or nitrogen, through the liquid phase, preferably in such a manner that maximizes contact between the liquid and gas phases. Cyclic esters, water, and unreacted components are carried from the liquid phase by the gas, which is subsequently condensed. Water and unreacted components can be extracted from cyclic esters by a variety of methods, including cold water washing and methylene chloride/sodium bicarbonate extraction.

In a further preferred embodiment, the product-containing stream can be contacted with a water soluble solvent, such as acetonitrile and/or tetrahydrofuran, and subsequently contacted with water to precipitate the cyclic ester.

In a further preferred embodiment of cyclic ester recovery in the present invention, the product-containing stream is contacted by an aqueous solvent at temperatures sufficiently low so as to not hydrolyze the cyclic esters. The aqueous phase, which is preferably water or a dilute base, extracts unreacted components and any oligomers from the cyclic ester-containing stream which are more soluble in the aqueous phase than in the solvent of the product-containing stream. In an embodiment, the dilute base can be a dilute solution of sodium bicarbonate. The resulting cyclic ester-containing stream, which typically includes an organic solvent such as toluene, can then be used after thorough drying as a feedstream to a polymerization reaction or as a source for crystallization of the cyclic ester. The aqueous phase containing the unreacted components and oligomers can be recycled directly to the feedstream with the aqueous phase preferably being warmed to hydrolyze any oligomers.

Recovery of cyclic esters from a product-containing stream can also be accomplished using membrane partitioning. For example, the stream can be contacted with a hydrophobic membrane through which the cyclic ester can pass, but unreacted components and oligomers do not. For example, suitable membranes include a gas permeable membranes. One advantage of membrane partitioning is that cyclic esters can be recovered as they are being produced.

In yet another embodiment of recovery, cyclic esters can be recovered by sublimation. Any solvent in the product-containing stream which also includes oligomers and non-cyclic ester components is first removed by, for example, evaporation to produce a residue. Conditions of sufficient heat and vacuum are applied to the residue in the presence of a cold trap so that the cyclic ester vaporizes and then is collected on the cold trap. Conditions are such that oligomers in the residue do not vaporize and vaporized XA components do not condense.

In accordance with another embodiment of the present invention, cyclic esters can be recovered by distillation, such as by fractional distillation or codistillation. A convenient cyclic ester recovery process involves extractive distillation utilizing an organic solvent to facilitate vaporization of the cyclic ester. The solvent is vaporized, both to provide heat transfer in the recovery reaction and to promote codistillation of the cyclic ester with the solvent. As described earlier, such a codistillation process can also lead to the production of additional cyclic esters from unreacted components in the cyclic ester-containing solution. Particularly useful is a solvent that is immiscible with cyclic ester and oligomer ($X_nA$) species. One class of codistillation solvents meeting the preferred requirements comprises alkyl benzenes, especially those with a boiling point equal to or slightly higher than that of the cyclic ester. For example, if the cyclic ester is lactide, the preferred boiling point of the codistillation solvent would be from about 215° C. to about 220° C. at 60 torr. Representative preferred alkyl benzene codistillation solvents include higher alkyl benzenes such as $C_{10}$–$C_{22}$ alkyl benzenes, preferably $C_{11}$–$C_{14}$ alkyl benzenes and more preferably, dodecyl benzene or tridecyl benzene. Distillation solvents that have an average composition of dodecyl benzene also are quite appropriate for use in the present invention. These mixed solvents supply the necessary heat transfer, are non-toxic and are commercially available. The byproduct residue remaining after removal of cyclic esters contains oligomers that can be hydrolyzed to enrich for $X_1A$ and $X_2A$. When distillation is the separation treatment of choice, the still bottoms may also be treated for readmission to the process; most often, hydrolysis enrichment for $X_1A$ and $X_2A$ typically is recommended.

The present invention can be conducted in a variety of modes including, but not limited to batch, semi-continuous, and continuous. Unreacted components, oligomers, and solvents can be recycled, particularly in a continuous process. One advantage of a continuous process in which unreacted components, hydrolyzed oligomers, and solvents are recycled is the ability to obtain high molar conversions of XA to cyclic esters.

Since the product-containing stream can contain high levels of $X_1A$, for example up to 50 wt %, the cyclic ester production process is especially amenable to the use of a recycle stream containing the unreacted $X_1A$ which may be mixed with make-up XA to form the feedstream components of the process. In addition, oligomers may be hydrolyzed by adding water to the cyclic ester-depleted fraction prior to recycling the fraction to the feedstream. Recycling substantially increases the overall yield of cyclic esters; overall molar conversion to cyclic ester exceeding 90% can be expected when employing such recycle techniques.

With reference to FIG. 1, a continuous process to produce cyclic esters in which key components are recycled is depicted. In the diagrammed process, water is removed as a heterogeneous azeotrope between water and the solvent (e.g., toluene).

Feedstream reactive components 2, including XA, from feedstream component container 4 are added to a treatment vessel 6 along with heterogeneous azeotropic solvent 8 from a solvent container 10. The feedstream reactive components 2 and solvent 8 are added continuously to the vessel 6 in the proper proportions. Free water in the feedstream reactive components 2 ca be removed prior to adding the feedstream reactive components 2 to the treatment vessel 6 or the free water can be removed during the treatment in the vessel 6. A solid catalyst 12 can be added to the treatment vessel 6 or a miscible catalyst can be added along with the feedstream reactive components 2.

The treatment vessel 6 is heated by a heat source 14 to a temperature sufficient to promote cyclic ester formation and to remove water as an azeotrope with the solvent. The vaporous azeotrope 16 is passed through a condenser 18 in which the heterogeneous azeotrope condenses to form organic and aqueous phases. All of the organic solvent-containing phase 22 is returned (total reflux) to the treatment vessel 6. The water-containing phase 24 is removed to waste 26. Alternatively, at least a portion of the water-containing phase 28 can be used to hydrolyze oligomers in the product waste stream, or filtrate 30 that is recycled to the feedstream component container 4.

A product-containing stream 32 containing cyclic esters, unreacted components, oligomers and the organic solvent is removed from the treatment vessel 6 at a rate such that the average residence time of the feedstream in the treatment vessel 6 is about 3 to about 4 hours. The product-containing stream 32 is preferably removed at about the same rate at which the combination of solvent 8 and feedstream reactive components 2 are added to the treatment vessel 6 so as to maintain a constant volume in the vessel 6.

The product-containing stream 32 is introduced into a concentrator vessel 34 which is heated by a heat source 36 to remove, preferably by evaporation at an appropriate pressure (e.g., under vacuum), a majority of the solvent from the stream. The evaporated solvent 38 is passed through a condenser 40 to condense the solvent. The condensed solvent is then collected in a solvent collector 42 prior to recycling 44 to the solvent container 10. If necessary, the solvent in the solvent collector 42 can be cleaned to remove impurities.

The concentrated product-containing stream 46 can be held in a stream collector 48 and heated by a heat source 50 prior to crystallization. In order to recover the cyclic ester by crystallization, the concentrated and heated product-containing stream 51 is transferred to a crystallization flask 54 which is cooled by a cooling source 56 to promote increased crystallization of the cyclic ester. The crystallization flask 54 is typically insulated to maintain the cold temperature required for crystallization. After crystallization, the crystal-containing slurry 58 is filtered through a filter 60 to separate the cyclic ester crystals from the solvent which contains unreacted components and oligomers. For example, a Buchner funnel can be used to collect the crystals. The crystals may then be washed with a cold solvent wash 62 and dried in an oven 64, preferably under vacuum 66. The cyclic ester crystals 68 may then be further purified or used directly to make hydroxy acid polyesters.

The filtrate 30, which contains unreacted components, oligomers, and solvent, is collected in a collection vessel 70. In a preferred process, the oligomers in the filtrate 30 are hydrolyzed to substantially $X_1A$ or $X_2A$ by adding water 72 to the collection vessel 70 and heating with a heat source 74. The water 72 which is added to the collection vessel 70 may include waste water 28 removed from the treatment vessel 6 by azeotropic distillation. The filtrate 30, preferably hydrolyzed, is then recycled 76 to the feedstream component container 4.

Figure 2:
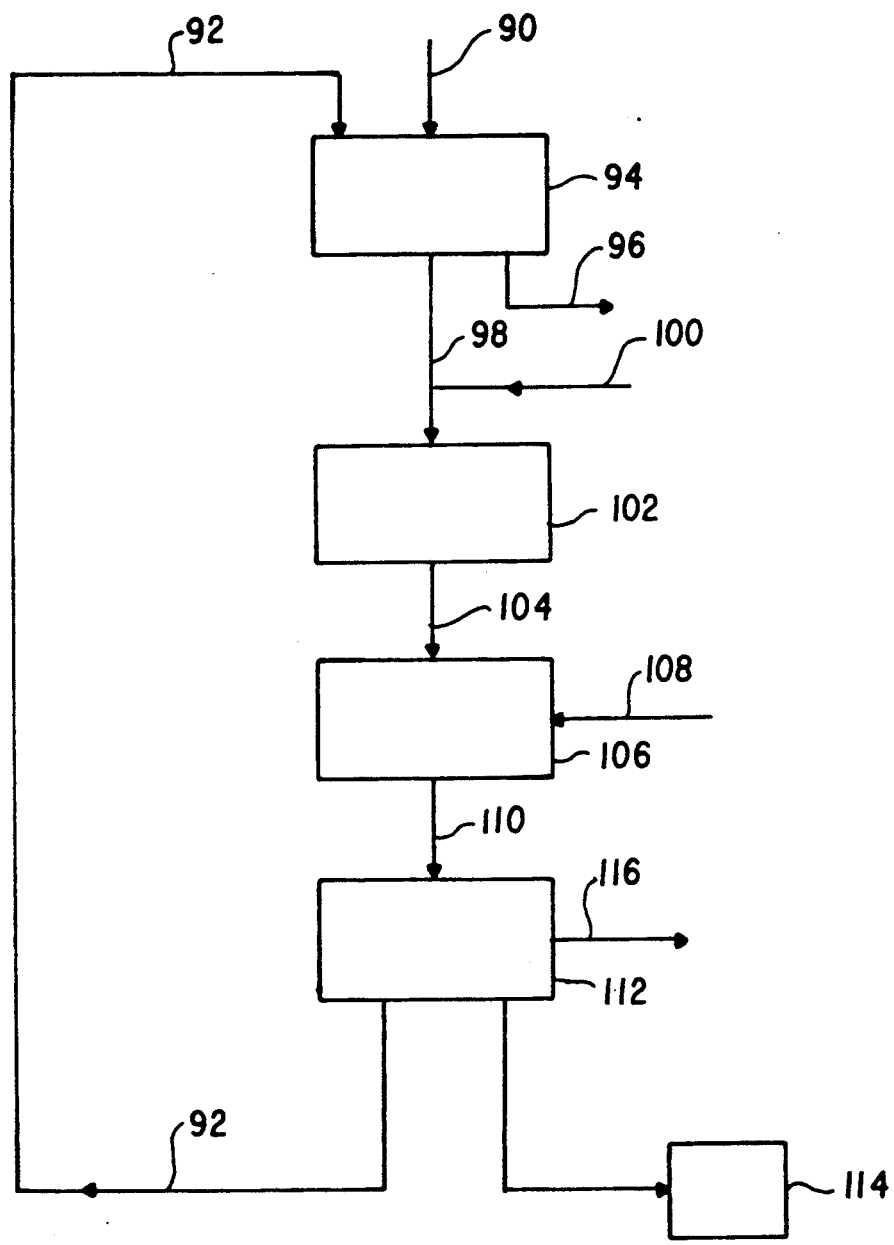
FIG. 2 is a flow diagram representing a process for making a cyclic ester directly from an $\alpha$-hydroxy acid feedstream in accordance with the present invention.

A flow chart for a vapor phase embodiment of the present process is illustrated in FIG. 2. A make-up aqueous LA feedstream 90 and a recycle LA stream 92 are introduced into a heating zone 94 which may be a distillation still. Water is distilled from the contents in the still 94 and withdrawn via line 96 in order to provide a feedstream 98 having a DP of 4 or lower and a predominance of $L_1A$ and $L_2A$. Depending upon the make-up of the recycle stream, lactide may also be distilled, and if present, can be recovered from the distilled water by solvent extraction.

The heated lactic acid feedstream 98 is mixed with a hot nitrogen carrier gas stream 100 heated to an elevated temperature sufficient to vaporize a portion of the LA feedstream and passed into reactor 102, which may contain a bed of catalyst, preferably gamma alumina, as set forth herein.

The reaction conditions in reactor 102 are selected in order to insure that the vaporized LA feedstream and the lactide formed in the reactor are in the vapor state. A temperature of from about 150° C. to about 250° C., a weight percent organic in the inert carrier gas of 10%–50%, and a pressure of from about 10 torr to about 900 torr have been found to be suitable.

A vaporized crude lactide product stream 104 is withdrawn from reaction zone 102 and introduced into collector 106 which suitably may be a cooled cyclone, centrifuge or similar apparatus. Under laboratory conditions, using a cyclone maintained at −78° C., a crystalline mass collected directly below the inlet tube was enriched in lactide. The interior surface of the cyclone 106 was scraped and washed with cold water 108 and the contents passed via line 110 into separator 112 where it was cooled, stirred and filtered for removal of lactide product from the filtrate via line 114. Lactide typically was dried under vacuum in the presence of phosphorous pentoxide to remove tightly bound water. Exhaust carrier gas is collected via line 116 and passed through various traps (not shown) in order to condense condensable material contained therein. The filtrate from separator 112 is introduced as recycle stream 92 into heating zone 34 to complete the cyclic process. It will be appreciated that a variety of collection/separation schemes can be envisioned with respect to separation of the lactide product.

Figure 3:
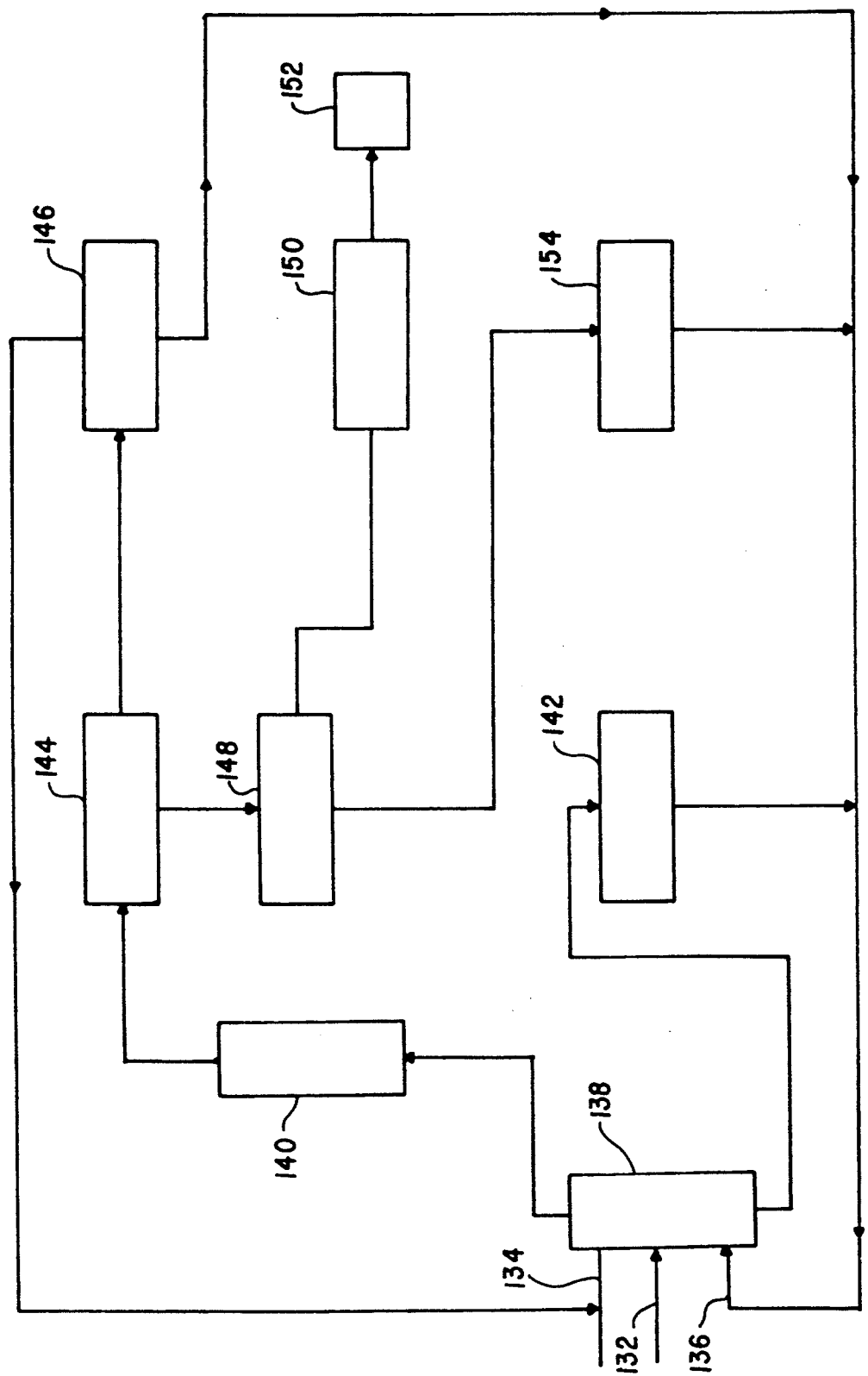
FIG. 3 is a flow diagram representing another embodiment of a process for making a cyclic ester directly from an $\alpha$-hydroxy acid feedstream in accordance with the present invention.

Another embodiment of the vapor phase process of the present invention is set forth in FIG. 3. In this embodiment, a lactic acid make-up stream 132, a nitrogen carrier gas stream 134 and a recycle stream 136 are continuously introduced into a vaporizer 138. It is contemplated that two or more of these streams may be mixed together prior to introduction into vaporizer 138. The streams entering vaporizer 138 may be preheated, as desired, or the nitrogen may be supplied in a quantity and preheated to a temperature sufficient to vaporize the lactic acid feedstream and the recycle stream. Sufficient heat is supplied to vaporizer 138 to completely vaporize the $L_1A$ and water present therein. Minor amounts of $L_2A$ and higher oligomers, depending upon vapor pressure considerations may also vaporize.

The carrier gas and vaporized lactic acid are transported to a reactor 140 containing a bed of a catalyst, preferably gamma alumina catalyst. Those unvaporized higher lactic acid oligomers which fall to the bottom of vaporizer 138 and do not cyclize or hydrolyze to vaporizable lactic species are transported to a hydrolyzer 142 where they are hydrolyzed to provide a recycle component enriched in $L_1A$ and $L_2A$.

The crude product stream from reactor 140 is introduced into condenser 144 where unreacted $L_1A$, lactide and water are condensed from the carrier gas. The carrier gas is treated, such as by water scrubbing in scrubber 146, and recycled to the process. The condensed crude vapor product stream exiting the condenser typically contains from about 20 wt % to about 40 wt % lactide, from about 10 to about 50 weight percent $L_1A$, and from about 10 wt % to about 30 wt % water. Little or no $L_2A$ and higher oligomers are found in the crude product stream. Lactide is recovered from water, unreacted $L_1A$ and other lactic acid species that may have formed post reactor 140 in separator 148 by a suitable method, such as crystallization of the lactide in cold water. The recovered lactide is washed in purifier 150 to recover purified lactide 152.

The unreacted LA is adjusted in lactic acid species and DP in adjuster 154, preferably to maximize $L_1A$ and $L_2A$. The adjusted lactic acid stream is combined with the output of hydrolyzer 142 to provide recycle stream 136.

The following examples show how the present invention has been practiced, but should not be construed as limiting. In Examples 8 through 55, all percentages and proportions are by weight unless otherwise indicated and all units are in the metric system, unless otherwise expressly indicated. Also, all citations referred to herein are incorporated expressly herein by reference.

EXAMPLES

EXAMPLE 1

This Example demonstrates the ability to form lactide using L,-D-lactic acid as a feedstream.

About 85–88% L-,D-lactic acid (obtained from Kodak) was mixed with toluene at a ratio (vol/vol) of lactic acid to toluene of 10:190 in a total of 200 ml, giving a feedstream containing about 5 wt % lactic acid. One gram of the catalyst Dowex-50 H+ ion exchange resin was added to the mixture which was heated using a heating mantle. As the temperature of the mixture reached about 85° C. free water was removed from the mixture as an azeotrope with toluene (boiling point of the 18% water / 82% toluene azeotrope is 84.6° C.). After most of the free water was removed (within about 20 to about 30 minutes), the temperature of the mixture continued to increase to about 110.7° C. the boiling point of toluene. The mixture was allowed to remain at about 110° C. for about 72 hours to maximize lactide production. The toluene was then removed from the mixture by evaporation using a rotary evaporator, at a temperature of about 40° C. to about 50° C. The dried residue of lactide, lactic acid, and oligomers was dissolved in a minimum amount of diethyl ether required to dissolve the residue at a temperature close to the boiling point of the diethyl ether (about 40 ml to about 50 ml). The lactide was then crystallized from solution by incubating the solution at about 4° C. The recovery of lactide (mole % yield, i.e., moles of lactide recovered per moles of theoretical total lactide formation) was about 13%. The purity of the product was greater than 90%, possibly even greater than 95%, as indicated by the melting point of the crystals. (A mixture of D- and L- lactide typically melts at about 120° C.) In addition, HPLC analysis of the product yielded a single peak.

EXAMPLE 2

In this Example, lactide was formed in a solution containing about 5 wt % L-lactic acid.

About 85% heat stable L-lactic acid (obtained from Pfhanstiehl) was mixed with toluene at a ratio (vol/vol) of lactic acid to toluene of 10:190 in a total of 200 ml, giving a feedstream containing about 5 wt % lactic acid. One gram of the catalyst Dowex-50 H+ ion exchange resin was added to the mixture which was heated using a heating mantle. As the temperature of the mixture reached about 85° C. free water was removed from the mixture as an azeotrope with toluene (boiling point of the 18% water / 82% toluene azeotrope is 84.6° C.). After most of the free water was removed (within about 20 to about 30 minutes), the temperature of the mixture continued to increase to about 110.7° C. the boiling point of toluene. The mixture was allowed to remain at about 110° C. for about 24 hours to maximize lactide production. About 2 ml samples were removed at several time points during the polymerization to measure the amount of lactide and lactic acid oligomers produced throughout the reaction.

The toluene solvent was then removed from the mixture by evaporation using a rotary evaporator, at a temperature of about 40° C. to about 50° C. The dried residue of lactide, lactic acid, and oligomers was dissolved in a minimum amount of diethyl ether required to dissolve the residue at a temperature close to the boiling point of the diethyl ether (about 40 ml to about 50 ml). The lactide was then crystallized from solution by incubating the solution at about 4° C. Recovered crystals were at least about 90% pure, as determined by the melting point of the crystals and HPLC analysis. L-lactide melts at about 97° C. to about 98° C.

Figure 4:
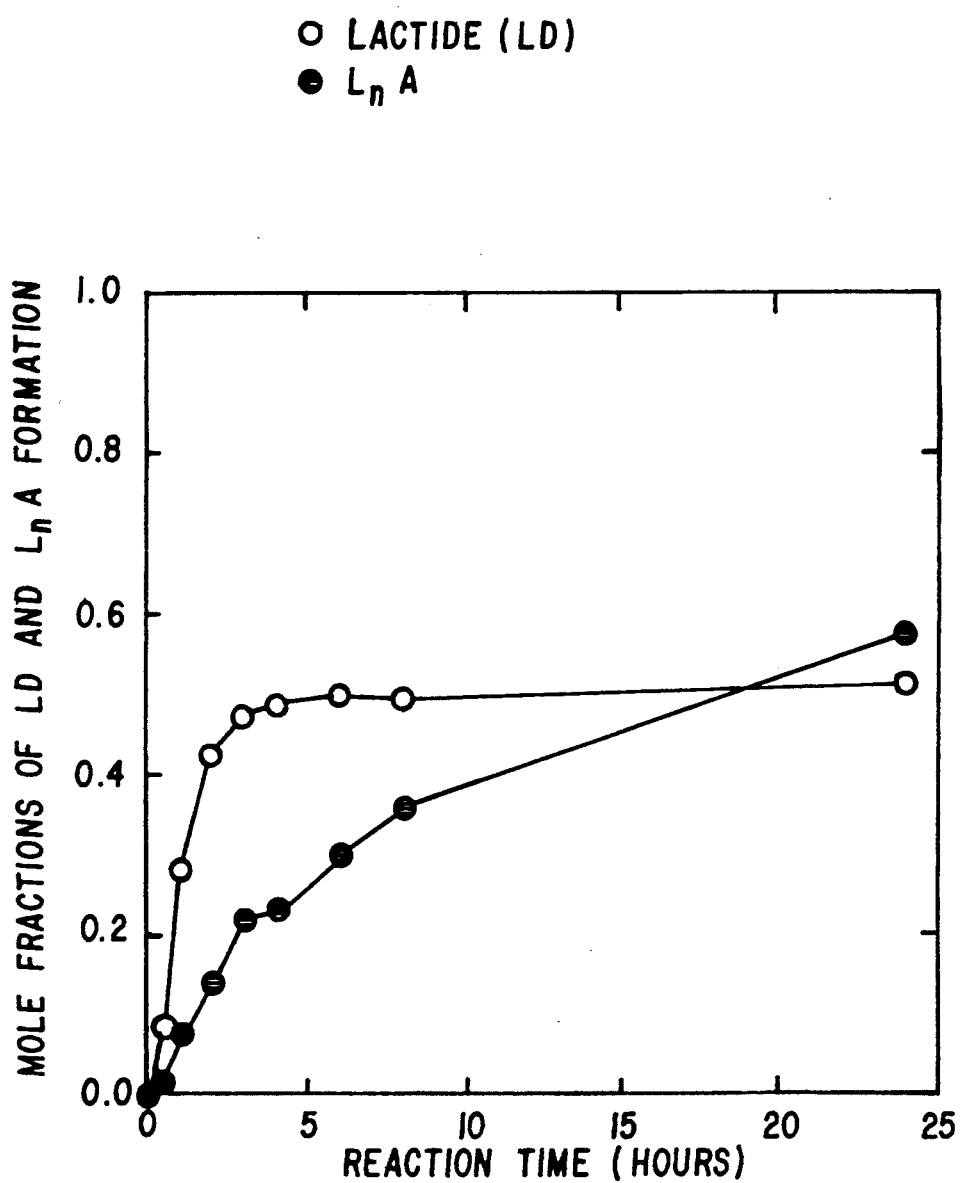
FIG. 4 depicts lactide production over time produced by the removal of water as an azeotrope as disclosed in Example 2.

Results of the analysis of samples removed during the reaction are presented in FIG. 4 and Table 1, which compare the amount of lactide (LD) and $L_nA$ produced during a reaction time of about 24 hours, as determined by HPLC analysis.

TABLE 1

| Reaction Time (hrs) | Lactide Formation (mg/ml)* | Total LnA Formation (mg/ml)* |
|---|---|---|
| 0 | 0 | 0 |
| 0.5 | 3.8 | 0.7 |
| 1 | 12.5 | 3.4 |
| 2 | 19.3 | 6.3 |
| 3 | 21.0 | 9.8 |
| 4 | 21.7 | 10.4 |
| 6 | 22.3 | 13.3 |
| 8 | 22.0 | 15.9 |
| 24 | 22.9 | 25.6 |

*The above numbers are derived from HPLC peak integrations using a response factor, as described above. The total LnA in mg/ml is calculated assuming the response factors for LnA are the same as for lactide.

The Table presents the data as mg of lactide or LnA produced per ml of solvent, whereas FIG. 4 presents the same data shown as mole fraction of lactide or $L_nA$ formed in the reaction. At later time points, (e.g., at 24 hours), the sum of the mole fractions of lactide and $L_nA$ formed is slightly over 1. This inaccuracy may be due either to evaporation of the solvent during the 24 hour reaction, or the response factors used to calculate $L_nA$ from the HPLC data may be slightly different from the response factor for lactide.

The maximum amount of lactide produced occurred between about 3 and about 6 hours after the beginning of the reaction and remained constant at least until 24 hours after the initiation of the reaction. Lactic acid species at about 3 to about 6 hours after the start of the reaction were predominantly $L_3A$, $L_4A$ and $L_5A$. Oligomers of increasing size continued to form at least until 24 hours after the initiation of the reaction.

The molar conversion of lactic acid to lactide was about 50%. A molar conversion of 100% assumes that 1 lactide molecule is formed for every 2 lactic acid ($L_1A$) molecules in the initial feedstream; for Examples 2 through 7, all lactic acid species in the Pfhanstiehl lactic acid are assumed to be $L_1A$. The recovery yield of lactide was about 25%.

EXAMPLE 3

This example tested the ability of lactide to be crystallized from toluene.

About 85% heat stable L-lactic acid (by Pfhanstiehl) was mixed with toluene at a ratio (vol/vol) of lactic acid to toluene of 10:190 in a total of 200 ml, giving a feedstream containing about 5 wt % lactic acid. One gram of the catalyst Dowex-50 H+ ion exchange resin was added to the mixture which was heated using a heating mantle as described in Example 2. The reaction was continued for about 24 hours to maximize lactide production, although maximum lactide synthesis was achieved by about 3 to about 6 hours.

The toluene solvent was then removed from the mixture by evaporation using a rotary evaporator, at a temperature of about 40° C. to about 50° C. The dried residue of lactide, lactic acid, and oligomers was dissolved in a minimum amount of toluene (about 20 ml) required to dissolve the residue at a temperature close to the boiling point of toluene. The lactide was then crystallized from solution by incubating the solution at about 4° C. Recovered crystals were at least about 90% pure, and possibly at least about 95% pure as determined by the melting point of the crystals and HPLC analysis.

The molar conversion of lactic acid to lactide was about 50%. The recovery yield of lactide was about 25%. This example shows that lactide can be crystallized and recovered from toluene at least as well as from diethyl ether. Although in this example, the original toluene solvent was essentially completely removed, it is within the scope of the invention to remove sufficient toluene until a volume is achieved which is appropriate for lactide crystallization.

EXAMPLE 4

In this Example, lactide was formed in a dilute solution containing about 1 wt % L-lactic acid.

About 85% heat stable L-lactic acid (by Pfhanstiehl) was mixed with toluene at a ratio (vol/vol) of lactic acid to toluene of 2:198 in a total volume of 200 ml, giving a feedstream containing about 1 wt % lactic acid. One gram of the catalyst Dowex-50 H+ ion exchange resin was added to the mixture which was heated using a heating mantle as described in Example 2. The reaction was continued for about 24 hours to maximize lactide production, although maximum lactide synthesis was achieved by about 3 to about 6 hours.

The toluene was then removed from the mixture by evaporation using a rotary evaporator, at a temperature of about 40° C. to about 50° C. The dried residue of lactide, lactic acid, and oligomers was dissolved in a minimum amount of toluene (about 4 ml to 5 ml) required to dissolve the residue at a temperature close to the boiling point of toluene. The lactide was then crystallized from solution by incubating the solution at about 4° C. Recovered crystals were at least about 90% pure, and possibly at least about 95% pure as determined by the melting point of the crystals and HPLC analysis.

The molar conversion of lactic acid to lactide was about 50%. The recovery yield of lactide was about 25%. Thus, the conversion of lactic acid to lactide is at least as effective in a solution containing about 1% lactic acid as in a solution containing about 5% lactic acid.

EXAMPLE 5

In this example, lactide was formed in a solution containing about 25 wt % L-lactic acid About 85% heat stable L-lactic acid (by Pfhanstiehl) was mixed with toluene at a ratio (vol/vol) of lactic acid to toluene of 50:150 in a total volume of 200 ml, giving a feedstream containing about 25 wt % lactic acid. One gram of the catalyst Dowex-50 H+ ion exchange resin was added to the mixture which was heated using a heating mantle as described in Example 2. The reaction was continued for about 24 hours to maximize lactide production, although maximum lactide synthesis was achieved by about 3 to about 6 hours.

The toluene was then removed from the mixture by evaporation using a rotary evaporator, at a temperature of about 40° C. to about 50° C. The dried residue of lactide, lactic acid, and oligomers was dissolved in a minimum amount of toluene (about 50 ml) required to dissolve the residue at a temperature close to the boiling point of toluene. The lactide was then crystallized from solution by incubating the solution at about 4° C.

The molar conversion of lactic acid to lactide was about 25%. In this experiment, the crystallization was poor, likely due to the large concentration of oligomers in the sample. This example, in conjunction with Examples 2, 3, and 4, supports the concept that oligomer formation is favored in more concentrated solutions (e.g., about 25% lactic acid), whereas cyclic ester formation is favored in more dilute solutions (e.g., about 1%, or about 5%, lactic acid).

EXAMPLE 6

This Example demonstrated the ability to produce lactide in a benzene solvent.

About 85% heat stable L-lactic acid (by Pfhanstiehl) was mixed with benzene at a ratio (vol/vol) of lactic acid to benzene of 10:190 in a total of 200 ml, giving a feedstream containing about 5 wt % lactic acid. One gram of the catalyst Dowex-50 H+ ion exchange resin was added to the mixture which was heated using a heating mantle. As the temperature of the mixture reached about 69° C. free water was removed from the mixture as an azeotrope with benzene (boiling point of the 8.8% water / 91.2% benzene azeotrope is about 69.25° C.) After most of the free water was removed (within about 20 to about 30 minutes), the temperature of the mixture continued to increase to about 80.2° C. the boiling point of benzene. The mixture was allowed to remain at about 80° C. for about 24 hours to maximize lactide production, although maximum lactide synthesis was achieved by about 3 to about 6 hours.

The benzene solvent was then removed from the mixture by evaporation using a rotary evaporator, at a temperature of about 40° C. to about 50° C. The dried residue of lactide, lactic acid, and oligomers was dissolved in a minimum amount of benzene (about 20 ml) required to dissolve the residue at a temperature close to the boiling point of benzene. The lactide was then crystallized from solution by incubating the solution at about 4° C. Recovered crystals were at least about 90% pure, and possibly at least about 95% pure as determined by the melting point of the crystals and HPLC analysis.

The molar conversion of lactic acid to lactide was about 50%. The recovery yield of lactide was about 25%. This Example indicates that benzene works at least as well as toluene as an azeotropic solvent and crystallization solvent for lactide.

EXAMPLE 7

This Example demonstrated the ability to produce lactide in a xylene solvent.

About 85% heat stable L-lactic acid (by Pfhanstiehl) was mixed with xylene at a ratio (vol/vol) of lactic acid to xylene of 10:190 in a total of 200 ml, giving a feedstream containing about 5 wt % lactic acid. One gram of the catalyst Dowex-50 H+ ion exchange resin was added to the mixture which was heated using a heating mantle. As the temperature of the mixture reached about 94° C. free water was removed from the mixture as an azeotrope with xylene (boiling point of the 40% water / 60% xylene azeotrope is about 94.5° C.). After most of the free water was removed (within about 20 to about 30 minutes), the temperature of the mixture continued to increase to about 139.1° C. the boiling point of xylene. The mixture was allowed to remain at about 139° C. for about 24 hours to maximize lactide production, although maximum lactide synthesis was achieved by about 3 to about 6 hours. During the reaction, the solution turned yellow, possibly due to xylene extracting a pigmented compound from Dowex.

The xylene solvent was then removed from the mixture by evaporation using a rotary evaporator, at a temperature of about 40° C. to about 50° C. The dried residue of lactide, lactic acid, and oligomers was dissolved in a minimum amount of toluene (about 20 ml) required to dissolve the residue at a temperature close to the boiling point of toluene. The lactide was then crystallized from solution by incubating the solution at about 4° C. Recovered crystals were at least about 90% pure, and possibly at least about 95% pure as determined by the melting point of the crystals and HPLC analysis. However, the crystals were light yellow in color.

The molar conversion of lactic acid to lactide was about 50%. The recovery yield of lactide was about 25%. This Example indicates that xylene is an effective solvent in which to obtain a high conversion of lactic acid to lactide but that either the xylene or temperature of the reaction may lead to partial degradation of the catalyst.

In order to remove the yellow color from the lactide crystals, 0.25 grams of the recovered crystals were submitted to sublimation. Specifically, the crystals were dried in a condenser-containing vessel under a vacuum (from about 1 mm to about 10 mm Hg). The bottom of the container was warmed, allowing lactide to vaporize at about 90° C. The vaporized lactide condensed on the condenser, leading to a recovery of 0.16 grams of white lactide crystals.

EXAMPLE 8

Figure 5:
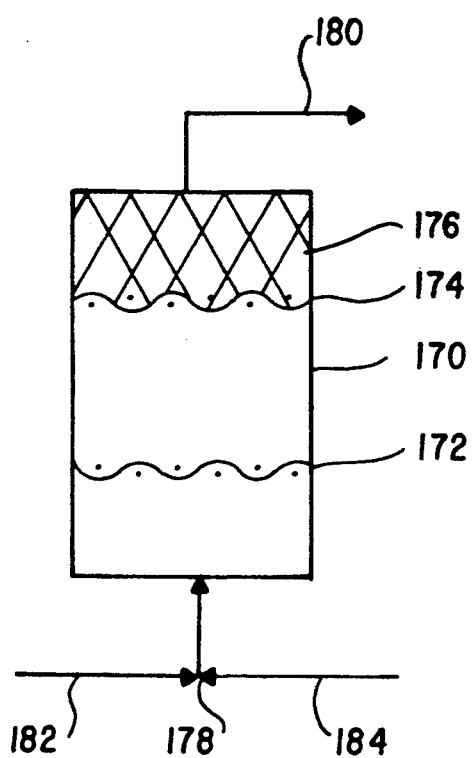
FIG. 5 is a schematic representation of a reactor useful in the method of the invention.

A laboratory scale reactor is set forth schematically in FIG. 5. Reactor 170 is a stainless steel cylinder having a width of about 5 cm and a height of about 31 cm. Reactor 170 was fitted with lower screen 172 which may be a series of screens, and upper screen 174 which also may be more than one screen. Catalyst bed 176 was disposed atop screen 174. The lower empty chamber below screen 174 provided additional time to ensure that the LA feedstock (or LA-containing feedstream) was fully vaporized prior to contact with the catalyst bed. Reactor 170 was fitted with lower tee 178 and upper heated product line 180 for withdrawal of the crude lactide containing vapor. LA feedstock was fed into tee 178 via line 182. Nitrogen carrier gas was fed into tee 178 via line 184. This entire assembly was placed in a sand bath which was heated to maintain the desired reactor temperature. Broadly, the reaction temperature should be greater than about 150° C. and can range up to as high as about 250° C. at about atmospheric pressure. Nominal reaction temperatures around 205° C. were found acceptable. Average residence times of from about 0.5 to about 12 seconds were found to be acceptable.

EXAMPLE 9

The experimental reactor depicted in FIG. 5 was modified so that screen 172 was a 100 mesh screen laid adjacent to a 16 mesh screen and screen 174 was a 45 mesh screen overlaying a 16 mesh screen. Catalyst 176 comprised 10–20, mesh silica gel/alumina catalyst (Akzo-LA-30-5P catalyst). The nitrogen flow rate was adjusted to 1600 ml/min. and it plus the lactic acid feedstock (or feed) were passed through reactor 170 at a superficial vapor velocity of 0.12 ft/sec. The residence time of the contents was 2.8 seconds. Commercial 85% lactic acid (61% $L_1A$, 18% $L_2A$, 5% $L_3A$, 1% $L_4A$ and 15% water) which had been diluted with an additional 11% by weight of water just prior to the run was passed into Tee 178 for admixture with nitrogen at a flow rate of 36.6 ml/hr. The lactide was collected in a dry ice cooled cyclone collector, washed with cold water and filtered. The lactide was dried at ambient temperature in the presence of phosphorous pentoxide. After treatment with diazomethane to convert residual LA species to their methyl esters, the lactide samples were analyzed by gas chromatography. The results recorded are set forth below:

TABLE 2

| Stage (44701-90) | Cumulative Time (hr) | Bed Temp. (°C.) | LA Feed (g) | All* Products (g) | LD Product (g) | LD Yield (mole-%) |
|---|---|---|---|---|---|---|
| Equilibration | 1.8 | 206 | 75.5 | 53.2 | 8.46 | — |
| 1 | 4.8 | 205 | 128.6 | 115.8 | 22.73 | 25.7 |
| 2 | 8.1 | 204 | 141.1 | 130.6 | 28.31 | 30.1 |

*Catalyst weight gain: 21.8 g
Trap contents: 3.8 g
Reactor residue: 1.3 g
Total Material Recovery: 94.6 wt-%

The lower chamber of the reactor was found to be empty and the removed ground catalyst was bone dry. The LD was found to have a purity of 89% at Stage 1 and 92% at Stage 2 and was a white powder. Carbon monoxide production was 2750 ppm after 2.5 hours. This corresponds to 3.3 mole % LA decomposition. The ratio of the LD yield obtained at Stage 2 to the mole % LA decomposed is 7.8:1. The L-LD:meso-LD weight ratio was 51.8:1 for Stage 1 and 34.1:1 for Stage 2.

EXAMPLE 10

The procedure described in connection with Example 9 was repeated using 85% lactic acid feedstock without added water at 32.9 ml/hr and the same nitrogen flow rate to yield a residence time of 3.0 seconds and a superficial velocity of 0.11 ft/sec. The results recorded are set forth below.

TABLE 3

| Stage (44853-9) | Cumulative Time (hr) | Bed Temp. (°C.) | LA Feed (g) | All* Products (g) | LD Product (g) | LD Yield (mole-%) |
|---|---|---|---|---|---|---|
| Equilibration | 1.9 | 205 | 74.4 | 48.9 | — | — |
| 1 | 5.1 | 204 | 123.6 | 106.1 | 31.6 | 25.7 |
| 2 | 8.4 | 204 | 132.0 | 119.0 | 34.0 | 30.1 |
| Post-Run | 9.6 | 202 | — | 8.2 | — | — |

*Catalyst weight gain: 10.6 g
Trap contents: 1.32 g
Reactor residue: 0.81 g
Total Material Recovery: 89.4 wt-%

As the above tabulated data reveals, the lactide yield (34%) obtained in Stage 2 is higher than that obtained in Example 9. Recovered percentages of lactide were found to steadily increase during each stage. The overall recovery of 89.4% of the material fed is lower than the recovery in Example 9. In a duplicate run, the overall recovery of material fed was 94.1%, but lower LD/CO ratios were seen.

The carbon monoxide concentrations were 3200 ppm after 3.2 hours, 2,750 ppm after 5.1 hours and 2800 ppm after 8.0 hours. The average CO concentration between 3.2 and 8 hours of operation corresponds to 3.2 mole % LA decomposition. The ratio of the LD yield obtained during Stage 2 to the mole % LA decomposed is 10.7:1.

The product lactide obtained from Stages 1 and 2 was a white powder. The L-LD:meso-LD weight ratio was 44.0 for Stage 1 and 38.6 for Stage 2.

The filtrate from Stage 1 was extracted with methylene chloride to recover any solubilized lactide which had not yet hydrolyzed. A yellow liquid was obtained from the rotary evaporator (5.4 g) which did not solidify at 52° C. after the methylene chloride was removed.

Upon cooling to room temperature, however, this material solidified to a white crystalline mass which contained a minor amount of yellow liquid. This mixture was washed with cold water to obtain 1.9 g of a white solid which was analyzed and found to contain 87.4% L-lactide and 12.6% meso-lactide.

EXAMPLE 11

This run was conducted in order to determine the efficacy of 5 mm catalyst pellets rather than the 10-20 mesh catalyst used in Example 10. The same conditions used in Example 10 were maintained, except that the 85% lactic acid flow rate was 34.6 ml/hr and the lower 100 mesh screen had been removed. The following results were recorded:

TABLE 4

| Stage (44853-21) | Cumulative Time (hr) | Bed Temp. (°C.) | LA Feed (g) | All* Products (g) | LD Product (g) | LD Yield (mole-%) |
|---|---|---|---|---|---|---|
| Equilibration | 2.0 | 205 | 84.0 | 58.5 | 15.34 | — |
| 1 | 5.2 | 206 | 127.2 | 111.1 | 25.91 | 28.8 |
| 2 | 7.7 | 204 | 108.6 | 87.7 | 20.65 | 26.4 |
| 3 | 11.0 | 220 | 136.8 | 142.6 | 43.49 | 44.6 |
| Post-Run | 11.8 | 217 | — | — | — | — |

*Catalyst weight gain: 18.35 g
Trap contents: 1.99 g
Reactor residue: 0.07 g
Total Material Recovery: 92.0 wt-%

The lactide yields obtained at approximately 205° C. appear to be decreasing with time between Stages 1 and 2. This behavior is opposite to that observed with smaller catalyst particle sizes in Examples 9 and 10 and indicates the potential advantage of reduced catalyst particle size.

Carbon monoxide production was recorded as 6,000 ppm after 1.5 hours, 3,650 ppm after 4.8 hours, 3,550 ppm after 6.3 hours and 9,000 ppm after 10.8 hours. The carbon monoxide concentration, then, appeared to decrease after the equilibration stage to a fairly constant value at the nominal 205° C. bed temperature. The calculated mole % LA decomposed was 3.9% during Stages 1 and 2. The ratio of the LD yield obtained during Stage 2 to the mole % lactic acid decomposed was 6.7:1.

After 7.7 hours of operation at approximately 205° C., the temperature of the catalyst bed was raised to approximately 220° C. and maintained at this temperature for 3.3 hours. The total weight of material collected over this time was 104% of the material fed during this same time period. Similarly, the LD yield of 44.6% observed for this time period is inflated by the fact that part of the LD collected probably originated from the earlier part of the run conducted at 205° C., i.e., lactide produced from residual material deposited on the catalyst bed earlier. However, the apparent increased lactide yield obtained at this temperature is balanced by the increased carbon monoxide production, which is evidence of lactic acid decomposition. The L-LD:meso-LD weight ratio was approximately 42 for Stages 1 and 2, but only 25.3 for Stage 3.

After the run was completed, partial clogging of the lower 16 mesh screen was noted. Complete hydrolysis / vaporization apparently was achieved because the removed catalyst bed was found to be bone dry. This clogging probably occurred during cool-down since the gaseous back-pressure did not increase during the entire run.

EXAMPLE 12

The reactor was filled with alternating layers of 3 mm glass beads and the silica alumina catalyst described in Example 9 as follows: glass 125 ml; catalyst 23 ml; glass 160 ml; catalyst 22 ml; glass 70 ml; catalyst 22 ml and glass 70 ml, from top to bottom. The 85% lactic acid feedstock was passed into the reactor at a rate of 16.5 ml/hr with a nitrogen sweep of 800 ml/min. which establishes a residence time of about 2.7 sec in the catalyst bed and a superficial velocity of 0.04 ft/sec. The reactor temperature was maintained at 203°±3° C. The product was washed with cold water and the precipitated lactide filtered therefrom. The lactide then was dried by slight heating under vacuum in the presence of $P_2O_5$. The filtrate was collected and subjected to distillation to remove sufficient water to re-establish a lactic acid concentration similar to the original 85% lactic acid feed. This distilled filtrate was then combined with make-up 85% lactic acid and recycled to the reactor. This sequence was repeated for 3 reaction stages; however, the start-up stage suffered from equipment leaks so that it was excluded from calculations.

In total, 537.7 g of aqueous lactic acid was fed and 512.9 g of product was collected for a 95.4% mass recovery. This recovery includes 17.3 g material deposited on the lower layer of glass beads which was analyzed and found to be primarily $L_3A$.

The lactide yield was about 78% (when correcting for the material on the glass beads). The L-lactide:meso-lactide weight ratio was found to be about 95:5 for the composite lactide product. The washed LD was about 98% pure and contained less than about 2% $L_2A$. The D-lactide concentration was found to be below the detection limit in the LD product isolated from the last recycle.

This example illustrates the ability to significantly improve yields of lactide by a recycle process while avoiding significant increases in LD racemization.

EXAMPLE 13

In this run, 85% lactic acid (39.3 ml/hr) was passed into the reactor which contained a bed of Amberlyst-15 acid ion-exchange resin held at a nominal bed temperature of 215° C. The nitrogen flow rate was 1580 ml/min, the residence time was 2.9 seconds, the lactic acid feedstock constituted 26.3 wt % of the total feed, and the superficial velocity through the reactor (screen assembly of Example 11) was approximately 0.11 ft/sec. The results recorded are set forth below:

TABLE 5

| Stage (44934-25) | Cumulative Time (hr) | LA Feed (g) | All Products (g) | Crude LD (g) | LD Yield (mole-%) | CO Yield (mole-%) |
| --- | --- | --- | --- | --- | --- | --- |
| Equilibration | 1.7 | 74.4 | 36.5 | none | 0 | — |
| 1 | 3.7 | 92.4 | 46.9 | none | 0 | 95 |
| 2 | 5.7 | 84.0 | 28.3 | trace | — | 95 |

This strongly acidic ion-exchange resin gave negligible lactide and almost quantitative decomposition of lactic acid to carbon monoxide (and presumably acetaldehyde). The catalyst bed initially had a very large exotherm (25° C.). These results are consistent with the results obtained using another Bronsted catalyst (phosphoric acid on Kieselguhr) which showed almost no tendency to generate lactide from lactic acid.

EXAMPLE 14

EXAMPLE 15

In this example, 85% lactic acid (36.7 ml/hr) was fed to the reactor having the screen assembly of Example 11 and containing 10–20 mesh gamma alumina/silica (93:7, respectively) held at a nominal bed temperature of 205° C. The nitrogen flow rate was 1596 ml/min, the residence time was 3 seconds, wt % organic in the feedstock was 25% and the superficial velocity was about 0.11 ft/sec. The following results were recorded:

TABLE 7

| Stage (44934-46) | Cumulative Time (hr) | LA Feed (g) | All Products (g) | Crude LD (g) | LD Purity (wt-%) | L-LD m-LD | LD Yield (mole-%) | CO Yield (mole-%) | LD Yield/ CO Yield |
| --- | --- | --- | --- | --- | --- | --- | --- | --- | --- |
| Equilibration | 1.5 | 67.2 | 32.2 | 6.37 | | | | | |
| 1 | 4.0 | 108.0 | 90.4 | 23.74 | 100 | 23.1 | 32.0 | 2.78 | 11.53 |
| 2 | 6.5 | 105.6 | 92.7 | 18.76 | 100 | 44.9 | 26.0 | 1.74 | 14.9 |
| Post-run | 7.5 | — | 7.3 | | | | | | |
| | | 280.8 | 222.6 | | | | | | |

Catalyst weight gain: 33.93 g (33.0%)
Trap Contents: 2.10 g
Reactor residue: L$_n$A in lower T-joint (not weighed)
Total material % recovery: (258.6/280.8) (100) = 92.1%
Carbon Monoxide: 2700 ppm after 3.0 hours
1700 ppm after 5.4 hours In this run, 85% lactic acid (36.8 ml/hr) was fed to a reactor containing 10–12% molybdenum (VI) oxide on gamma alumina (10–20 mesh) held at a nominal bed temperature of 203° C. A nitrogen flow rate of 1580 ml/min, a residence time of 3.0 seconds, a wt % organics in the feedstock of 25.2 wt % and a superficial velocity of 0.11 ft/sec were maintained in the run. The results recorded are set forth below:

The initial 15° C. exotherm decreased and the reaction was 2° C. endothermic at the end run. Even though the LD yield dropped during Stage 2, a significant drop in CO resulted in a high LD/CO ratio.

EXAMPLE 16

In this run which utilized a reactor having only a lower 16 mesh screen and an upper 42 mesh screen,

TABLE 6

| Stage (44934-38) | Cumulative Time (hr) | LA Feed (g) | All Products (g) | Crude LD (g) | LD Purity (wt-%) | L-LD m-LD | LD Yield (mole-%) | CO Yield (mole-%) | LD Yield/ CO Yield |
| --- | --- | --- | --- | --- | --- | --- | --- | --- | --- |
| Equilibration | 1.5 | 66.0 | 45.5 | 6.4 | | | | | |
| 1 | 4.0 | 120.0 | 95.3 | 19.8 | 96.5 | 37.6 | 22.6 | 3.6 | 6.3 |
| 2 | 6.0 | 87.6 | 76.4 | 15.87 | 92.9 | 37.7 | 23.5 | 3.6 | 6.5 |
| Post-run | 7.0 | — | 6.3 | | | | | | |
| | | 273.6 | 222.5 | | | | | | |

Catalyst weight gain: 12.6 g (8.6%)
Trap Contents: 7.63 g
Reactor residue: Lactic acid inlet tube filled with L$_n$A after cool down
Total material % recovery: (242.8/273.6) (100) = 88.8%
Carbon Monoxide: 3,500 ppm after 3.0 hours
3,500 ppm after 5.5 hours The initial exotherm of 9° C. decreased to 1° C. at the end of the run. The observed lactide yields and LD/CO ratios were lower than observed for the silica/alumina catalyst reported above.

85% lactic acid (35.0 ml/hr) was passed through a reactor containing 10–20 mesh of 99% gamma alumina (Alfa, 90 m$^2$g) held at a nominal bed temperature of 204° C. In this run, the nitrogen flow was 1580 ml/min, the residence time was 3.03 seconds, the wt % organic in the feedstock was 24.3%, and the superficial velocity again was approximately 0.11 ft/sec. The following results were recorded:

TABLE 8

| Stage (45022-2) | Cumulative Time (hr) | LA Feed (g) | All Products (g) | Crude LD (g) | LD Purity (wt-%) | L-LD m-LD | LD Yield (mole-%) | CO Yield (mole-%) | LD Yield/ CO Yield |
|---|---|---|---|---|---|---|---|---|---|
| Equilibration | 1.5 | 62.4 | 37.52 | 9.54 | | | | | |
| 1 | 4.0 | 104.4 | 89.55 | 22.87 | 97.6 | 31.5 | 30.4 | 0.32 | 94.4 |
| 2 | 6.5 | 105.6 | 91.93 | 22.39 | 98.7 | 46.0 | 29.7 | 0.42 | 70.0 |
| Post-run | 7.5 | — | 7.99 | | | | | | |
| | | 272.4 | 227.0 | | | | | | |

Trap Contents: 5.92 g
Catalyst weight gain: 23.88 g (18.3%)
Residue drilled from lower feed lines: 1.66 g Stages 1 and 2 filtrates were extracted with methylene chloride within one hour after formation to yield the following quantities of lactide:

TABLE 9

| Sample | Sample wt., (g) | LD Purity (wt-%) | L-LD/ m-LD | LD Yield (mole-%) | Total LD Yield (mole-%) | Overall LD Composition | |
|---|---|---|---|---|---|---|---|
| | | | | | | % L-LD | % m-LD |
| Stage 1 extract. | 2.74 | 91.8 | 5.11 | 3.7 | 34.1 | 95.5 | 4.5 |
| Stage 2 extract. | 3.55 | 92.5 | 4.06 | 4.4 | 34.1 | 95.6 | 4.4 |

Carbon monoxide:
300 ppm after 3.0 hours
400 ppm after 5.7 hours

The initial exotherm of 12° C. reduced to 1° C. after 2.5 hours and was absence after 5 hours. This catalyst serves to distinguish the relative effect of molybdenum (VI) oxide versus alumina in Example 14. Of importance are the relatively high lactide yields that there were obtained and especially the high LD/CO ratios that were one order of magnitude higher than previously observed with any other catalyst. These results and those of Example 15 indicate that small silica quantities significantly decrease the LD/CO ratio when using alumina/silica catalysts. Alumina catalyst alone appears to be a superior catalyst compared to alumina/silica mixtures.

The filtrates from Stages 1 and 2 were extracted with methylene chloride soon after the lactide washing procedures were completed to recover the lactide remaining in solution. The total lactide yields (obtained from initial washing/filtration followed by filtrate extraction) from both stages is the same (34.1%) and the overall L-LD:meso-LD ratios are the same (95.4:4.5 for Stage 1 plus extract and 95.6:4.4 for Stage 2 plus extract).

EXAMPLE 17

In this example, using the reactor configuration of Example 16, 85% lactic acid (35.5 ml/hr) was passed through the reactor containing 3 mm borosilicate glass beads (washed with water and acetone) held at a nominal bed temperature of 203° C. During this run, the nitrogen flow rate was 1580 ml/min, the residence time was 1.15 seconds within the void volume in the glass beads, the wt % organics in the feedstock was 20.44%, and the superficial velocity was approximately 0.11 ft/sec. The following results were recorded:

TABLE 10

| Stage (44934-73) | Cumulative Time (hr) | LA Feed (g) | All Products (g) | Crude LD (g) | LD Purity (wt-%) | L-LD m-LD | LD Yield (mole-%) | CO Yield (mole-%) | LD Yield/ CO Yield |
|---|---|---|---|---|---|---|---|---|---|
| Equilibration | 1.0 | 44.4 | 35.94 | 1.83 | | | | | |
| 1 | 3.0 | 87.6 | 71.97 | 5.72 | 96.4 | 240 | 8.9 | ≦.01 | ≧890.0 |
| 2 | 5.5 | 100.8 | 91.16 | 10.36 | 97.5 | 190 | 14.2 | 0.021 | 670.0 |
| Post-run | 7.2 | | 13.03 | | | | | | |
| | | 232.8 | 212.1 | | | | | | |

Some glass beads were adhering to reactor walls and were washed free with acetone.
Most beads had a tacky feel. Bead weight gain (after washing): 0.15 g
Trap Contents: 13.94 g
L$_n$A which clogged lactic acid feed line and lower fittings after cool down was not weighed.
Total material % recover = (226.04/232.8) (100) > 97.1%
Carbon Monoxide:
<10 ppm after 2.1 hours
20 ppm after 4.1 hours The approximately 2° C. endotherm was present during the entire run. Some beads had a tacky coating indicating that lactic acid oligomerization was occurring on the glass surfaces.

The use of glass beads without any catalyst resulted in lower LD yields, though much higher L-LD:meso-LD ratios and LD/CO ratios compared to other catalysts tested.

EXAMPLE 18

In this example, 85% lactic acid (35.1 ml/hr) was passed through an empty reactor (no glass beads or catalyst) maintained at a temperature of about 201° C. During this run, the nitrogen flow was 1540 ml/sec, the residence time was 10.4 seconds, the wt % organic in feedstock was 24.8%, and the superficial velocity was about 0.11 ft/sec. No equlibration period was used in this experiment. The following results were recorded:

TABLE 11

| Stage (44934-38) | Cumulative Time (hr) | LA Feed (g) | All Products (g) | Crude LD (g) | LD Purity (wt-%) | L-LD m-LD | LD Yield (mole-%) | CO Yield (mole-%) | LD Yield/ CO Yield |
|---|---|---|---|---|---|---|---|---|---|
| One collector used for entire run | 4 | 129.6 | 111.3 | 13.08 | 74.7 | 154 | 11.0 | <0.01 | >1100 |

Trap contents were not weighed
$L_nA$ which clogged the lower T-joint and lactic acid feed line after shut-down was not weighed. Therefore, total material % recovery >85.9%
Carbon Monoxide: 10 ppm after 2.5 hours There was no exotherm evident during this run. Lactide yields are approximately the same as reported for the glass bead run of Example 17, but the LD/CO ratio was substantially increased. The low lactide purity of 74.5% resulted due to using a lower than normal proportion of cold wash water due to the relatively small amount of lactide obtained.

Importantly, however, is the demonstration that aqueous LA can be converted to LD using no catalyst or solid packing material in the reactor providing that the LD feedstock is maintained in the vapor phase at elevated temperature. While LD yields are low, essentially for LD formation over by-product formation (as measured by the very high LD/CO ratio) and lack of LD racemization (as measured by the high L-LD:meso-LD ratio) appears to be maximized. The effect of a catalyst, such as alumina, is to improve LD yields, though at the expense of also increasing CO by-product formation and LD racemization. Silica gel and other catalysts also improve LD yields, though they may increase CO by-product formation to a greater extent. LD yield maximization or LD selective conversion maximization and control of LD racemization can be obtained by selection of the presence and type of catalyst and temperature.

EXAMPLE 18

This run replicates the empty reactor run in Example 18, except using the reactor screen configuration of Example 16. In this run, 85% lactic acid (34.0 ml/hr) was fed to the empty reactor maintained at about 204° C. The nitrogen flow rate was 1580 ml/sec, the residence time was 10.2 seconds, the wt % organics in feedstock was 23.7%, and the superficial velocity was approximately 0.11 ft/sec. The following results were recorded:

Stage 2 yielded an additional 2.47 g solid which analyzed as 90.5% by weight LD. This extra increment of LD increases the total LD yield to 15.5% for this stage. The precursor of the LD is presumed to be mainly $L_2A$ in the aqueous lactic acid feed which cyclizes and readily vaporizes (or vaporizes/cyclizes) under the reaction conditions. The extra lactide produced when catalysts are employed is presumed to originate from vaporized $L_1A$ which is converted in the chemisorbed state to chemisorbed $L_2A$ which is converted into LD on the catalyst surface. Due to the high vapor pressure of LD compared to that of $L_2A$, the LD formed on the catalyst surface is rapidly and selectively removed by the heated carrier gas.

The very high L-LD:meso-LD ratios are approximate values since the meso:LD concentration fell below the concentration range used for calibration purposes. However, these L-LD:meso-LD ratios indicate that little or no racemization occurred in this run since the low meso percentages are in the range predicted from the reaction of the approximately 0.3% $D-L_1A$ which is present in commercial 85% $L-L_1A$. The L-LD:meso-LD ratio of extracted Stage 2 was found to be approximately 285:1 which indicates that the meso concentration is so low that little selective solubilization of meso-lactide occurs.

These results further indicate that LD can be made without catalyst in high overall yield, if $L_1A$ recycle is employed. Furthermore, LD can be made without catalyst with almost complete retention of configuration of the aqueous lactic acid from which it is derived.

When the reactor was disassembled after termination of the run it was found to be essentially empty. The fact that 3.98 g material volatilized during the past run stage indicates that this quantity of material probably represents a steady state volume of LA within the reactor

TABLE 12

| Stage (44934-92) | Cumulative Time (hr) | LA Feed (g) | All Products (g) | Crude LD (g) | LD Purity (wt-%) | L-LD m-LD | LD Yield (mole-%) | CO Yield (mole-%) | LD Yield/ CO Yield |
|---|---|---|---|---|---|---|---|---|---|
| Equilibration | 1.0 | 40.8 | 38.83 | 1.07 | | | | | |
| 1 | 3.0 | 84.0 | 70.78 | 5.92 | 97.3 | 280 | 9.7 | <0.001 | >880.0 |
| 2 | 6.0 | 120.0 | 104.05 | 10.89 | 100+ | 206 | 12.9 | <0.001 | >1170.0 |
| Post-run | 7.0 | — | 3.98 | | | | | | |
| | | 244.8 | 217.6 | | | | | | |

Trap Contents: 16.88 g
Entire lactic acid feed line was plugged with $L_nA$ after run. Estimated weight: 8.0 g
The lower T-joint had a small amount of oligomeric $L_nA$.
Total material % recovery (242.5/244.8) 100 > 99.1%
Stage 2 filtrate (after approximately 18 hours at −5° C.) was extracted with methylene chloride to given 2.47 g white solid which was anlayzed and shown to be 90.5% lactide with a L-LD/meso-LD ratio of 285. This constitutes an extra 2.6% lactide yield to give a total lactide yield of 15.5% from fraction 2.
Carbon Monoxide:
<10 ppm after 2.2 hours
<10 ppm after 4.7 hours Again, no exotherm was observed. These results again show very high LD/CO and L-LD:meso-LD ratios as in Example 18, but also show increasing lactide yield with time. Extraction of the filtrate obtained from during continuous operation. During this run, 244.8 g lactic acid had been fed. The fact that this relatively small quantity of material was readily transferred to the collector during the post-run indicates that 85 percent lactic acid and this material is readily volatilized under the reactor operating conditions.

EXAMPLE 20

A three-neck, one-liter round-bottom flask was fitted with a mechanical stirrer, nitrogen sparger, and a straight distillation take-off to a condenser, and the receiver to a vacuum take-off and manometer. The flask was charged with 650 ml (770.4 g) of commercial 85% L-lactic acid feed and heated at 120° C. to 130° C. with stirring and nitrogen bubbling. Water was initially distilled using a water aspirator and a vacuum pump was used for pressures of 30 torr and below. Aliquots were removed during the course of the heating and characterized by titration for DP. Then, after methylation with diazomethane, the aliquots were characterized by gas chromatography (GC) for percentages of $L_1A$, $L_2A$, $L_3A$, $L_4A$, and LD. The results recorded are set forth below in Table 13.

TABLE 13

| DP(a) | Composition wt-%(b) | | | | | Distillation | |
|---|---|---|---|---|---|---|---|
| | $L_1A$ | $L_2A$ | $L_3A$ | $L_4A$ | LD | (°C.) | (torr) |
| 1.29(C) | 75.4 | 20.1 | 3.3 | 0.3 | 1.3 | | |
| 1.44 | 49.0 | 28.5 | 11.5 | 2.2 | 3.3 | 120–130 | 400–210 |
| 1.59 | 27.8 | 27.8 | 20.2 | 10.3 | 8.6 | 150 | 90 |
| 1.99 | 11.8 | 16.7 | 14.4 | 8.8 | 18.4 | 155 | 153 |
| 2.01 | 12.3 | 14.0 | 13.8 | 9.8 | 19.0 | 160 | 85 |
| 2.07 | 8.3 | 6.0 | 15.0 | 15.0 | 27.9 | 175 | 30 |
| 2.63 | 2.1 | 0.7 | 1.0 | 0.8 | 14.7 | 185(d) | 30(d) |
| 24.0 | 0.4 | 1.4 | 0.6 | 0.4 | 11.5 | 185(d) | 10(d) |

(a) Titration with KOH.
(b) Gas chromatography of methyl esters.
(c) L-lactic acid feed.
(d) Prolonged (overnight) distillation.

As the above-tabulated data reveals, LD production peaked at a DP of about 2. This peak LD production was achieved under relatively mild distillation conditions in a facile manner. If the flask contents are further dehydrated to higher DPs, LD eventually will begin to distill.

EXAMPLE 21

A reservoir of lactic acid with a DP of about 2 (as determined by HPLC) was prepared for further distillation experiments via the distillation that is described in Table 14. This provides a common starting point from which distillation parameters can be changed in a systematic manner.

As shown in Table 15, a high temperature of about 200° C. was chosen because it is expected to favor ring closure to produce lactide over competing oligomerization reactions due to the higher activation energy expected for ring closure. A general distillation nomograph was used to convert the conditions of 175° C. and 30 mm (described in Table 13 to obtain LD in solution at DP 2.07) to the pressure required at 200° C. to again boil this mixture (about 85 mm).

In this experiment, any lactide coating the condenser and the distillation head were combined with the material in the collector flask and analyzed for lactide and other components as a mixed sample.

The results in Table 15 indicate that the lactide concentration in the liquid phase rapidly peaked at 7.5% (HPLC DP of 2.54–3.54) in the liquid phase and then decreased as the distillation was continued.

Under the employed conditions, approximately 60% of the formed lactide distilled within the first 30 minutes, rather than remain in the reaction pot. The rapid increase in DP is also probably related to the increased lactide produced which also underwent rapid reactions with $L_nA$ species to form $L_{n+2}A$ species.

The total lactide collected in the distillate and deposited on the condenser during this distillation was approximately 36.7 g. Almost all of this lactide appeared to be formed during the first 30 minutes of the distillation during which time approximately 40 ml of distillate was collected. This observation indicates that lactide of moderately high purity was being distilled.

The results indicate that substantial amounts of lactide can be produced under these conditions. The total lactide produced by distillation (36.7 g) and also existing in the pot after generation of Sample 46051-21-27 (approximately 24 g) is approximately 61 g. This quantity of lactide corresponds to approximately 19% of the lactide theoretical yield from Sample 46051-15-14. This amount compares favorably with the results that are reported in Example 20.

TABLE 14

SHORT PATH DISTILLATION (NO. 4) OF 1537 g 85 PERCENT LACTIC ACID

| Sample Number | Oil Bath Temp., C. | Pot Temp., C. | Pressure, mm | Weight Distilled, g | Elapsed Time, min. | Nitrogen Sparge Rate | | DP, Titration | DP, HPLC | Percent $H_2O$ |
|---|---|---|---|---|---|---|---|---|---|---|
| | | | | | | Gauge Pressure, mm | Nitrogen Flow, cc/min | | | |
| 46051-14-2 | 80–117 | 23–102 | 117–116 | 201.8 | 105 | 115–105 | ~8 | — | — | — |
| 46051-14-22(a) | 117–139 | 102–136 | 100–90 | 92.5 | 180 | 120–90 | ~8 | 1.62 | — | — |
| 46051-15-14(b) | 135 | 27–135 | 89–91 | 31.4 | 260 | 95–90 | ~8 | 1.85 | 2.07 | 1.21 |

| Sample Number | GC/HPLC Results, percent | | | | | | | | | |
|---|---|---|---|---|---|---|---|---|---|---|
| | L-LD | LA | $L_2A$ | $L_3A$ | $L_4A$ | $L_5A$ | $L_6A$ | $L_7A$ | $L_8A$ | Total |
| 46051-14-2 | — | — | — | — | — | — | — | — | — | — |
| 46051-14-22(a) | — | — | — | — | — | — | — | — | — | — |
| 46051-15-14(b) | 3.61 | 19.65 | 21.75 | 18.93 | 8.57 | 0.20 | 0 | 0 | 0 | 73.92 |
| | 3.4 | 25.2 | 21.8 | 24.4 | 14.3 | 8.0 | 3.6 | 1.9 | 1.0 | 104.8 |

(a)Distillation was stopped and pot contents were frozen in dry ice. After DP determination was performed, distillation was continued to obtain Sample 46051-15-14.
(b)4.53 g material was present in trap after distillation was complete. Sample 46051-15-14, which weighed 1207 g, was frozen in 3 polyethylene bottles at −60 C. until used in further distillations.
When water was not determined, the analyte summation is only for those species which were specifically determined. Some rounding-off errors of the general magnitude of 0.1 percent may exist in the tables for analyte summations.

TABLE 15

SHORT PATH DISTILLATION (NO. 4B) OF 364.4 g OF SAMPLE 46051-15-14

| Sample Number | Oil Bath Temp., C. | Pot Temp., C. | Head Temp., C. | Pressure, mm | Volume/ Weight Distilled | Elapsed Time, min. | Nitrogen Sparge | DP, Titration | DP, HPLC | Percent $H_2O$ |
|---|---|---|---|---|---|---|---|---|---|---|
| 46051-15-14 | — | — | 27 | — | — | 0 | — | 1.85 | 2.07 | 1.21 |
| 46051-21-22 | 185–195 | 85–179 | 120 | 85 | ~30 ml (solid) | 15 | none | 2.13 | 2.54[a] | 0.36 |
| 46051-21-27 | 195–199 | 182–190 | 80 | 85 | ~10 ml (solid) | 30 | none | 2.44 | 3.54 | 0.51 |
| 46051-21-31 | 199–199 | 191–193 | 59 | 85 | — | 45 | none | 2.57 | 4.18 | 0.38 |
| 46051-22-4 | 199 | 193–194 | 57 | 85 | — | 60 | none | — | 4.39 | 0.30 |
| 46051-22-11 | 200–201 | 194–195 | 70 | 85 | - | 90 | none | — | 4.93 | 0.11 |
| 46051-22-20 | 200 | 195 | 50 | 85 | 97.25 g (total) | 120 | none | — | >5.16 | — |

| Sample Number | LIQUID PHASE GC/HPLC Results, percent | | | | | | | | | | | | | | |
|---|---|---|---|---|---|---|---|---|---|---|---|---|---|---|---|
| | L-LD | LA | $L_2A$ | $L_3A$ | $L_4A$ | $L_5A$ | $L_6A$ | $L_7A$ | $L_8A$ | $L_9A$ | $L_{10}A$ | $L_{11}A$ | $L_{12}A$ | $L_{13}A$ | $L_{14}A$ | Total |
| 46051-15-14 | 3.61 | 19.65 | 21.75 | 18.93 | 8.57 | 0.20 | 0 | 0 | 0 | 0 | 0 | 0 | 0 | 0 | 0 | 73.92 |
| | 3.4 | 25.2 | 21.8 | 24.4 | 14.3 | 8.0 | 3.6 | 1.9 | 1.0 | 0 | 0 | 0 | 0 | 0 | 0 | 104.8 |
| 46051-21-22 | 9.71 | 8.85 | 11.25 | 20.52 | 14.30 | 3.43 | 0 | 0 | 0 | 0 | 0 | 0 | 0 | 0 | 0 | 68.4 |
| | 7.5 | 12.0 | 10.2 | 23.0 | 17.1 | (b) | 7.1 | 4.7 | 2.6 | 1.6 | 0.9 | 0 | 0 | 0 | 0 | — |
| 46051-21-27 | 11.32 | 2.20 | 3.10 | 15.52 | 13.35 | 6.87 | 0 | 0 | 0 | 0 | 0 | 0 | 0 | 0 | 0 | 52.9 |
| | 7.5 | 5.9 | 4.1 | 17.9 | 15.6 | 13.8 | 10.8 | 7.9 | 5.6 | 4.2 | 3.0 | 2.5 | 1.5 | 0 | 0 | 100.8 |
| 46051-21-31 | 10.95 | 0.99 | 1.14 | 10.43 | 9.93 | 6.84 | 0 | 0 | 0 | 0 | 0 | 0 | 0 | 0 | 0 | 40.7 |
| | 6.3 | 3.1 | 2.6 | 12.6 | 11.9 | 12.2 | 10.3 | 8.2 | 6.7 | 5.6 | 5.1 | 3.4 | 3.1 | 1.8 | 0 | 93.3 |
| 46051-22-4 | 9.64 | 0.43 | 0.12 | 6.39 | 6.89 | 5.82 | 0 | 0 | 0 | 0 | 0 | 0 | 0 | 0 | 0 | 29.5 |
| | 5.3 | 3.3 | 1.6 | 8.3 | 8.4 | 9.5 | 8.6 | 7.8 | 6.8 | 5.9 | 5.6 | 4.1 | 3.6 | 2.5 | 0 | 81.6 |
| 46051-22-11 | 5.94 | 0 | 0 | 2.63 | 4.22 | 4.05 | 0 | 0 | 0 | 0 | 0 | 0 | 0 | 0 | 0 | 17.0 |
| | 3.7 | 1.9 | 0.9 | 5.1 | 5.8 | 7.0 | 6.5 | 6.3 | 5.9 | 5.4 | 5.3 | 4.2 | 3.8 | 3.6 | 0 | 65.4 |
| 46051-22-20 | — | — | — | — | — | — | — | — | — | — | — | — | — | — | — | — |
| | 2.2 | 1.9 | 0.6 | 2.6 | 3.4 | 4.3 | 4.5 | 4.4 | 4.5 | 4.3 | 3.4 | 3.7 | 3.7 | 4.1 | 0 | 47.7 |

(a) Value calculated using $L_5A$ percentage = 0.
(b) $L_5A$ peak obscured and distorted by "air" peak.
Distillate analysis: L-LD (32.42 percent), $L_1A$ (45.26 percent), $L_2A$ (5.34 percent); total lactide: (97.25 g) (0.377) = 36.7 g LD in distillate.
When water was not determined, the analyte summation is only for those species which were specifically determined. Some rounding-off errors of general magnitude of 0.1 percent may exist in the tables for analyte summations.

EXAMPLES 22–31

A pot was connected to a distillation head and cooled receiver, feed funnel, and manistat for maintaining a pressure of about 50–60 torr. Aliquots of the various DP materials of Example 20 were incrementally distilled by adding them dropwise from the heated funnel (145° C.) to the pot under rapid stirring. The pot temperature of the melt was monitored by an internal thermocouple and the pot was heated by an external oil bath. The pot temperature was varied and the distillation rates noted. The amount of material that distills rapidly, i.e. several drops per second, was weighed and compared to the amount remaining in the pot. The distillations generally were marked by rapid distillations at the beginning of each run, slowly eventually to approximately 1/5 the initial rate, i.e. 1 drop per 2–3 seconds. The results are recorded in the following tables. DPs were determined by titration.

TABLE 16

| Example | DP(a) | Amount(b) Distilled/Not Distilled (wt-%) | Distillation(c) Temperature (°C.) | Distillation Rate |
|---|---|---|---|---|
| 22 | 1.29 | 67/16 | 200 | rapid |
| 23 | 1.44 | 49/42 | 193 | rapid |
| 24 | 1.59 | 39/58 | 220 | rapid |
| 25 | 1.99 | 52/48 | 197 | slow |
| 26 | 1.99 | 54/46 | 225 | rapid |
| 27 | 1.99 | 43/65 | 215 | slow |
| 28 | 2.07 | 15/76 | 202 | moderate |
| 29 | 2.63 | trace distilled | 204 | very slow |

TABLE 16-continued

| Example | DP(a) | Amount(b) Distilled/Not Distilled (wt-%) | Distillation(c) Temperature (°C.) | Distillation Rate |
|---|---|---|---|---|
| 30 | 2.63 | 8/85 | 227 | very slow |
| 31 | 24.0 | trace distilled | 204 | very slow |

(a) By titration
(b) As wt % of starting material
(c) 50–60 torr.

TABLE 17

| Example | DP(a) | Starting Material | L-LD(b) (wt-%) Distillate | Pot |
|---|---|---|---|---|
| 22 | 1.29 | 1.3 | 1.1 | 18.5 |
| 23 | 1.44 | 3.3 | 1.4 | 25.5 |
| 24 | 1.59 | 8.6 | 18.8 | 26.1 |
| 26 | 1.99 | 18.4 | 43.5 | 13.2 |
| 28 | 2.07 | 27.9 | 35.2 | 24.7 |
| 29 | 2.63 | 14.7 | 12.7 | 7.1 |
| 31 | 24.0 | 11.5 | trace | 5.8 |

(a) Degree of polymerization of starting material, by titration.
(b) Composition of GC analyses after methylation with diazomethane.

The results depicted at Table 16 show that progressively higher temperatures are required to distill LD as the DP and the melt viscosity increase. The amount of material that distills rapidly increases at lower DP, however, the best yield and purity was found at approximately a DP of 2 as measured by titration. This is seen by comparing the data of Table 16 to that of Table 17 where the products were assayed. These examples demonstrate that LD can be distilled rapidly from lower DP materials and that this rate is much faster than the prior art cracking of oligomers having higher DPs of 5 and above. The best enrichment of LD occurs at approximately a DP of 2 were it also distills rapidly. Since the amount of LD after distillation exceeds the amount of LD before distillation, LD is formed during distillation, probably by a ring-closure mechanism.

EXAMPLES 32-34

The runs of Examples 28, 30, and 31 were repeated, except that 1wt-% stannous octoate catalyst was added to the starting material. The results recorded are set forth below.

TABLE 18

| Example | DP(a) | Catalyst,(b) With/Without | Distilled(c) (wt-%) | Distillation Rate |
|---|---|---|---|---|
| 28 | 2.07 | without | 15 | moderate |
| 32 | 2.07 | with | 17 | rapid |
| 30 | 2.63 | without | 8 | very slow |
| 33 | 2.63 | with | 48 | moderate |
| 31 | 24 | without | trace | very slow |
| 34 | 24 | with | 5 | very slow |

(a) By titration
(b) 1% stannous octoate
(c) As wt % of starting material.

The rate of distillation of lactide was accelerated by use of the catalyst only when the DP was greater than 2 (measured by titration) according to the above-tabulated data. This is understandable in terms of the probable chemical mechanisms involved. Stannous octoate is believed to operate by cleaving higher DP oligomeric lactic acids into smaller fragments that form lactide and is, therefore, effective in this DP regime. At a DP of about 2, the mechanism probably primarily is a rapid ring closure without catalyst, which has little discernable effect on distillation rates at this DP. Accordingly, conventional catalysts are superfluous to the liquid phase lactide production process of the invention.

EXAMPLE 35

A bench apparatus was used to demonstrate a unit operation for the continuous addition of a DP 2.02 (as measured by titration) lactic acid feed to a distillation column for forming, distilling, and purifying product LD. The column heat was supplied by reboiler fluid that refluxes up to a 5-plate Oldershaw column. The feed was fed to the top of the column where LD codistills with the reboiler vapor. Further LD forms as the feed percolates down through the column. Higher $L_nA$ oligomers (n greater than 3) eventually find their way to the still bottom. Water is removed through a hot condenser which rejects any lactic acid, returning the latter to the column. The port through which LD is distilled is positioned below that from which water is removed. LD is collected in a cooled fraction collector.

The reboiler fluid used was an alkyl benzene (AB) where the alkyl moiety is a mixture of $C_{11}$-$C_{14}$ isomers. The alkyl benzene had a boiling range of 220°-230° C. at 56 torr after a small forecut was taken off. The alkyl benzene is totally immiscible, hot or cold, with LD or $L_nA$. The heat flux was maintained such that the alkyl benzene is distilled as the feed is added dropwise at a rate of approximately 17-75 g/hr.

Approximately 3-4 parts by weight of crude LD distill per part of alkyl benzene. Alkyl benzene alone distills at 215°-220° C. at 58 torr, whereas, under the same conditions LD distills at 189° C. Alkyl benzene and lactide codistill at 165°-177° C. at 56 torr. The feed DP2 material was heated to approximately 80°-120° C. and delivered via a small teflon tube to the system. The feed is pulled into the system by vacuum or by pumping using a peristaltic pump. The rate was governed by the temperature of the feed, its viscosity, and the interior diameter of the tube, or the speed of the pump, whichever was used.

Lactic acid feed of DP 2 (146.22 g) was fed to the column over a 2 hour period. The reboiler was held at a temperature of 222°-224° C. and a pressure of 94 torr. The top plate in the column was held at about 174°-178° C. the LD take-off point was at a temperature of about 167° C., the supply pot of feed was held at about 80°-90° C., and the teflon feedline was held at a temperature of 44° C. and the pressure controlled at 94 torr, throughout the column using manostats, manometers, cold traps, and vacuum pumps. After 2 hours, the pressure was lowered to 53 torr and an additional 51.82 g of feed material was fed to the column over a 95 minute time period. The products were collected from the two pressure conditions in separate fractions.

The first, higher-pressure fraction yielded 66.05 g of distillate, from which alkyl benzene solvent was decanted. The lower phase from the decantation procedure yielded a crude white crystalline LD product which was washed with low-boiling petroleum ether and vacuum dried to obtain 49.53 g of LD product. In a similar fashion, the second, lower-pressure cut yielded 62.45 g of distillate and 50.48 g of crude LD after washing with petroleum ether to remove the alkyl benzene solvent. The still-bottoms were cooled and alkyl benzene (AB) decanted to obtain 94.33 g of oligomeric lactic acids. The water condenser removed 4.8 ml of water. The material balance was calculated at 100.6%.

Crude lactide yield was based on conversion of $L_2A$ to LD at 88.9% of theoretical. On this basis, the overall yield of crude LD was 56.8%. GC assays of the two cuts were performed after treating an aliquot with diazomethane and comparing to standards. The GC analysis is set forth below.

TABLE 19

| | GC Assay (wt-%) | |
|---|---|---|
| Component | Cut 1 | Cut 2 |
| $L_1A$ | 36.3 | 19.0 |
| $L_2A$ | 8.0 | 4.6 |
| LD | 46.2 | 73.1 |
| $L_3A$ | 0 | 0 (<0.5) |
| AB | 3.4 | 1.2 |
| Total | 93.9 | 97.9 |

The overall yield of LD before purification was calculated at 34.6%. These results demonstrate that the crude LD product obtained from a DP 2 feedstock (as measured by titration) can be subjected to continuous codistillation with an appropriate solvent for collecting LD product.

EXAMPLE 36

The procedure of Example 35 was repeated, except that 116.87 g of DP 2.13 (by titration) feed was fed over 3.0 hours at a constant pressure of 53 torr. The crude LD collected after washing and drying weighed 73.43 g. After the addition was stopped, a second cut was taken since the distillation was continued for another 1.0 hr. The second cut provided 14.83 g of crude LD after washing and drying. The first cut, during the continuous addition, calculates as 70.7% of theory, neglecting impurities, and the second cut calculates as 14.3% of theory. A material balance of 103% was found for the LA and alkyl benzene (AB) materials. The two cuts were assayed by GC with the following results:

TABLE 20

| | GC Assay (wt-%) | |
|---|---|---|
| Component | Cut 1 | Cut 2 |
| $L_1A$ | 15.0 | 0 |
| $L_2A$ | 5.7 | 3.6 |
| LD | 63.5 | 78.7 |
| $L_3A$ | 0 | 0 |
| AB | 3.8 | 3.4 |
| $H_2O$ | 0.85 | 0.90 |
| Total | 88.85 | 86.6 |

The still bottom assay revealed the presence of 2.9% LD and 0% for $L_1A$, $L_2A$, and $L_3A$.

EXAMPLE 37

The LD from the first cut of Example 36 was recrystallized in dry methyl isobutyl ketone (MIBK), the LD separated by filtration, and the MIBK filtrate stripped on a rotary evaporator. The filtrate residue was combined with the still bottom from Example 36 by mixing and heating briefly at 120°-140° C. The DP of this mixture, by titration, was 2.37. The mixture was reconstituted to a DP of about 2.0-2.1 by mixing 2.96 ml of hot commercial 85% lactic acid. This reconstituted mixture assayed by GC to be 5.1% $L_1A$, 4.9% $L_2A$, and 35.4% LD. The balance of the material probably was higher $L_nA$ oligomers, (n greater than 3).

The reconstituted material was recycled in the procedure as set forth in Example 36. The feed weighed 94.19 g. The product recovered after the process was washed and dried to yield 44.34 g of a crude, white crystalline LD, which assayed at 65-71% LD. This experiment demonstrates the ability to recycle $L_nA$ containing still bottom to increase LD yield.

EXAMPLES 38-41

The still bottoms and purification rejects from Example 37 were reconstituted with additional commercial 85% $L_1A$ to a DP of 2.0-2.1 (measured by titration), and reused in a second recycle. In a similar manner, a third recycle was performed at the end of the second recycle using its still bottoms and purification rejects. The results recorded are set forth below.

TABLE 21

| Example | Recycle | Crude LD,(a) percent of theory | GC Assay, weight percent | LD Yield/Cycle,(b) percent of theory |
|---|---|---|---|---|
| 38 | 9 | 70.7 | 65.8 | 46.5 |
| 39 | 1 | 52.9 | 71.0 | 37.5 |
| 40 | 2 | 63.7 | 76.4 | 48.7 |
| 41 | 3 | 68.3 | 66.2 | 45.2 |
| Avg. | | 62.5 | 70.5 | 43.9 |

| | Component (wt-%) | | | | | |
|---|---|---|---|---|---|---|
| Example | $L_1A$ | $L_2A$ | LD | $L_3A$ | AB | GC Total |
| 38 | 15.0 | 5.7 | 65.8 | 0 | 3.8 | 89.6 |
| 39 | 13.0 | 5.5 | 71.0 | 0 | trace | 89.5 |
| 40 | 12.0 | 5.0 | 76.4 | 0 | 1.5 | 94.9 |
| 41 | 21.0 | 4.0 | 66.2 | trace | 2.1 | 93.3 |

(a) [Weight of crude distillate/weight of starting material × 0.889] × 100.
(b) Obtained by multiplying column 2 (crude LD) by column 3 (assay).

The above-tabulated results demonstrate that the liquid phase process of the invention can be conducted in a continuous recycle manner with substantially no drop in LD yield and no apparent loss of material. The process when run continuously should provide LD yields exceeding 90%.

EXAMPLE 42

The performance of feedstocks enriched in $L_1A$ to provide lactides by the vapor phase process was examined.

A feedstock enriched in $L_1A$ was prepared by diluting commercial 85% lactic acid (61% $L_1A$, 18% $L_2A$, 5% $L_3A$, 1% $L_4A$ and 15% water with water) at a ratio of 1:3, equilibrating the dilute solution to form $L_1A$ and distilling off water under reduced pressure/low temperature conditions. The diluted commercial lactic acid (750 g LA; 2438 g water) was refluxed for 8 hours and then distilled under vacuum to provide a $L_1A$ enriched lactic acid product containing 90.6% $L_1A$, 7.4% $L_2A$, 0.4% $L_3A$, 0% $L_4A$ and 1.6% water.

This $L_1A$ enriched product and other $L_1A$ enriched products obtained by a similar method were then diluted with various levels of water to provide the feedstocks set forth in Table 22.

TABLE 22

| | Feedstock Composition | | | | | |
|---|---|---|---|---|---|---|
| Feedstock Number | Component Percentages | | | | | Comments |
| | $L_1A$ | $L_2A$ | $L_3A$ | $L_4A$ | Water | |
| 1 | 65.3 | 5.3 | 0.3 | 0 | 29.1 | |
| 2 | 81.0 | 3.9 | 0 | 0 | 15.1 | |
| 3 | 61.3 | 18.1 | 4.9 | 1.0 | 14.7 | Commercial 85% lactic acid |
| 4 | 88.6 | 4.8 | 0.2 | 0 | 6.4 | |
| 5 | 90.6 | 7.4 | 0.4 | 0 | 1.6 | |

Each of the feedstocks set forth in Table 22 were processed by the vapor phase process of the invention, as described in Examples 8-19. The lactide products obtained from the various fractions were washed with cold water, filtered and the filtrates were extracted with methylene chloride to recover dissolved lactide. The lactide products obtained are described below in Tables 23-27.

TABLE 23

| Feedstock No. 1: 70.9% Aqueous Predominantly $L_1A$ | | | | | | | | |
|---|---|---|---|---|---|---|---|---|
| Cum. Time at Comp. (hr) | Catalyst Bed Temp (°C.) | Material Fed (g) | Total Material Collected (g) | Total Percent Recovery | Overall LD Composition | | Total LD % Yield | LD Yield/ CO Yield |
| | | | | | L-LD % | M-LD % | | |
| 1.25 | 197 to 218 to 200 | 56.2 | 35.32 | 62.8 | — | — | — | — |
| 3.00 | 205 | 78.9 | 66.61 | 84.4 | 95.65 | 4.35 | 18.9 | 48.3 |
| 5.50 | 204 | 113.7 | 98.36 | 86.5 | 97.25 | 2.75 | 18.3 | 38.1 |
| 7.77 | 205 | 102.1 | 93.57 | 91.6 | 97.41 | 2.59 | 14.6 | 35.0 |

TABLE 23-continued

Feedstock No. 1: 70.9% Aqueous Predominantly $L_1A$

| Cum. Time at Comp. (hr) | Catalyst Bed Temp (°C.) | Material Fed (g) | Total Material Collected (g) | Total Percent Recovery | Overall LD Composition L-LD % | M-LD % | Total LD % Yield | LD Yield/ CO Yield |
|---|---|---|---|---|---|---|---|---|
| 8.77 | 205 | — | 4.60 | — | — | — | — | — |
| | Sum | 350.9 | 298.46 | | | | | |

Total material percent recovery, including catalyst weight gain: 98.2 percent

TABLE 24

Feedstock No. 2: 84.9% Aqueous Predominantly $L_1A$

| Cum. Time at Comp. (hr) | Catalyst Bed Temp (°C.) | Material Fed (g) | Total Material Collected (g) | Total Percent Recovery | Overall LD Composition L-LD % | M-LD % | Total LD % Yield | LD Yield/ CO Yield |
|---|---|---|---|---|---|---|---|---|
| 1.5 | 182 to 221 to 207 | 61.88 | 38.88 | 62.8 | 90.89 | 9.11 | — | — |
| 3.5 | 204 | 80.92 | 70.76 | 87.4 | 94.09 | 5.91 | 31.8 | 61.2 |
| 5.5 | 204 | 79.73 | 70.82 | 88.8 | 94.07 | 5.93 | 29.6 | 56.7 |
| 6.5* | 203 | 38.68 | 36.05 | 93.2 | 92.71 | 7.29 | 30.5 | — |
| 9.0 | 204 | 91.18 | 85.37 | 87.0 | 94.89 | 5.10 | 25.5 | 46.8 |
| 10.0 | 203 | — | 5.13 | — | — | — | — | — |
| | Sum | 353.4 | 307.01 | | | | | |

Total material % recovery including catalyst weight gain: 100.0%
*GC analysis of entire cyclone collector contents without water washing

TABLE 25

Feedstock No. 3: 85% Aqueous Commercial Lactic Acid

| Cum. Time at Comp. (hr) | Catalyst Bed Temp (°C.) | Material Fed (g) | Total Material Collected (g) | Total Percent Recovery | Overall LD Composition L-LD % | M-LD % | Total LD % Yield | LD Yield/ CO Yield |
|---|---|---|---|---|---|---|---|---|
| 1.5 | 198 to 219 to 207 | 62.40 | 38.69 | 62.0 | — | — | — | — |
| 4.0 | 205 | 104.8 | 90.19 | 86.1 | 92.35 | 7.65 | 40.2 | 92.5 |
| 6.5 | 204 | 102.4 | 90.55 | 88.5 | 92.75 | 7.25 | 39.5 | 76.2 |
| 9.0 | 204 | 104.2 | 93.57 | 89.8 | 94.49 | 5.51 | 39.4 | 70.2 |
| 10.0 | 203 | — | 9.17 | — | — | — | — | — |
| | Sum | 373.8 | 322.17 | | | | | |

Total material % recovery, including catalyst weight gain: 98.2%

TABLE 26

Feedstock No. 4: 93.6% Aqueous Predominantly $L_1A$

| Cum. Time at Comp. (hr) | Catalyst Bed Temp (°C.) | Material Fed (g) | Total Material Collected (g) | Total Percent Recovery | Overall LD Composition L-LD % | M-LD % | Total LD % Yield | LD Yield/ CO Yield |
|---|---|---|---|---|---|---|---|---|
| 1.5 | 198 to 222 to 207 | 66.66 | 32.80 | 49.2 | — | — | — | — |
| 4.0 | 203 | 117.8 | 95.13 | 80.7 | 92.76 | 7.23 | 29.9 | 250 |
| 6.5 | 203 | 111.3 | 95.66 | 86.0 | 93.78 | 6.22 | 32.0 | 81.5 |
| 9.0 | 203 | 107.1 | 69.11* | 64.5 | 93.53 | 6.45 | 27.6 | ~91 |
| 10.0 | 202 | — | 13.77 | — | — | — | — | — |
| | Sum | 402.9 | 306.47 | | | | | |

Total material % recovery, including catalyst weight gain: 88.3%
*A plug developed in the collector which reduced gas flow and lactidde yield during the collection stage.

TABLE 27

Feedstock No. 5: 98.4% Aqueous Predominantly $L_1A$

| Cum. Time at Comp. (hr) | Catalyst Bed Temp (°C.) | Material Fed (g) | Total Material Collected (g) | Total Percent Recovery | Overall LD Composition L-LD % | M-LD % | Total LD % Yield | LD Yield/ CO Yield |
|---|---|---|---|---|---|---|---|---|
| 1.5 | 196 to 221 to 205 | 54.66 | 28.70 | 52.7 | 89.95 | 10.05 | — | — |

TABLE 27-continued

| Feedstock No. 5: 98.4% Aqueous Predominantly L₁A | | | | | | | | |
|---|---|---|---|---|---|---|---|---|
| Cum. Time at Comp. (hr) | Catalyst Bed Temp (°C.) | Material Fed (g) | Total Material Collected (g) | Total Percent Recovery | Overall LD Composition | | Total LD % Yield | LD Yield/ CO Yield |
| | | | | | L-LD % | M-LD % | | |
| 3.5 | 204 | 71.0 | 63.33 | 89.2 | 93.45 | 6.55 | 41.0 | 67.0 |
| 5.5 | 203 | 72.2 | 64.55 | 89.4 | 93.64 | 6.36 | 39.5 | 69.4 |
| 6.0* | 203 | 20.1 | 16.01 | 79.7 | 91.03 | 8.97 | 35.6 | — |
| 8.9 | 204 | 101.8 | 90.97 | 89.3 | 94.09 | 5.91 | 38.9 | 74.5 |
| 10.0 | 200 | — | 9.26 | — | — | — | — | — |
| | Sum | 319.6 | 277.82 | | | | | |

Total material recovery, including catalyst weight gain: 99.6%
*GC analysis of entire cyclone collector contents It can be seen that the $L_1A$ enhanced feedstocks produced higher levels of lactide as the water level is reduced. The high level of lactide produced by commercial 85% lactic acid (compared to Feedstock No. 2 containing 84.9% predominantly $L_1A$ feed) may be attributed to the higher percentages of $L_2A$, $L_3A$ and $L_4A$ contained therein (24.0%) which is produced during equilibration. These results suggest that a nearly anhydrous lactic acid feed containing a total quantity of $L_2A$, $L_3A$ and $L_4A$ of approximately 10% to 50% could be an ideal feed composition.

After correcting for lactide lost during the lactide washing/isolation procedures, the lactide yields obtained from Feedstocks No. 3 and No. 5 are estimated to be 45%.

EXAMPLE 43

The following Example Nos. 44 to 48 illustrate a liquid phase embodiment of the invention utilizing a packed bed distillation apparatus into which an LA feedstock was dropwise gravity fed via a dropping funnel. The apparatus included an uppermost straight distilling head, an intermediate packed bed section and a lowermost round bottom flask receiver.

The packed bed section was made up of two 20-cm long, 2.0 cm diameter, units connected end to end. Each unit was filled with approximately 48 grams of 6 mm glass beads. The glass beads in the upper unit were lightly treated with tetraisopropyl titanate, while the beads in the lower unit were untreated.

The distilling head was provided with an upper sidearm takeoff attached to a water cooled condenser for collecting water vapor and unreacted vaporized LA. The column was also provided with a lower side arm takeoff beneath the packed bed section and a carrier gas entry port between the lower side takeoff and the bottom receiver.

The distillation column was wrapped with appropriate heating tapes and insulation, and provided with temperature monitors, to establish a temperature of 90° C. in the distillation head, 200°–210° C. in the upper packed bed and 200° C. in the lower packed bed. The pressure in the column was maintained at 50 torr via a vacuum pump and manistat connected to the sidearm takeoff collection vessels.

EXAMPLE 44

40 grams of commercial 85% liquid LA were added to the column described in Example 43 at a slow dropwise (3 to 6 seconds/drop) rate over a period of about 3 hours. The liquid LA contacted the surface of the glass beads forming a liquid fluid reaction mass that slowly percolated down the column. Throughout the reaction, a purge stream of argon gas was introduced to the column via the carrier gas port adjacent the bottom of the column. The argon purge gas flowed up the column exiting via the two sidearm takeoffs, but principally through the lower takeoff.

As the LA reaction mass became increasingly heated as it traversed down the column, the lactic acid began to oligomerize in accordance with the equations set forth herein forming $L_2A$, $L_3A$, LD, etc. The oligomer containing reaction mass was intimately contacted by the argon gas which acted to sweep the vaporizing LD from the reaction mass. 9.8 grams of slightly off-white, rapidly crystallizing liquid was obtained in the collector attached to the lower sidearm takeoff. 0.8 grams of pure white crystals were collected from the water-cooled condenser connected to the upper sidearm takeoff. A total of 10.6 grams out of a theoretical 27.9 grams (38%) of crude LD were obtained. The product from the purified crystals from the lower sidearm collector was rinsed with ice cold isopropyl alcohol and vacuum dried to white crystals. IR analysis of samples of the crystals from the upper sidearm condenser and the lower sidearm collector gave an IR spectrum identical with that of L-lactide.

While the actual argon flow rate was not measured in this experiment, it was determined that the argon flow rate was sufficient to intimately contact the liquid reaction mass flowing downwardly over the surface of the glass beads and sweep the lactide vaporizing therefrom forming a gaseous product stream of argon and lactide which is removed from the column via the lower sidearm takeoff. The argon likewise swept the water vapor and vaporized lactic acid out of the column via the upper sidearm takeoff.

EXAMPLE 45

This example was repeated in a slightly modified form of the apparatus described in connection with Example 44. The straight distillation head was replaced with a Claisen distilling head with the dropping funnel mounted on top. The bottom sidearm takeoff was slightly inclined upwardly to prevent liquid oligomer from flowing into the LD collector. Finally, the carrier gas inlet port was moved to the round bottom receiver connected to the bottom of the column so that the argon purge gas could be swept across any liquid oligomer collected therein and then flow up the column.

Three runs were made at 60 torr. In the first run, 37.5 grams of 85% commercial LA was added over 190 minutes (0.2 gm/min). The temperature of the distillation head, top of the packed column and bottom of the packed column were 85°/160°/200° C., respectfully. A total of 32.4 grams of material was recovered (85.5% yield); 6.4 gm of water/LA at the upper sidearm, 25.1 gm crude LD/LA at the lower sidearm and 0.9 oligomers in the bottom receiver.

The crude LD/LA was vigorously shaken with ice water in which the LA dissolved and LD remained as a precipitate which was separated by filtration. 1.2 gm LD were obtained showing a yield of 4% based on a theoretical yield of 26.6 gm. Since the ice water separation technique is only able to recover 88% of the lactide present, a corrected yield of 5.1% was obtained.

In a second run, without cleaning the apparatus, 30.1 gm of 85% LA were fed over 105 minutes (0.29 gm/min). The temperature at the three column positions were maintained at 110°/170°/215° C., respectively. A total of 29.5 gm (98.3% yield) was collected; 8.4 gm water/LA, 14.0 gm crude LD/LA and 5.8 gm oligomers.

LD was separated by ice water washing and 3.0 gm were collected, giving a yield of 14.1%, based upon a theoretical yield of 21.3 gm and a corrected yield of 16%. A third run was made without cleaning or altering the apparatus. 36.9 gm of commercial 85% LA was fed over 180 minutes (0.2 gm/min) and the temperature was maintained at 105°/190°/240° C. 36.8 gm total product was recovered; 9.7 gm water/LA, 24.3 gm crude LD/LA and 2.8 gm oligomers. Recovery of lactide by ice water washing yielded 4.4 gm, a 16.9% yield based upon a theoretical yield of 26 gm and a corrected yield of 19.2%.

EXAMPLE 46

A run similar to Example 45 was made with the column packed with untreated 3 mm glass beads, 116.2 gm total. The column was maintained at 60 torr with a continuous argon purge. 45.6 gm commercial 85% LA were added over 7.5 hours (0.1 gm/min) and the temperature was maintained at 57°/175°/220° C. 43 gm total product was recovered; 11.2 gm water/LA, 17.8 gm crude LD/LA and 14.0 gm oligomers.

Separation of lactide by ice water washing yielded 4.2 gm LD, a 13% yield based upon a theoretical yield of 32.2 gm and a corrected yield of 14.8%.

EXAMPLE 47

The apparatus of Example 34 was modified by including an upper argon gas inlet in addition to that in the bottom receiver. Flow meters were also installed in both argon lines.

In a first run, the second argon inlet was between the two sections comprising the packed bed, i.e., midway of the distillation column. 54.5 gm of 85% LA was fed over 4 hours (0.23 gm/min). The column was maintained at 60 torr and an argon flow rate of 21.4 cc/min was maintained at both inlets (total argon:LA feed mole ratio of about 0.32:1). The temperature was maintained at 135°/170°/195° C. and 44.7 gm (82%) of total products were recovered; 16.1 gm water/LA, 6.0 gm crude LD/LA and 22.6 gm oligomers.

Lactide was recovered from the crude LD/LA product collected in the lower sidearm receiver by dissolving the crude sample of LD in cold ($\approx$ 10 C) methylene chloride, which was extracted with 5% aqueous sodium bicarbonate (NaHCO$_3$) until the evolution of CO$_2$ ceases and the pH of the aqueous phase remains greater than about 8.0. The methylene chloride solution of purified LD was then dried over powdered sodium sulfate (Na$_2$SO$_4$), filtered, and the CH$_2$Cl$_2$ stripped on a rotary evaporator. This provides an essentially 100% recovery of LD.

2.4 gm (6% yield) LD was recovered by this procedure.

In an attempt to improve lactide yield, the second argon inlet was moved to between the packed bed and the Claisen distillation head, and a second run was made. 25.3 gm commercial, 85% lactic acid was fed over 80 minutes (0.316 gm/min). The column was maintained at 60 torr and the argon flow rate at each inlet was maintained at 21.4 cc/min (total argon:LA feed mole ratio of 0.62:1). The temperature in the column was maintained at 80°/185°/205° C. and 28.02 gm (111% yield) of total product was recovered; 6.4 gm water/LA; 20.4 gm crude LD/LA and 1.2 gm oligomers. The excess yield resulted from material retained in the column during the first run.

LD was recovered from the crude LD/LA in the manner described in connection with the first run and 3.9 gm LD was recovered which amounted to a 21.8% yield based upon a theoretical yield of 17.9 gm.

In a third run, similar to the second run, 32.9 gm of commercial 85% LA was fed over 150 minutes (0.219 gm/min). The column pressure and argon flow rates were the same as the second run (argon:LA feed mole ration 0.89:1) and the temperature was 90°/195°/205° C. 36.7 gm (112% yield) of total product were obtained; 5.7 gm water/LA, 27.6 gm crude LD/LA and 3.4 gm oligomers. The excess yield in this run also resulted from material retained in the column during the first run.

4.93 gm LD was recovered from the crude LD/LA by the method described in connection with the first run. This represents a LD yield of 21.2% based upon a theoretical yield of 23.2 gm LD.

EXAMPLE 48

This example illustrates the use of pure L$_2$A as the feed material.

A distillation column similar to that used in Examples 46 and 47 was set up. A smaller packed bed (67.5 cc) of clean 3 mm glass beads (94.4 gm) was used and the remainder of the apparatus was as described except that the argon was preheated to 200° C. prior to injection into the column.

19.7 gm of 99% L$_2$A (0.122 mole) was fed to the column over 155 minutes (0.127 gm/min). The column was maintained at 65 torr with an argon flow rate into the bottom receiver only of 21.4 cc/min (argon:L$_2$A feed mole ratio of 1.22:1). The temperature was maintained at 140°/190 /215° C.

A crude crystallized LD product was collected at both the upper and lower sidearm takeoffs. LD was separated from both products by the described methylene chloride/sodium bicarbonate method. 10 gm (57% yield) of pure white crystalline LD (m.P. 94°-5° C.) were obtained.

EXAMPLE 49

This example illustrates the high temperature catalytic conversion of methyl lactoyllactate (MeLLA) to lactide.

The apparatus used included a pressure equalizing dropping funnel positioned at the top of a heated 18-inch long, 0.9-inch diameter glass tube which contained a catalyst or glass beads. A round-bottom flask receiver cooled in dry ice was positioned at the bottom of the glass tube. Heated nitrogen was passed downwardly of the column. The nitrogen flow rate was monitored as it exited the apparatus with a bubble flow meter. MeLLA was fed dropwise into the top of the tube, and the material obtained in the cooled collector was examined by proton nuclear magnetic resonance (NMR) spectroscopy.

In one experiment, the column was filled to a height of approximately 1 foot with glass beads coated with titanium tetra(isopropoxide) which had a void volume of approximately 55 ml. The column external temperature ranged from about 340° to about 480° C., and the nitrogen flow rate (unheated) was approximately 44 ml/minute. The collected material was examined by NMR spectroscopy and found to be mainly MeLLA. NMR analysis of this product indicated that lactide was present in a quantity which corresponds to approximately 20% yield from MeLLA.

In another similar run, using heated nitrogen and no catalyst, little or no lactide was produced. These comparative results indicate that titanium tetra(isopropoxide) served to catalyze the conversion of MeLLA to lactide.

EXAMPLE 50

In this example the effect of the template catalyst di-n-butyltin oxide on lactide production was tested. The postulated "template" mechanism involves tying together the two ends of a hydroxyalkanecarboxylic acid by temporary binding to tin, thereby facilitating cycle ester formation. Two experiments (labelled A and B) were performed to test the template catalyst di-n-butyltin oxide. In both experiments, water was removed from the reaction as an azeotrope with mesitylene (1, 3, 5-trimethylbenzene).

In each experiment, 50.0 g of 85% L-lactic acid was added dropwise to refluxing mesitylene (400 ml) in flasks equipped with Barrett tubes to separate and collect the distilled water. In experiment A, the lactic acid solution was added over a period of 1.5 hours whereas in experiment B, the lactic acid solution was added over 50 minutes. In Experiment B, 24.97 g di-n-butyltin oxide was added before reflux was initiated.

Experiment A was stopped after approximately 5 hours after 29 ml water plus lactic acid had distilled. The upper phase of the solution was decanted from a lower phase (approximately 12 g) and 450 ml pentane was added to precipitate lactide from the upper phase. After cooling, this mixture was filtered to obtain a semi-solid containing white crystalline material (4.92 g after drying under vacuum). This material was dissolved in methylene chloride and extracted with 5% sodium bicarbonate (a procedure shown to give 100% recovery of lactide from lactide/lactic acid mixtures) to give 1.9 g of a material assumed to be rich in lactide.

Experiment B was stopped after approximately three hours reflux after approximately 10.5 ml water plus lactic acid had distilled. In this case, a second phase was not noted upon cooling. The catalyst was filtered and 450 ml pentane was added to the filtrate. A brown, amorphous material was obtained by filtration (20.9 g after drying). Methylene chloride/aqueous sodium bicarbonate partitioning gave 4.1 g of a material potentially rich in lactide. The mesitylene/pentane filtrate produce another brownish layer which had significant white crystalline material (21 g). This material was partitioned with methylene chloride/aqueous sodium bicarbonate to produce 17.3 g of a clear, viscous material which may also have contained significant lactide.

The significantly increased quantities of products obtained from methylene chloride/aqueous sodium bicarbonate partitioning in Experiment B and the absence of a lower layer in Experiment B (presumably relatively anhydrous lactic acids in Experiment A) suggests that lactic acid condensation as well as lactide formation was enhanced in Experiment B. These results suggest that di-n-butyltin oxide exerted a catalytic effect in lactic acid condensation was well as lactide formation.

EXAMPLE 51

This run was conducted in order to determine the product distribution obtained when vaporized L-methyl lactate was passed through a bed of 10–20 mesh silica gel/alumina catalyst (Akzo LA-30-5P catalyst, 87% silica/13 percent alumina, Akzo Chemicals B.V.).

The same reactor described in Examples 8–19 was used for this experiment. The nitrogen flow was 1580 ml/min. The vaporized methyl lactate and nitrogen were passed through the reactor at a superficial velocity of approximately 0.10 ft/sec with a residence time of 3.2 seconds within the catalyst bed. The wt % organic in feed was 27.3%. Carbon monoxide concentrations were measured after separation of condensable LD/LA in a dry ice cooled cyclone collector. The entire condensed product was analyzed by gas chromatography. The obtained results are recorded below:

TABLE 28

| Cum. Time at Completion (hr) | Cat. Bed Temp. (°C.) | L-Methyl Lactate Fed (g) | All Products (g) | Total % Recovery | Overall LD Composition | | Total LD (mole %) | LD Yield/ CO Yield |
|---|---|---|---|---|---|---|---|---|
| | | | | | % L-LD | % M-LD | | |
| 1.5 | 203 | 58.9 | 58.9 | 100 | — | — | — | — |
| 4.5 | 204 | 127.5 | 115.5 | 90.6 | 86.2 | 13.8 | 7.5 | 1.1 |
| 7.3 | 204 | 118.8 | 106.8 | 89.9 | 86.1 | 13.9 | 7.1 | 1.6 |

The overall mass recovery was 95%. The LD/CO ratios indicate that from 38% to 48% of the methyl lactate which underwent reaction was converted to carbon monoxide rather than forming LD.

EXAMPLE 52

This run was performed by passing vaporized L-methyl lactoyllactate (MeLLA) through a bed of 10 to 20 mesh silica/alumina catalyst (Akzo LA-30-5P catalyst, 87% silica/13% alumina, Akzo Chemicals B.V.). A tubular reactor constructed from 0.5 inch diameter stainless steel tubing was used for this run. This reactor was suspended in a heated sand bath so that the nitrogen stream (500 ml/min) first passed through approximately 50 inches of heated stainless steel tubing before contacting the catalyst bed in an upward direction. The MeLLA was introduced into the downward flowing heated nitrogen stream immediately above a bed of glass beads to aid MeLLA vaporization. The vaporized MeLLA/nitrogen stream was then directed in an upward fashion to the catalyst bed to guarantee complete MeLLA vaporization before contacting the catalyst bed. For the two experiments described below, the wt % of organic in the feed was 16.8%; and the residence time within the catalyst bed was 1.0 seconds. Product was collected by cooling in dry ice cooled flasks. The entire condensed product was analyzed by gas chromatography. The following definitions explain the results recorded below:

$$\text{Percent Conversion} = \frac{\text{Moles MeLLA Reacted}}{\text{Moles MeLLA Fed}} \times 100 =$$

$$\frac{\text{Moles MeLLA Fed} - \text{Moles MeLLA Recovered}}{\text{Moles MeLLA Fed}} \times 100$$

$$\text{Lactide Selectivity} = \frac{\text{Moles LD Formed}}{\text{Moles MeLLA Reacted}} =$$

$$\frac{\text{Moles LD Formed}}{\text{Moles MeLLA Fed} - \text{Moles MeLLA Recovered}}$$

$$\text{Combined Lactide Percent Yield} = \frac{\text{Moles LD Collected}}{\text{Moles MeLLA Fed}}$$

TABLE 29

| Run (44409-) | Cat. Bed Temp. (°C.) | Conversion (%) | Mass Recovery (%) | Selectivity (%) L-LD | Selectivity (%) M-LD | Combined LD Yield (%) |
|---|---|---|---|---|---|---|
| 12 | 205 | 76 | 97 | 34.8 | 1.8 | 28 |
| 16 | 195 | 54 | 85 | 41.4 | 1.9 | 24 |

The results indicate that MeLLA conversion increased as the catalyst bed temperature increased. The total LD selectivity was found to be greater at the lower catalyst bed temperature. The fact that the total LD selectivities ranged from 36.8% to 43.3% indicates that a major quantity of the MeLLA which had reacted had formed products other than lactide. Carbon monoxide levels were not measured in the reactor product stream, but it is probable that a significant quantity of MeLLA was converted to carbon monoxide and acetaldehyde. It can also be seen that the lactide yields obtained in the silica/alumina (87:13) catalyzed thermolysis of MeLLA is similar to the lactide yield obtained in the titanium tetra(isopropoxide) catalyzed thermolysis of MeLLA as described in Example 49.

EXAMPLE 53

One concept for the synthesis of LD is to make LD the most volatile component in the reaction mixture in order to readily separate it from reagents or side products. Lactate esters of n-octadecanol were prepared to participate in the following equilibrium:

$2CH_3CH(OH)CO_2C_{18}H_{37} \neq$

Octadecyl Lactate

$CH_3CH(OH)CO_2CH(CH_3)CO_2C_{18}H_{37} + C_{18}H_{37}OH$

Octadecyl Lactoyllactate

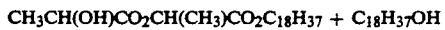

$CH_3CH(OH)CO_2CH(CH_3)CO_2C_{18}H_{37} \neq$

Lactide (LD) + $C_{18}H_{37}OH$

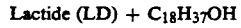

In these equilibria, LD (boiling point of 240° C. at 200 torr) has the lowest boiling point compared to n-octadecanol (boiling point of 300° C. at 200 torr), octadecyl lactate (boiling point of 365° C. at 200 torr) and octadecyl lactoyllactate (bpt. >365 C/200 torr). Distillation of LD was expected to shift these equilibria towards LD and leave octadecanol in the distillation flask.

Octadecyl lactate (OdLA) was prepared in nearly quantitative yield by heating equilmolar quantities of LA and n-octadecanol, and using a Barrett tube to remove the water formed. Octadecyl lactoyllactate (OdLLA) was prepared by reacting LD and n-octadecanol in benzene in the presence of sulfuric acid. OdLLA can also be prepared by transesterification of MeLLA with n-octadecanol.

Before performing experiments directed towards the synthesis of LD, catalyst evaluation experiments were performed with Thermal Gravimetric Analysis (TGA) by mixing OdLA with a 2% catalyst loading to determine their efficiencies in promoting weight loss (presumed to be mainly LD). The following weight losses were observed after 45 minutes at 200° C. using the following catalyst: zinc oxide (33%), titanium tetra(isopropoxide) (25%), stannous octoate (24%), zinc lactate (23%), and p-toluenesulfonic acid (19%).

A first experiment was performed which used 1.50 g OdLA and 0.027 g stannous octoate in a small stirred sublimation apparatus. This mixture was initially heated at approximately 148° C. and 1-3 torr pressure, a temperature and pressure which is slightly above the boiling point of LD and 30°-40° C. below the boiling points of OdLA and octadecanol. An initial sample of 0.64 g was collected over a 2.5 hour period which contained approximately 20 molar % LD and approximately 40 molar % of OdLA and n-octadecanol (by NMR spectroscopy).

In a second experiment, LD was also prepared from 34.7 g OdLA in the presence of 6.94 g zinc oxide (20%) by distillation from a 100 ml flask (heated in an oil bath) equipped with a distillation column which was externally heated in a gradient fashion. The system pressure was adjusted to approximately 1 torr and the oil bath temperature was raised to 200°-215° C. The external temperature of the distillation column ranged from approximately 130°-150° C. at the bottom of the column to approximately 45°-150° C. at the top of the column during distillation. Two fractions were collected during the distillation. Fractions in this and subsequent distillations discussed below were analyzed using gas chromatography (GC) and peak areas were ratioed to provide component percentages.

The first fraction had a nearly constant boiling point (approximately 160° C. at 1.1 torr) which was above that of LD. The weight of this first fraction was 17% of the starting OdLA weight. According to GC analysis, the fraction consisted of approximately 25% L-LD, 18% n-octadecanol and 57% of a compound with a molecular weight of about 102 daltons, as measured by gas chromatography/ mass spectroscopy. The yield of this LD in this experiment was about 20%. The observed constant boiling point suggests that LD and n-octadecanol formed a maximum boiling azeotrope.

The weight of the second fraction collected was 44% of the starting weight. The second fraction consisted mainly of the 102-dalton component and n-octadecanol. The low molecular weight product may be a degradation product of LD or OdLA.

In a third experiment, LD was prepared from 40.3 g OdLLA in the presence of 4.03 g zinc oxide (10%) by a distillation approach similar to that described for OdLA. This distillation was performed with a system pressure of approximately 2 torr and an oil bath temperature of about 180°–190° C. External temperatures of the distillation column ranged from 150°–230° C. at the bottom of the column to 91°–140° C. at the top of the column during distillation. No attempt was made to fractionate products and a single fraction was collected which had a weight corresponding to about 91% of the starting OdLLA weight. GC analysis indicated that the fraction was composed of approximately 19% LD, 56% n-octadecanol and 25% OdLA. The L-LD:meso-LD ratio was approximately 3:1. The LD yield was approximately 50%.

A fourth distillation experiment was performed with 31.6 g OdLLA in the presence of 3.16 g zinc oxide (10%). The external temperatures of the distillation column ranged from 106°–155° C. at the bottom of the column to 90°–104° C. at the top of the column. Distillation was performed with a system pressure of approximately 1.5 torr and an oil bath temperature of about 190°–210° C. One fraction was collected close to the boiling point of LD which had a weight corresponding to about 13% of the starting OdLLA weight. This fraction contained approximately 48% LD, 43% 1-octadecanol and 12% OdLA, based on GC analysis. The L-LD:meso-LD ratio was approximately 15:1. The LD yield was approximately 18%. GC analysis of the pot residue showed that it contained approximately 2% LD, 17% n-octadecanol, 80% OdLA and 1% OdLLA. These results indicate that LD may be prepared from OdLLA and that n-octadecanol and LD tend to co-distill with each other. These results also indicate that OdLLA is cleaved at the internal ester site by n-octadecanol to form OdLA under the reaction conditions.

EXAMPLE 54

This Example compares the efficiency and improved yield obtained when starting at a DP of DP 2.02 (as measured by titration). The procedure of Example 35, which was carried out at DP 2.02, was essentially repeated except that the DP of the starting material of this experiment was about DP 2.9. The alkyl benzene (AB) was brought to 228° to 232° C. at a pressure of 54 torr. AB was distilled slowly up through the column, the top of which was fed with an LA feedstock of DP=2.95 (average of 2.98 and 2.91 from duplicate titrations.) The feedstock was added dropwise at a rate of approximately 1 drop per second. The temperature of the top plate was 168° C. The feed line temperature was 74° C. to 84° C., and the supply pot temperature was 195° C. to 207° C. After 20 minutes, AB and crude LD began to distill slowly. A 61.3 g quantity of an LA-containing feedstock of DP=2.95 was fed over an hour time period, resulting in 9.6 g of distillate. After decanting the AB, washing the crude LD with low boiling petroleum ether, and vacuum drying, a 6.85 g yield of crude LD was obtained, which assayed as 64.3 weight % LD by GC analysis. The yield of LD in this experiment was 12.1%. LA in the still bottom, which was obtained by decanting off the AB, weight 55.2 g. Material balance for the reaction was 101%.

The procedure shows that at higher DP's, the yields and rates of LD production are lower than at DP=2.02.

EXAMPLE 55

The procedure of Example 35 was repeated except that the LA-containing feedstock had a DP of about DP 1.5. A rapid distillation was obtained. 47.39 g of the feedstock was added over a 1.0 hour period to obtain 21.28 g of washed, dry, crude LD (56% of theoretical yield). However, the distillate as assayed by GC contained only 20.1% LD.

The procedure demonstrates that at DP's lower than 2, a rapid distillation of crude LD can be generated, but the LD is of much lower purity than that generated at DP=2.02.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A process for producing a cyclic ester which comprises:
    (a) providing a feedstream comprising XA, wherein XA is a solution comprising compounds selected from the group consisting of a single hydroxy carboxylic acid or its ester, salt or amide ($X_1A$); a straight chain two member molecule of $X_1A$ ($X_2A$); a straight chain three member molecule of $X_1A$ ($X_3A$); a straight chain four member molecule of $X_1A$ ($X_4A$); and mixtures thereof and wherein said XA comprises $X_2A$ and is diluted in an organic solvent; and
    (b) removing water from said feedstream to directly form said cyclic ester from $X_2A$.

2. A process, as claimed in claim 1, wherein said cyclic ester is XD.

3. A process, as claimed in claim 1, wherein said solvent forms an azeotrope with water in said feedstream.

4. A process, as claimed in claim 3, wherein said step of removing water comprises heating said feedstream to a temperature effective to remove said azeotrope.

5. A process, as claimed in claim 1, wherein said solvent is selected from the group consisting of benzene, toluene, ethyl benzene, xylenes, cumene, trimethyl benzenes, acetonitrile, halogenated aromatic solvents, hydrocarbons, and mixtures thereof.

6. A process, as claimed in claim 1, wherein said solvent comprises toluene.

7. A process, as claimed in claim 1, wherein said solvent comprises acetonitrile.

8. A process, as claimed in claim 1, wherein said step of providing comprises:
    (a) providing an aqueous solution comprising XA;
    (b) removing substantially all free water from said aqueous solution to form a dehydrated feedstream; and
    (c) adding organic solvent selected from the group consisting of benzene, toluene, ethyl benzene, xylenes, cumene, trimethyl benzenes, acetonitrile and mixtures thereof to said dehydrated feedstream.

9. A process, as claimed in claim 1, wherein at least about 5% of said XA is converted to said cyclic ester.

10. A process, as claimed in claim 1, wherein XA comprises $X_1A$, and wherein $X_1A$ is an α-hydroxy carboxylic acid, or an ester, salt, or amide thereof.

11. A process as claimed in claim 1, wherein XA comprises $X_1A$, and wherein $X_1A$ is selected from the acids, ester, salts, or amides of the group consisting of lactic acid, glycolic acid, tartaric acid, mandelic acid, benzylic acid, 1-hydroxy 1-cyclohexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methylbutanoic acid, 2-hydroxybutanoic acid, 2-hydroxypentanoic acid and mixtures thereof.

12. A process, as claimed in claim 1, wherein XA comprises $X_1A$, and wherein $X_1A$ is selected from the group consisting of lactic acid, glycolic acid, tartaric acid, a lactate salt, a glycolate salt, a tartrate salt, and mixtures thereof.

13. A process, as claimed in claim 1, wherein XA comprises $X_1A$, and wherein $X_1A$ is lactic acid or a lactate salt.

14. A process, as claimed in claim 1, wherein XA comprises $X_1A$, and wherein $X_1A$ is ammonium lactate.

15. A process, as claimed in claim 1, wherein said feedstream comprises at least about 0.5 wt/vol % LA.

16. A process, as claimed in claim 1, wherein said feedstream initially comprises less than about 50 wt/vol % water.

17. A process, as claimed in claim 1, wherein said feedstream comprises heat stable LA, or esters, salts, or amides thereof.

18. A process, as claimed in claim 1, wherein said feedstream comprises fermentation broth containing LA, esters, salts, or amides thereof.

19. A process, as claimed in claim 1, wherein the concentration of XA is less than about 25 wt/vol %.

20. A process, as claimed in claim 1, wherein said step of removing water is conducted until a water concentration in said feedstream of less than about 2 wt % is achieved.

21. A process, as claimed in claim 1, wherein said process is continuous.

22. A process, as claimed in claim 21, wherein water-containing components of said feedstream are initially dehydrated and wherein said process further comprises continuously adding dehydrated additional feedstream to said feedstream and continuously removing said cyclic ester from said dehydrated feedstream.

23. A process, as claimed in claim 1, wherein the boiling point of said organic solvent is between about 55° C. and about 250° C. at 1 atm.

24. A process, as claimed in claim 1, wherein said feedstream further comprises an esterification catalyst.

25. A process, as claimed in claim 24, wherein said catalyst is selected from the group consisting of ion exchange resins, zeolites, soluble acids, alumina-based catalysts, metal catalysts, enzymes, template catalysts, silica-based catalysts, micellar catalysts, and mixtures thereof.

26. A process, as claimed in claim 1, wherein said feedstream further comprises a blocking agent.

27. A process, as claimed in claim 26, wherein said blocking agent is selected from the group consisting of anhydrides, ketones and aldehydes.

28. A process, as claimed in claim 1, further comprising recovering said cyclic ester to form a cyclic ester-containing fraction and a cyclic ester-depleted fraction.

29. A process, as claimed in claim 28, wherein said step of recovering is selected from the group consisting of crystallization, solvent extraction, washing with solvent, chromatography, membrane partitioning, distillation, and sublimation.

30. A process, as claimed in claim 28, wherein said step of recovering comprises crystallization.

31. A process, as claimed in claim 30, wherein said cyclic ester is crystallized directly from the feedstream from which water has been removed.

32. A process, as claimed in claim 30, wherein said step of recovering further comprises concentrating said cyclic ester prior to crystallization.

33. A process, as claimed in claim 30, wherein the continuous phase of said feedstream is toluene.

34. A process, as claimed in claim 33, wherein said continuous phase is removed and said cyclic ester is dissolved in a second continuous phase prior to crystallization.

35. A process, as claimed in claim 30, further comprising drying said crystallized cyclic ester.

36. A process, as claimed in claim 28, wherein said step of recovering comprises solvent extraction.

37. A process, as claimed in claim 36, wherein said step of recovering comprises extracting said cyclic ester into an extraction solvent, wherein said cyclic ester is more soluble in said extraction solvent than in the continuous phase of said feedstream.

38. A process, as claimed in claim 36, wherein said step of recovering comprises adding a solution to said feedstream from which water has been removed which when mixed with the continuous phase of said feedstream reduces the solubility of said cyclic ester in said mixture.

39. A process, as claimed in claim 38, wherein said solution comprises an alkane solvent.

40. A process, as claimed in claim 36, wherein said step of recovering comprises adding a solvent to said feedstream from which water has been removed, wherein XA comprises $X_1A$, and wherein unreacted components and oligomers of $X_1A$ in said feedstream are more soluble in said solvent than in the continuous phases of said treated feedstream.

41. A process, as claimed in claim 40, wherein said solvent is an aqueous solvent.

42. A process, as claimed in claim 41, wherein said solvent is an aqueous solvent containing a base.

43. A process, as claimed in claim 28, wherein said cyclic ester-depleted fraction is recycled to said feedstream.

44. A process, as claimed in claim 43, wherein oligomers in said cyclic ester-depleted fraction are hydrolyzed prior to recycling.

45. A process, as claimed in claim 43, wherein said components are converted directly into said cyclic ester.

46. A process for producing XD, which comprises:
  (a) providing an azeotropic solution comprising XA, wherein the concentration of said XA is less than about 25 wt/vol % and wherein the organic solvent component of said azeotrope is selected from the group consisting of benzene, toluene and xylenes;
  (b) removing the azeotrope from said azeotropic solution to form said XD; and
  (c) recovering said cyclic ester by crystallization.

47. A process, as claimed in claim 46, wherein said XD is LD and said XA is LA.

48. A process for producing a cyclic ester derived from $X_1A$, which comprises:

(a) vaporizing a portion of a feedstream comprising XA; and
(b) reacting said vaporized portion of said feedstream in a reaction zone maintained at pressure and temperature conditions sufficient to maintain said vaporized portion in a vaporized state and to form said cyclic ester.

49. A process, as claimed in claim 48, wherein at least about 5% of said XA is converted to said cyclic ester.

50. A process, as claimed in claim 48, wherein said cyclic ester is formed directly from $X_2A$.

51. A process, as claimed in claim 48, wherein said cyclic ester is XD.

52. A process, as claimed in claim 48, wherein $X_1A$ is an α-hydroxy carboxylic acid, or an ester, salt, or amide thereof.

53. A process, as claimed in claim 48, wherein said $X_1A$ is selected from the acids, esters, salts and amides of the group consisting of lactic acid, glycolic acid, mandelic acid, benzylic acid, 1-hydroxy 1-cyclohexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methylbutanoic acid, 2-hydroxybutanoic acid, 2-hydroxypentanoic acid, and mixtures thereof.

54. A process, as claimed in claim 48, wherein $X_1A$ is selected from the group consisting of lactic acid, glycolic acid, a lactate salt, a glycolate salt, and mixtures thereof.

55. A process, as claimed in claim 48, wherein $X_1A$ is lactic acid or a lactate salt.

56. A process, as claimed in claim 48, wherein $X_1A$ is ammonium lactate.

57. A process, as claimed in claim 48, wherein said feedstream comprises between about 50 weight % and about 100 weight % LA.

58. A process, as claimed in claim 48, wherein said vaporized portion of said feedstream comprises between about 10 wt % and about 50 wt % organic material.

59. A process, as claimed in claim 48, wherein said feedstream comprises heat stable lactic acid, or esters, salts, or amides thereof.

60. A process, as claimed in claim 48, wherein said feedstream comprises at least about 90 wt/vol % $X_1A$.

61. A process, as claimed in claim 48, wherein the feedstream has a DP of less than or equal to about 4.

62. A process, as claimed in claim 48, wherein the temperature of said reaction zone is between about 150° C. to about 250° C. and the pressure of said reaction zone is between about 10 torr and about 900 torr.

63. A process, as claimed in claim 48, wherein said portion of said feedstream is vaporized prior to entry into said reaction zone.

64. A process, as claimed in claim 48, wherein said process is continuous.

65. A process, as claimed in claim 48, wherein the average residence time of the feedstream in the reaction zone is between about 0.5 seconds and about 12 seconds.

66. A process, as claimed in claim 48, further comprising passing a nonreactive carrier gas through said reaction zone.

67. A process, as claimed in claim 66, wherein said carrier gas is nitrogen.

68. A process, as claimed in claim 48, wherein said reaction zone contains an esterification catalyst.

69. A process, as claimed in claim 68, wherein said catalyst is selected from the group consisting of alumina, silica, beryllium oxide, yttrium oxide, zirconium oxide, mixed metal oxides and mixtures thereof.

70. A process, as claimed in claim 68, wherein said catalyst is an alumina-based catalyst.

71. A process, as claimed in claim 48, further comprising recovering said cyclic ester from said reaction zone.

72. A process, as claimed in claim 71, wherein said step of recovering comprises condensing said reacted feedstream to below a temperature at which said reacted feedstream is in vapor phase.

73. A process, as claimed in claim 72, further comprising separating said cyclic ester from said condensed reacted feedstream.

74. A process, as claimed in claim 73, wherein the cyclic ester-depleted fraction is recycled to said feedstream.

75. A process, as claimed in claim 74, wherein oligomers in said cyclic ester-depleted fraction are hydrolyzed prior to recycling.

76. A process, as claimed in claim 73, wherein the cyclic ester is dried.

77. A process, as claimed in claim 76, wherein said cyclic ester is further purified by recrystallization from a composition comprising components selected from the group consisting of methyl isobutyl ketone, ethyl acetate, butyl acetate and mixtures thereof.

78. A process, as claimed in claim 48, wherein XA components are converted directly into said cyclic ester.

79. A process for producing a LD which comprises:
(a) vaporizing a portion of a feedstream comprising LA, wherein the concentration of $L_1A$ is at least about 90 wt/vol %;
(b) passing a nonreactive carrier gas through a reaction zone, wherein said reaction zone contains a gamma alumina esterification catalyst; and
(c) reacting said vaporized portion of said feedstream in said reaction zone maintained at pressure and temperature conditions sufficient to maintain said vaporized portion in a vaporized state and to form said LD.

80. A process for producing LD which comprises:
(a) vaporizing a portion of a feedstream comprising LA, wherein the concentration of $L_1A$ is at least about 70 wt/vol % and wherein the LA has a DP of between about 1.2 and about 4;
(b) passing a nonreactive carrier gas through a reaction zone, wherein said reaction zone contains a gamma alumina esterification catalyst; and
(c) reacting said vaporized portion of said feedstream in said reaction zone maintained at pressure and temperature conditions sufficient to maintain said vaporized portion in a vaporized state and to form said LD.

81. A process for making a cyclic ester from a feedstream comprising XA, comprising removing water from said feedstream until the feedstream has a DP of less than or equal to about 4 to produce said cyclic ester.

82. A process, as claimed in claim 81, wherein at lest about 5% of said XA is converted to said cyclic ester.

83. A process, as claimed in claim 81, wherein said cyclic ester is formed directly from $X_2A$.

84. A process, as claimed in claim 81, wherein said cyclic ester is XD.

85. A process, as claimed in claim 81, wherein XA comprises $X_1A$, and wherein $X_1A$ is an α-hydroxy carboxylic acid, or an ester, salt, or amide thereof.

86. A process, as claimed in claim 81, wherein XA comprises $X_1A$, and wherein $X_1A$ is selected from the acids, esters, salts, or amides of the group consisting of lactic acid, glycolic acid, tartaric acid, mandelic acid, benzylic acid, 1-hydroxy 1-cyclohexane carboxylic acid, 2-hydroxy-2-(2-tertrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methylbutanoic acid, 2-hydroxybutanoic acid, 2-hydroxypentanoic acid and mixtures thereof.

87. A process, as claimed in claim 81, wherein XA comprises $X_1A$, and wherein $X_1A$ is selected from the group consisting of lactic acid, glycolic acid, tartaric acid, a lactate salt, a glycolate salt, a tartarate salt and mixtures thereof.

88. A process, as claimed in claim 81, wherein XA comprises $X_1A$, and wherein $X_1A$ is lactic acid or a lactate salt.

89. A process, as claimed in claim 81, wherein XA comprises $X_1A$, and wherein $X_1A$ is ammonium lactate.

90. A process, as claimed in claim 81, wherein said feedstream comprises at least about 70 wt/vol % LA.

91. A process, as claimed in claim 81, wherein water is removed from said feedstream until the concentration of water is less than about 2 wt % water.

92. A process, as claimed in claim 81, wherein said feedstream comprises heat stable LA, or esters, salts, or amides thereof.

93. A process, as claimed in claim 81, wherein said feedstream comprises fermentation broth containing LA, esters, salts, or amides thereof.

94. A process, as claimed in claim 81, wherein said process is continuous.

95. A process, as claimed in claim 81, further comprising maintaining said feedstream at a temperature of from about 150° C. and about 225° C. at about 10 torr to about 50 torr.

96. A process, as claimed in claim 81, wherein said feedstream further comprises an esterification catalyst.

97. A process, as claimed in claim 96, wherein said catalyst is selected from the group consisting of ion exchange resins, zeolites, soluble acids, alumina-based catalysts, metal catalysts, enzymes, silica-based catalysts, template catalysts, micellar catalysts, and mixtures thereof.

98. A process, as claimed in claim 81, wherein said feedstream further comprises a blocking agent.

99. A process, as claimed in claim 98, wherein said blocking agent is selected from the group consisting of anhydrides, ketones and aldehydes.

100. A process, as claimed in claim 81, further comprising recovering said cyclic ester to form a cyclic-ester containing fraction and a cyclic ester-depleted fraction.

101. A process, as claimed in claim 100, wherein said step of recovering is selected from the group consisting of crystallization, solvent extraction, washing with solvent, chromatography, membrane partitioning, distillation, and sublimation.

102. A process, as claimed in claim 100, wherein said step of recovering comprises crystallization.

103. A process, as claimed in claim 102, wherein said cyclic ester is crystallized from said product-containing stream by a process comprising:

(a) adding a solvent to said stream; and
(b) crystallizing said cyclic ester therefrom.

104. A process, as claimed in claim 103, wherein said solvent comprises toluene, benzene and mixtures thereof.

105. A process, as claimed in claim 102, further comprising drying said crystallized cyclic ester.

106. A process, as claimed in claim 100, wherein said step of recovering comprises solvent extraction.

107. A process, as claimed in claim 106, wherein said step of recovering comprises extracting said cyclic ester into an extraction solvent, wherein said cyclic ester is more soluble in said extraction solvent than in the continuous phase of said feedstream.

108. A process, as claimed in claim 106, wherein said step of recovering comprises adding a solvent to said feedstream from which water has been removed, wherein unreacted components and oligomers of $X_1A$ in said feedstream are more soluble in said solvent than in the continuous phase of said treated feedstream.

109. A process, as claimed in 108, wherein said solvent is an aqueous solvent.

110. A process, as claimed in claim 100, wherein said step of recovering comprises distillation.

111. A process, as claimed in claim 100, wherein said step of recovering comprises codistilling with an organic solvent.

112. A process, as claimed in claim 111, wherein said codistillation solvent comprises an alkyl benzene.

113. A process, as claimed in claim 112, wherein said alkyl benzene is selected from the group consisting of $C_{11}$-$C_{14}$ alkyl benzenes and mixtures thereof.

114. A process, as claimed in claim 100, wherein said cyclic ester-depleted fraction is recycled to said feedstream.

115. A process, as claimed in claim 114, wherein oligomers in said cyclic ester-depleted fraction are hydrolyzed prior to recycling.

116. A process for making LD from a feedstream comprising at least about 70 wt/vol % LA, comprising removing water from said feedstream until the feedstream has a DP of less than or equal to about 4 to produce said LD, wherein at least about 5% of said components are converted to said LD.

117. A process, as claimed in claim 116, wherein water is removed until the feedstream has a DP of between about 1.5 and 3.0.

118. A process, as claimed in claim 116, further comprising continuously separating and purifying said LD.

119. A process, as claimed in claim 81, wherein said step of removing water results in the production of $L_2A$.

120. A process for producing a cyclic ester which comprises:

(a) providing a feedstream comprising XA; and
(b) treating said feedstream to form said cyclic ester directly from the $X_2A$ component of XA.

121. A process, as claimed in claim 113, wherein at least about 5% of said XA is converted to said cyclic ester.

122. A process, as claimed in claim 120, wherein said cyclic ester is XD.

123. A process, as claimed in claim 120, wherein XA comprises $X_1A$, and wherein $X_1A$ is an α-hydroxy carboxylic acid, or an ester, salt, or amide thereof.

124. A process, as claimed in claim 120, wherein XA comprises $X_1A$, and wherein $X_1A$ is selected from the acids, ester, salts, or amide of the group consisting of lactic acid, glycolic acid, tartaric acid, mandelic acid, benzylic acid, 1-hydroxy 1-cyclohexane carboxylic acid, 2-hydroxy-2-(2-tertrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methylbutanoic acid, 2-hydroxybutanoic acid, 2-hydroxypentanoic acid and mixtures thereof.

125. A process, as claimed in claim 120, wherein XA comprises $X_1A$, and wherein $X_1A$ is selected from the group consisting of lactic acid, glycolic acid, tartaric acid, lactate salt, a glycolate salt, a tartrate salt, and mixtures thereof.

126. A process, as claimed in claim 120, wherein XA comprises $X_1A$, and wherein $X_1A$ is lactic acid or a lactate salt.

127. A process, as claimed in claim 120, wherein XA comprises $X_1A$, and wherein $X_1A$ is ammonium lactate.

128. A process, as claimed in claim 120, wherein said feedstream comprises at least about 0.5 wt/vol % LA.

129. A process, as claimed in claim 120, wherein said feedstream initially comprises less than about 50 wt/vol % water.

130. A process, as claimed in claim 120, wherein said feedstream comprises heat stable LA, or esters, salts, or amides thereof.

131. A process, as claimed in claim 120, wherein said feedstream comprises fermentation broth containing LA, or esters, salts, or amides thereof.

132. A process, as claimed in claim 120, wherein the concentration of XA is less than about 75 wt/vol %.

133. A process, as claimed in claim 120, wherein the concentration of XA is less than about 25 wt/vol %.

134. A process, as claimed in claim 120, wherein said feedstream further comprises a compound selected from the group consisting of benzene, toluene, ethyl benzene, xylenes, cumene, trimethyl benzenes, acetonitrile, halogenated aromatic solvents, hydrocarbons and mixtures thereof.

135. A process, as claimed in claim 120, wherein said step of treating comprises removing water from said feedstream.

136. A process, as claimed in claim 135, wherein a feedstream from which water has been removed has a water concentration of less than about 2 wt %.

137. A process, as claimed in claim 120, wherein said step of treating is selected from the group consisting of removing water as an azeotrope from a feedstream in which the components are diluted in an azeotropic solvent, heating at elevated temperature below the vaporization temperature of $X_1A$, adding a water-getter which preferentially reacts with water, using molecular sieves, using an osmotic membrane, using anhydrous salts that form hydrated crystals with water and contacting the feedstream with a compound selected from the group consisting of a polysaccharide or silica.

138. A process, as claimed in claim 120, wherein said step of treating comprises removing water as an azeotrope from a feedstream in which the XA components are diluted in an azeotropic solvent.

139. A process, as claimed in claim 120, wherein said step of treating comprises removing water from said feedstream until said feedstream has a DP of less than or equal to about 4 to produce said cyclic ester directly from $X_2A$.

140. A process, as claimed in claim 120, wherein said feedstream is in vapor phase and wherein said step of treating comprises vaporizing a portion of said feedstream and passing said vaporized portion of said feedstream through a reaction zone maintained at pressure and temperature conditions sufficient to maintain said vaporized portion of said feedstream in a vaporized state and to form said cyclic ester directly from $X_2A$.

141. A process, as claimed in claim 120, wherein said process is continuous.

142. A process, as claimed in claim 141, wherein said step of treating comprises initially dehydrating water-containing components of said feedstream, continuously adding dehydrated additional feedstream thereto, and continuously removing said cyclic ester from the treated feedstream.

143. A process, as claimed in claim 120, wherein the step of treating comprises treating said feedstream at a temperature of between about 55° C. and about 250° C.

144. A process, as claimed in claim 120, wherein said feedstream further comprises an esterification catalyst.

145. A process, as claimed in claim 144, wherein said catalyst is selected from the group consisting of ion exchange resins, zeolites, soluble acids, alumina-based catalysts, metal catalysts, enzymes, silica-based catalysts, template catalysts, micellar catalysts, and mixtures thereof.

146. A process, as claimed in claim 120, wherein said feedstream further comprises a blocking agent.

147. A process, as claimed in claim 146, wherein said blocking agent is selected from the group consisting of anhydrides, ketones and aldehydes.

148. A process, as claimed in claim 120, further comprising recovering said cyclic ester from the treated feedstream to form a cyclic ester-containing fraction and a cyclic ester-depleted fraction.

149. A process, as claimed in claim 148, wherein said step of recovering is selected from the group consisting of crystallization, solvent extraction, washing with solvent, chromatography, membrane partitioning, distillation, and sublimation.

150. A process, as claimed in claim 148, wherein said step of recovering comprises crystallization.

151. A process, as claimed in claim 150, wherein said cyclic ester is crystallized directly from said treated feedstream.

152. A process, as claimed in claim 150, wherein said step of recovering further comprises concentrating said cyclic ester prior to crystallization.

153. A process, as claimed in claim 152, wherein the continuous phase of said treated feedstream is toluene.

154. A process, as claimed in claim 150, wherein the continuous phase of said treated feedstream is removed and said cyclic ester is dissolved in a second continuous phase prior to crystallization.

155. A process, as claimed in claim 151, further comprising drying said crystallized cyclic ester.

156. A process, as claimed in claim 148, wherein said step of recovering comprises solvent extraction.

157. A process, as claimed in claim 156, wherein said step of recovering comprises mixing said treated feedstream with a solvent, wherein said cyclic ester is more soluble in said solvent than in the continuous phase of said treated feedstream.

158. A process, as claimed in claim 156, wherein said step of recovering comprises mixing said treated feedstream with a solvent, wherein said cyclic ester is less soluble in said solvent than in the continuous phase of said treated feedstream.

159. A process, as claimed in claim 158, wherein said solvent is an alkane.

160. A process, as claimed in claim 156, wherein said step of recovering comprises mixing said treated feedstream with a solvent, wherein unreacted components and oligomers of $X_1A$ in said feedstream are more soluble in said solvent than in the continuous phase of said treated feedstream.

161. A process, as claimed in claim 160, wherein said solvent is an aqueous solvent.

162. A process, as claimed in claim 148, wherein said step of recovering comprises distillation.

163. A process, as claimed in claim 162, wherein said step of distillation comprises codistilling with an organic solvent.

164. A process, as claimed in claim 148, wherein said cyclic ester-depleted fraction is recycled to said feedstream.

165. A process, as claimed in claim 164, wherein oligomers in said cyclic ester-depleted fraction are hydrolyzed prior to recycling.

166. A process for producing LD, which comprises:
(a) providing a feedstream comprising LD components selected from the group consisting of $L_1A$, $G_1A$, $L_2A$, $L_1A$-$G_1A$, $G_2A$, and mixtures thereof, wherein the concentration of said LA components is less than about 75 wt/vol %;
(b) removing water from said feedstream to form said LD; and
(c) recovering said LD from said feedstream from which water has been removed.

* * * * *

UNITED STATES PATENT AND TRADEMARK OFFICE
CERTIFICATE OF CORRECTION

PATENT NO. : 5,319,107

DATED : June 7, 1994

INVENTOR(S) : BENECKE et al.

It is certified that error appears in the above-identified patent and that said Letters Patent is hereby corrected as shown below:

On the title page, item [54] and in column 1, line 1:

In the title, delete "Method to Produce Cyclic Esters" and insert therefor --Process For The Production Of Cyclic Esters From Hydroxy Acids And Derivatives Thereof--;

Column 1, lines 6-10, delete "The present application is a continuation-in-part of U.S. Patent Application Serial No. 07/584,126 and U.S. Patent Application Serial No. 07/584,466, both filed September 18, 1990, the disclosures of which are incorporated by reference in their entirety." and insert therefor -- The present application is a continuation-in-part of U.S. Patent Application Serial No. 07/584,126 filed September 18, 1990, the disclosure of which is incorporated by reference in its entirety. --;

Column 14, line 63, after "$L_4A$)," delete "t hat" and insert therefor -- that--;

Column 16, line 1, delete "and $L_3A$" and insert therefor --$L_3A$ and $L_4A$--;

Column 20, line 5, delete "ca" and insert therefor --can--;

Column 28, Table 3, columns 6 and 7, delete
"  —         —
  31.6      25.7
  34.0      30.1
   —
" and insert therefor --        11.91      —
          29.73     31.6
          32.53     34.0
            —               --;

UNITED STATES PATENT AND TRADEMARK OFFICE
CERTIFICATE OF CORRECTION

PATENT NO. : 5,319,107
DATED : June 7, 1994
INVENTOR(S) : BENECKE et al.

It is certified that error appears in the above-identified patent and that said Letters Patent is hereby corrected as shown below:

Column 31, Table 6, column 7, insert "/" after "L-LD";

Column 32, Table 7, column 7, insert "/" after "L-LD";

Column 32, Table 7, column 10, delete "11.53" and insert therefor --11.5--;

Column 33, Table 8, column 7, insert "/" after "L-LD";

Column 33, Table 8, line 12, add "Total material % recovery: (258.5 g/272.4) (100)=94.9%";

Column 33, line 28, delete "absence" and insert therefor --absent--;

Column 33, line 47, after "that", delete "there";

Column 33, line 62, delete "95.4:4.5" and insert therefor --95.5:4.5--;

Column 35, lines 23-24, delete "essentially" and insert therefor --selectivity--;

Column 35, line 38, in the heading, delete "18" and insert therefor --19--;

Column 41, line 5, delete "were" and insert therefor --where--;

Column 47, Table 27, column 3, in the heading, insert "Total" above the word "Material";

UNITED STATES PATENT AND TRADEMARK OFFICE
CERTIFICATE OF CORRECTION

PATENT NO. : 5,319,107
DATED : June 7, 1994
INVENTOR(S) : BENECKE et al.

It is certified that error appears in the above-identified patent and that said Letters Patent is hereby corrected as shown below:

Column 47, Table 27, column 4, in the heading, delete "Total";

Column 60:
Claim 82, line 63, delete "lest" and insert therefor --least--;

Column 62:
Claim 121, line 58, delete "113" and insert therefor --120--;

Column 62:
Claim 124, line 68, delete "amide" and insert therefor --amides--;

Signed and Sealed this

Eighteenth Day of April, 1995

BRUCE LEHMAN

Attest:

Attesting Officer

Commissioner of Patents and Trademarks